(12) United States Patent
Amari et al.

(10) Patent No.: US 8,748,613 B2
(45) Date of Patent: Jun. 10, 2014

(54) QUINUCLIDINE ESTERS OF 1-AZAHETEROCYCLYLACETIC ACID AS ANTIMUSCARINIC AGENTS, PROCESS FOR THEIR PREPARATION AND MEDICINAL COMPOSITIONS THEREOF

(71) Applicant: Chiesi Farmaceutici S.p.A., Parma (IT)

(72) Inventors: Gabriele Amari, Parma (IT); Cristina Pesenti, Parma (IT); Stefano Bossolo, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/729,388

(22) Filed: Dec. 28, 2012

(65) Prior Publication Data

US 2013/0172302 A1    Jul. 4, 2013

(30) Foreign Application Priority Data

Dec. 30, 2011 (EP) .................................... 11196173

(51) Int. Cl.
| | | |
|---|---|---|
| *A01N 43/90* | (2006.01) | |
| *A01N 43/40* | (2006.01) | |
| *A61K 31/44* | (2006.01) | |
| *A61K 31/445* | (2006.01) | |
| *C07D 453/02* | (2006.01) | |
| *C07D 211/00* | (2006.01) | |
| *C07D 295/00* | (2006.01) | |
| *C07D 401/00* | (2006.01) | |
| *C07D 405/00* | (2006.01) | |

(52) U.S. Cl.
USPC ........... 546/137; 514/305; 514/315; 514/318; 514/332; 514/335; 546/133; 546/184; 546/192; 546/206

(58) Field of Classification Search
USPC .................................. 546/347, 137; 514/305
See application file for complete search history.

(56) References Cited

U.S. PATENT DOCUMENTS

| 8,039,483 B2 | 10/2011 | Amari et al. |
|---|---|---|
| 2010/0173880 A1 | 7/2010 | Caligiuri et al. |
| 2011/0308519 A1 | 12/2011 | Schiaretti |
| 2011/0311458 A1 | 12/2011 | Amari et al. |
| 2011/0311459 A1 | 12/2011 | Amari et al. |
| 2011/0311461 A1 | 12/2011 | Amari et al. |
| 2011/0319444 A1 | 12/2011 | Amari et al. |
| 2012/0004258 A1 | 1/2012 | Amari et al. |
| 2012/0101076 A1 | 4/2012 | Patacchini et al. |
| 2012/0134934 A1 | 5/2012 | Amari et al. |
| 2012/0276018 A1 | 11/2012 | Amari et al. |

FOREIGN PATENT DOCUMENTS

WO    2008/075005    6/2008

OTHER PUBLICATIONS

Hallett, et. al.; Journal of the Chemical Society, Chemical Communications, (6), 657-8; 1995.*
Modern Pharmacology with Clinical Applications, 6$^{th}$ Ed., B. Sun, Ed., Lippincott Wiliams & Wilkins, Philadelphia, 2004, pp. 134-141.
European Search Report issued in Application No. 11196173.6 on Mar. 7, 2012.
Antonio Mete et al., Bioorganic & Medicinal Chemistry Letters, vol. 21, No. 24 (2011) pp. 7440-7446.

* cited by examiner

*Primary Examiner* — John Mabry
*Assistant Examiner* — Daniel Carcanague
(74) *Attorney, Agent, or Firm* — Oblon, Spivak, McClelland, Maier & Neustadt, L.L.P.

(57) ABSTRACT

Compounds of formula (I):

wherein A, R1, R2, X, m, and n are as defined in the specification, are selective M3 receptor antagonists and may be used in the treatment of, inter alia, a respiratory disease such as asthma and COPD.

15 Claims, No Drawings

QUINUCLIDINE ESTERS OF 1-AZAHETEROCYCLYLACETIC ACID AS ANTIMUSCARINIC AGENTS, PROCESS FOR THEIR PREPARATION AND MEDICINAL COMPOSITIONS THEREOF

CROSS REFERENCES TO RELATED APPLICATIONS

This application claims priority to European Patent Application No. 11196173.6, filed on Dec. 30, 2011, which is incorporated herein by reference in its entirety.

BACKGROUND OF THE INVENTION

1. Field of the Invention

The present invention relates to quinuclidine esters of 1-azaheterocyclylacetic acid analogues which act as muscarinic receptor antagonists. The present invention also relates to processes for the preparation of such quinuclidine esters of 1-azaheterocyclylacetic acid analogues, compositions which comprise such quinuclidine esters of 1-azaheterocyclylacetic acid analogues, and therapeutic uses of such quinuclidine esters of 1-azaheterocyclylacetic acid analogues.

2. Discussion of the Background

Quaternary ammonium salts which act as muscarinic (M) receptor antagonist drugs are currently used in therapy to induce bronchodilation for the treatment of respiratory diseases. Examples of well known M receptor antagonists are represented by ipratropium bromide and tiotropium bromide.

Several chemical classes which act as selective muscarinic M3 receptor antagonist drugs have been developed for the treatment of inflammatory or obstructive airway diseases such as asthma and chronic obstructive pulmonary disease (COPD). Quinuclidine carbamate derivatives and their use as M3 antagonists are for instance disclosed in WO 02/051841, WO 03/053966, and WO 2008/012290, all of which are incorporated herein by reference in their entireties.

WO 2010/015324, which is incorporated herein by reference in its entirety, describes carbonate derivatives and their use as M3 antagonists.

1-ethyl-3-piperidinyl ester of optionally substituted alfa-phenyl-1-piperidine-/1-pyrrolidine-/4-morpholine-acetic acid have been described for their spasmolytic activity with respect to acetylcholine in U.S. Pat. No. 2,952,685 and in Bull. Soc. Chim. France, 355-359, 1958, which are incorporated herein by reference in their entireties.

1-methyl-3-piperidinyl ester of alfa-phenyl-1-piperidine-acetic acid and analogues have been prepared and tested as potential psychotropic drugs for their psychotomimetic properties in Chim. Ther., 7, 408-414, 1966, which is incorporated herein by reference in its entirety.

Quaternary ammonium salts of quinuclidine esters of alfa-phenyl-alfa-methyl-1-piperidine-acetic acid and analogues have been described in WO 2008/075005, WO 2009/153536, and Bioorg Med Chem Lett (2011), doi:10.1016/j.bmcl.2011.10.002, which are incorporated herein by reference in their entireties. Said compounds which have a methyl group in place of the hydroxyl group of the well known M3 antagonists of the prior art (tiotropium, glycopyrrolate, aclidinium bromide) would have higher probability to bind to plasma proteins.

It is however highly desirable to provide M3 receptor antagonists which can be administered by inhalation, are capable of acting locally, while having a high potency and long duration of action. Said drugs, once adsorbed, should be degraded to inactive compounds which are deprived of any systemic side effects typical of muscarinic antagonists.

SUMMARY OF THE INVENTION

Accordingly, it is one object of the present invention to provide novel M3 receptor antagonists.

It is another object of the present invention to provide novel M3 receptor antagonists which can be administered by inhalation.

It is another object of the present invention to provide novel M3 receptor antagonists which are capable of acting locally.

It is another object of the present invention to provide novel M3 receptor antagonists which have a high potency.

It is another object of the present invention to provide novel M3 receptor antagonists which have a long duration of action.

It is another object of the present invention to provide novel M3 receptor antagonists which, once adsorbed, are degraded to inactive compounds which are deprived of any systemic side effects typical of muscarinic antagonists.

It is another object of the present invention to provide novel methods of preparing such a M3 receptor antagonist.

It is another object of the present invention to prepare novel compositions which contain such a M3 receptor antagonist.

It is another object of the present invention to provide novel methods of treating certain diseases and conditions by administering such a M3 receptor antagonist.

These and other objects, which will become apparent during the following detailed description, have been achieved by the inventors' discovery that quinuclidine esters of 1-azaheterocyclylacetic acid analogues, of general formula (I), act as selective M3 receptor antagonists and are capable of being administered by inhalation and of acting locally.

The compounds according to the present invention are able to produce a persistent bronchodilating effect in the lung but are consistently and rapidly transformed into inactive metabolites after passing into human plasma. This behaviour gives great advantages in terms of safety.

DETAILED DESCRIPTION OF THE PREFERRED EMBODIMENTS

In particular, the present invention provides quinuclidine esters of 1-azaheterocyclylacetic acid of formula (I):

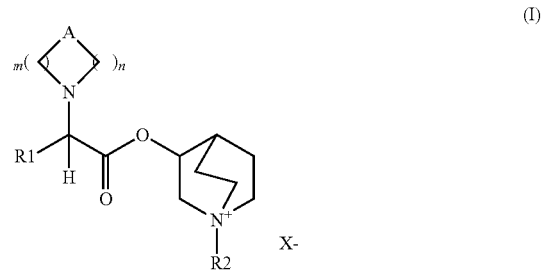

wherein:
A may be a single bond, double bond, O, S, SO, $SO_2$, $NR_3$, $C(R_3)R_4$, CO, $C(O)N(R_3)$, $N(R_3)C(O)O$, $SO_2N(R_3)$, $N(R_3)C(O)$, $OC(O)N(R_3)$, $N(R_3)SO_2$, $C(R_3)=C(R_4)$, or $C(R_3)—(CH_2)—C(R_4)$
m is an integer of 1 to 4;
n is 0 or an integer of 1 to 4;
R1 is selected from the group consisting of $(C_1-C_{10})$-alkyl, aryl, $(C_3-C_8)$-cycloalkyl, heteroaryl, aryl$(C_1-C_6)$alkyl, and heteroaryl($C_1$-$C_6$)alkyl, optionally substituted by one or more substituents selected from the group consisting of a halogen atom, OH, oxo (=O), SH, $NO_2$, CN, $CON(R_3)_2$, COOH, $CO_2R_3$, $CF_3$, ($C_1$-$C_{10}$)-alkoxycarbonyl, ($C_1$-$C_{10}$)-alkyl sulfanyl, ($C_1$-$C_{10}$)-alkylsulfinyl, ($C_1$-$C_{10}$)-alkylsulfonyl, ($C_1$-$C_{10}$)-alkyl, ($C_1$-$C_{10}$)-alkoxyl, aryloxy and heteroaryl; wherein $X^-$ is a physiologically acceptable anion;

R2 is a group of formula (Y):

—($CH_2$)p-P—($CH_2$)q-W         (Y)

wherein p is 0 or an integer of 1 to 4;

q is 0 or an integer of 1 to 4;

P is absent or is selected from the group consisting of O, S, SO, $SO_2$, CO, $NR_3$, CH=CH, $N(R_3)SO_2$, $N(R_3)COO$, $N(R_3)C(O)$, $SO_2N(R_3)$, $CO(O)N(R_3)$, and $C(O)N(R_3)$;

W is selected from the group consisting of H, ($C_1$-$C_{10}$)-alkyl, ($C_1$-$C_{10}$)-alkoxyl, ($C_3$-$C_8$)-cycloalkyl, aryl, heteroaryl, and ($C_5$-$C_{10}$)heterocycloalkyl, optionally substituted by one or more substituents selected from the group consisting of a halogen atom, OH, oxo (=O), SH, $NO_2$, CN, $CON(R_3)_2$, COOH, $NH_2$, $NHCOR_3$, $CO_2R_3$, ($C_1$-$C_{10}$)-alkoxycarbonyl, ($C_1$-$C_{10}$)-alkylsulfanyl, ($C_1$-$C_{10}$)-alkylsulfinyl, ($C_1$-$C_{10}$)-alkylsulfonyl, ($C_1$-$C_{10}$)-alkyl, ($C_1$-$C_{10}$)-alkoxyl, ($C_1$-$C_{10}$)alkanoyl, and aryl;

R3 and R4 are independently selected from the group consisting of H, a halogen atom, $CONH_2$, ($C_1$-$C_{10}$)alkyl, ($C_2$-$C_6$) alkynyl, ($C_2$-$C_6$)alkenyl, ($C_1$-$C_{10}$)alkanoyl, ($C_3$-$C_8$)cycloalkyl, heteroaryl, and aryl optionally substituted by one or more substituents selected from the group consisting of a halogen atom, OH, oxo (=O), SH, $NO_2$, CN, $CONH_2$, COOH, ($C_1$-$C_{10}$)-alkoxycarbonyl, ($C_1$-$C_{10}$)-alkylsulfanyl, ($C_1$-$C_{10}$)-alkylsulfinyl, ($C_1$-$C_{10}$)-alkylsulfonyl, ($C_1$-$C_{10}$)-alkyl, ($C_1$-$C_{10}$)-alkoxyl and ($C_3$-$C_7$)-cycloalkyl.

The present invention also provides compounds of formula (II):

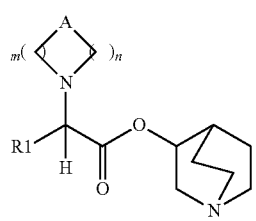

(II)

wherein A, R1, m, and n are as described above and a pharmaceutical acceptable salt thereof.

The present invention also provides processes for the preparation of a compound of formula (I) as reported in Scheme 1 by:

(a) coupling a compound of formula (IX), in which K may be an alkoxy, an hydroxy group, or an halogen such as chlorine and A, R1 are as defined above, with a compound of formula (X), in which J is H, Na, Li, or K, to give a compound of formula (II),

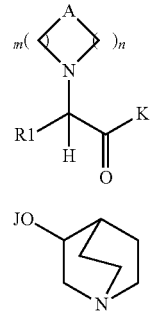

(IX)

(X)

(b) alkylating a compound of formula (II) with an alkylating agent of formula (XI)

X—R2         (XI)

in which R2 is as defined above and X is a suitable leaving group selected from the group consisting of a halogen atom and a sulfonate ester such as a tosylate, triflate, or mesylate to provide compounds of general formula (I).

The present invention also provides pharmaceutical compositions of compounds of formula (I) or of formula (II) alone or in combination with or in admixture with one or more pharmaceutically acceptable carriers and/or excipients.

The present invention also provides compounds of formula (I) or (II) for use as a medicament.

In a further aspect, the present invention provides the use of compounds of formula (I) or of formula (II) for the manufacture of a medicament for the prevention and/or treatment of broncho-obstructive or inflammatory diseases, preferably asthma or chronic bronchitis or chronic obstructive pulmonary disease (COPD).

The present invention also provides methods for the prevention and/or treatment of broncho-obstructive or inflammatory diseases, preferably asthma or chronic bronchitis or chronic obstructive pulmonary disease (COPD), which comprise administering to a subject in need thereof a therapeutically effective amount of a compound of formula (I) or (II).

The present invention also provides pharmaceutical preparations of compounds of formula (I) or formula (II) suitable for administration by inhalation, such as inhalable powders, propellant-driven pressurized metered dose aerosol inhalers or propellant-free inhalable formulations.

The present invention also provides devices which may be a single- or multi-dose dry powder inhaler, a metered dose inhaler, or a soft mist nebulizer which comprise a compound of formula (I) or (II).

The present invention also provides kits which comprise a pharmaceutical composition of a compound of formula (I) or (II) alone or in combination with or in admixture with one or more pharmaceutically acceptable carriers and/or excipients and a device which may be a single- or multi-dose dry powder inhaler, a metered dose inhaler, or a soft mist nebulizer comprising a compound of formula (I) or (II).

In the present disclosure, unless otherwise specified, the term "halogen" includes fluorine, chlorine, bromine, and iodine atoms.

The expression "($C_1$-$C_{10}$)alkyl" refers to straight or branched chain alkyl groups wherein the number of carbon atoms is from 1 to 10. Examples of said groups are methyl, ethyl, n-propyl, isopropyl, n-butyl, isobutyl, sec-butyl, tert-butyl, pentyl, hexyl, heptyl, octyl, nonyl, decyl, and the like.

The expression "($C_2$-$C_6$)alkenyl" refers to straight or branched carbon chains with one or more double bonds. Examples of said groups are ethenyl, propenyl, butenyl, pentenyl, hexenyl, and the like.

The expression "($C_1$-$C_{10}$)alkoxyl" refers to the above alkyl-oxy (e.g. alkoxy) groups. Examples of said groups are methoxy, ethoxy, n-propoxy, isopropoxy, n-butoxy, isobutoxy, sec-butoxy, tert-butoxy, pentoxy, hexoxy, and the like.

The expression "($C_1$-$C_{10}$)alkanoyl" refers to a carbonyl residue substituted by a hydrogen atom or by a straight or branched alkyl group from 1 to 9 carbon atoms. Examples of said groups are formyl, acetyl, propanoyl, butanoyl, isobutanoyl, and pivaloyl.

Likewise, the expressions "($C_1$-$C_{10}$)alkylsulfanyl," "($C_1$-$C_{10}$)alkylsulfinyl," and "($C_1$-$C_{10}$)alkylsulfonyl" refer, respectively, to alkyl-S—, alkyl-SO— or alkyl-$SO_2$— groups.

The expression "($C_3$-$C_8$)cycloalkyl" refers to cyclic non-aromatic hydrocarbon groups with 3 to 8 carbon atoms. Examples include cyclopropyl, cyclobutyl, cyclopentyl, cyclohexyl, cycloheptyl, cyclooctyl, and the like.

The expression "($C_5$-$C_{10}$)heterocycloalkyl" refers to cyclic non-aromatic systems which have 5 to 10 ring atoms, in which at least one ring atom is a heteroatom (e.g. N, NH, S, or O).

The expression "aryl" refers to mono-, or bi-, or tricyclic ring systems which have 6 to 20 ring atoms, preferably 6 to 15 and wherein at least one ring is aromatic.

The expressions "aryl($C_1$-$C_6$)alkyl" and "heteroaryl($C_1$-$C_6$)alkyl" refer to ($C_1$-$C_6$)alkyl groups further substituted by aryl or heteroaryl rings.

The expression "aryloxy" refers to the above aryl-oxy group. An example may be phenyloxy.

The expression "heteroaryl" refers to mono-, bi-, or tricyclic ring systems which have 5 to 20 ring atoms, preferably 5 to 15, in which at least one ring is aromatic and in which at least one ring atom is a heteroatom or heteroaromatic group (e.g. N, NH, S, or O).

Examples of suitable aryl or heteroaryl monocyclic systems include for instance thienyl, phenyl, pyrrolyl, pyrazolyl, imidazolyl, isoxazolyl, oxazolyl, oxadiazolyl, isothiazolyl, thiazolyl, pyridinyl, imidazolidinyl, and furanyl residues and the like.

Examples of suitable aryl or heteroaryl bicyclic systems include benzodioxole (benzodioxolyl), naphthalene (naphthyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxine (dihydrobenzo dioxinyl), dihydrobenzo dioxepin (dihydrobenzo dioxepinyl), and benzo oxazin (benzo oxazinyl), and benzothioxole (benzothioxolyl) residues and the like.

Advantageously, the physiologically acceptable anions $X^-$ include those selected from chloride, bromide, iodide, trifluoroacetate, formate, sulfate, phosphate, methanesulfonate, nitrate, maleate, acetate, citrate, fumarate, tartrate, oxalate, succinate, benzoate, and p-toluenesulfonate.

Besides the presence of $X^-$ anion, whenever further basic amino groups are present in the compounds of formula (I) or (II), additional physiological and/or pharmaceutically acceptable anions, among those formerly indicated, may be present to form an acid addition salt with an inorganic or organic acid. Likewise, in the presence of acidic groups such as COOH groups, corresponding physiological cation salts may be present as well, for instance including alkali or earth-alkali metal ion or an ammonium ion.

Suitable inorganic acids to form an acid addition salt of a compound of formula (I) or (II) are selected from hydrohalogen acids such as hydrofluoric acid, hydrochloric acid, hydrobromic acid, and hydroiodic acid, but also from nitric acid, sulfuric acid, and phosphoric acid. Suitable organic acids to form an acid addition salt of a compound of formula (I) or (II) are selected from: aliphatic monocarboxylic acids such as formic acid, acetic acid, trifluoroacetic acid and propionic acid; aliphatic hydroxy acids such as lactic, citric, tartaric, and malic acids; dicarboxylic acids such as maleic or succinic acid; aromatic carboxylic acids such as benzoic acid; aromatic hydroxy acids and sulfonic acids.

A first preferred group of compounds of formula (I) or (II) is that wherein A is selected from O, S, N($R_3$), and C($R_3$)$R_4$, R1 is selected from the group consisting of aryl, aryl($C_1$-$C_6$)alkyl, and heteroaryl, optionally substituted by one or more substituents selected from a halogen atom, ($C_1$-$C_{10}$)alkyl, ($C_1$-$C_{10}$)alkoxyl, aryloxy, and heteroaryl; and R3 is as defined above.

Still more preferred, within this class, are the compounds of formula (I) or (II) wherein A is C($R_3$)$R_4$, R1 is selected from the group consisting of aryl and heteroaryl, optionally substituted by one or more substituents selected from a halogen atom, ($C_1$-$C_{10}$)alkyl, ($C_1$-$C_{10}$)alkoxyl, aryloxy and heteroaryl; m and n are both 2 and R3 is a group of formula (Y) wherein p is 0, 1, or 3, P is CO, q is 0, W is selected from the group consisting of ($C_1$-$C_{10}$)alkyl, aryl, heteroaryl, optionally substituted by one or more substituents selected from the group consisting of a halogen atom, ($C_1$-$C_{10}$)alkyl, ($C_1$-$C_{10}$)alkoxyl, OH, and ($C_1$-$C_{10}$)alkanoyl.

Still more preferred, within this class, are the compounds of formula (I) wherein W is selected from the group consisting of phenyl, benzothioxolyl, thiophenyl, and thiazolyl, optionally substituted by one or more halogen atoms, OH, methyl, and acetyl.

It will be apparent to those skilled in the art that the compounds of general formula (I) and (II) contain asymmetric centers. Therefore the invention also includes the optical stereoisomers and mixtures thereof.

The active compounds of formula (I) and (II) show at least two chiral centers, which are respectively represented by the quinuclidine carbon atom bearing the oxygen ester group and the carbon atom bearing R1 group. These compounds of formula (I) and (II) can be obtained in pure S—R, R—R, R—S, S—S configurations or as mixtures of diastereoisomers.

Further, depending on the meanings of R1, R2, R3, and A it will be clear that additional asymmetric centers may be present in the compounds of formula (I) and (II). Therefore, the invention also includes any of the optical stereoisomers, diastereoisomers and mixtures thereof, in any proportion.

According to specific embodiments, the present invention provides the compounds reported below:

| Compound | Chemical name |
| --- | --- |
| C3 | (R)-quinuclidin-3-yl 2-phenyl-2-(piperidin-1-yl)acetate |
| C4 | (3R)-1-(2-oxo-2-phenylethyl)-3-(2-phenyl-2-(piperidin-1-yl)acetoxy)-1-azonia bicyclo[2.2.2]octane bromide |

-continued

| Compound | Chemical name |
|---|---|
| C5 | (3R)-1-(2-oxo-2-(thiophen-2-yl)ethyl)-3-(2-phenyl-2-(piperidin-1-yl)acetoxy)-1-azonia-bicyclo[2.2.2]octane trifluoroacetate trifluoroacetate anion |
| C6 | (3R)-1-(2-(4-chlorophenyl)-2-oxoethyl)-3-(2-phenyl-2-(piperidin-1-yl)acetoxy)-1-azoniabicyclo[2.2.2]octane bromide |
| C7 | (3R)-1-(2-oxo-2-p-tolylethyl)-3-(2-phenyl-2-(piperidin-1-yl)acetoxy)-1-azoniabicyclo[2.2.2]octane bromide |
| C8 | (3R)-1-(2-(4-hydroxyphenyl)-2-oxoethyl)-3-(2-phenyl-2-(piperidin-1-yl)acetoxy)-1-azoniabicyclo[2.2.2]octane bromide |
| C9 | (3R)-1-(2-(benzo[b]thiophen-5-yl)-2-oxoethyl)-3-(2-phenyl-2-(piperidin-1-yl)acetoxy)-1-azoniabicyclo[2.2.2]octane bromide |
| C10 | (3R)-1-(2-(4-methoxyphenyl)-2-oxoethyl)-3-(2-phenyl-2-(piperidin-1-yl)acetoxy)-1-azoniabicyclo[2.2.2]octane bromide |
| C11 | (3R)-1-(2-(4-fluorophenyl)-2-oxoethyl)-3-(2-phenyl-2-(piperidin-1-yl)acetoxy)-1-azoniabicyclo[2.2.2]octane bromide |
| C12 | (3R)-1-(2-(3-fluorophenyl)-2-oxoethyl)-3-(2-phenyl-2-(piperidin-1-yl)acetoxy)-1-azoniabicyclo[2.2.2]octane bromide |
| C13 | (3R)-1-(2-(2-fluorophenyl)-2-oxoethyl)-3-(2-phenyl-2-(piperidin-1-yl)acetoxy)-1-azoniabicyclo[2.2.2]octane bromide |
| C14 | (3R)-1-(2-(3,4-difluorophenyl)-2-oxoethyl)-3-(2-phenyl-2-(piperidin-1-yl)acetoxy)-1-azoniabicyclo[2.2.2]octane bromide |
| C15 | (3R)-1-(2-(5-chlorothiophen-2-yl)-2-oxoethyl)-3-(2-phenyl-2-(piperidin-1-yl)acetoxy)-1-azoniabicyclo[2.2.2]octane bromide |
| C16 | (3R)-1-(2-tert-butoxy-2-oxoethyl)-3-(2-phenyl-2-(piperidin-1-yl)acetoxy)-1-azoniabicyclo[2.2.2]octane bromide |
| C17 | (3R)-1-(2-oxo-2-(thiazol-2-yl)ethyl)-3-(2-phenyl-2-(piperidin-1-yl)acetoxy)-1-azoniabicyclo[2.2.2]octane bromide |
| C18 | (3R)-1-(2-(3-(ethoxycarbonyl)isoxazol-5-yl)-2-oxoethyl)-3-(2-phenyl-2-(piperidin-1-yl)acetoxy)-1-azoniabicyclo[2.2.2]octane bromide |
| C19 | (3R)-1-(2-oxo-2-(thiophen-3-yl)ethyl)-3-(2-phenyl-2-(piperidin-1-yl)acetoxy)-1-azoniabicyclo[2.2.2]octane bromide |
| C21 | (3R)-1-((5-phenyl-1,2,4-oxadiazol-3-yl)methyl)-3-(2-phenyl-2-(piperidin-1-yl)acetoxy)-1-azoniabicyclo[2.2.2]octane chloride |
| C23 | (3R)-3-(2-phenyl-2-(piperidin-1-yl)acetoxy)-1-((2-phenyloxazol-4-yl)methyl)-1-azoniabicyclo[2.2.2]octane chloride |
| C25 | (3R)-1-(2-(isoxazol-3-ylamino)-2-oxoethyl)-3-(2-phenyl-2-(piperidin-1-yl)acetoxy)-1-azoniabicyclo[2.2.2]octane chloride |
| C26 | (3R)-1-(4-fluorophenethyl)-3-(2-phenyl-2-(piperidin-1-yl)acetoxy)-1-azoniabicyclo[2.2.2]octane 2,2,2-trifluoroacetate |
| C32 | (R)-quinuclidin-3-yl 2-(4-methylpiperidin-1-yl)-2-phenylacetate |
| C33 | (3R)-3-(2-(4-methylpiperidin-1-yl)-2-phenylacetoxy)-1-(2-oxo-2-phenylethyl)-1-azoniabicyclo[2.2.2]octane bromide |
| C36 | (R)-quinuclidin-3-yl 2-phenyl-2-(pyrrolidin-1-yl)acetate |
| C37 | (3R)-1-(2-oxo-2-phenylethyl)-3-(2-phenyl-2-(pyrrolidin-1-yl)acetoxy)-1-azoniabicyclo[2.2.2]octane chloride |
| C40 | (R)-quinuclidin-3-yl 2-morpholino-2-phenylacetate |
| C41 | (3R)-3-(2-morpholino-2-phenylacetoxy)-1-(2-oxo-2-phenylethyl)-1-azoniabicyclo[2.2.2]octane chloride |
| C44 | (R)-quinuclidin-3-yl 2-phenyl-2-thiomorpholinoacetate |
| C45 | (3R)-1-(2-oxo-2-phenylethyl)-3-(2-phenyl-2-thiomorpholinoacetoxy)-1-azoniabicyclo[2.2.2]octane chloride |
| C52 | (R)-quinuclidin-3-yl 2-(4-methyl-3-oxopiperazin-1-yl)-2-phenylacetate |
| C53 | (3R)-3-(2-(4-methyl-3-oxopiperazin-1-yl)-2-phenylacetoxy)-1-(2-oxo-2-phenylethyl)-1-azoniabicyclo[2.2.2]octane chloride |
| C56 | (R)-quinuclidin-3-yl 2-(4-acetylpiperazin-1-yl)-2-phenylacetate |
| C57 | (3R)-3-(2-(4-acetylpiperazin-1-yl)-2-phenylacetoxy)-1-(2-oxo-2-phenylethyl)-1-azoniabicyclo[2.2.2]octane chloride |
| C60 | (R)-quinuclidin-3-yl 2-(4-carbamoylpiperidin-1-yl)-2-phenylacetate |
| C61 | (3R)-3-(2-(4-carbamoylpiperidin-1-yl)-2-phenylacetoxy)-1-(2-oxo-2-phenylethyl)-1-azoniabicyclo[2.2.2]octane chloride |
| C63 | (R)-quinuclidin-3-yl 2-(3,5-dimethylpiperidin-1-yl)-2-phenylacetate |
| C64 | (3R)-3-(2-(3,5-dimethylpiperidin-1-yl)-2-phenylacetoxy)-1-(2-oxo-2-phenylethyl)-1-azoniabicyclo[2.2.2]octane bromide |
| C69 | (R)-Quinuclidin-3-yl 2-(4,4-difluoropiperidin-1-yl)-2-phenylacetate |
| C70 | (3R)-3-(2-(4,4-difluoropiperidin-1-yl)-2-phenylacetoxy)-1-(2-oxo-2-phenylethyl)-1-azoniabicyclo[2.2.2]octane chloride |
| C72 | (R)-quinuclidin-3-yl 2-(azepan-1-yl)-2-phenylacetate |
| C73 | (3R)-3-(2-(azepan-1-yl)-2-phenylacetoxy)-1-(2-oxo-2-phenylethyl)-1-azoniabicyclo[2.2.2]octane chloride |
| C75 | (R)-quinuclidin-3-yl 2-((R)-2-methylpyrrolidin-1-yl)-2-phenylacetate |
| C76 | (3R)-3-(2-((R)-2-methylpyrrolidin-1-yl)-2-phenylacetoxy)-1-(2-oxo-2-phenylethyl)-1-azoniabicyclo[2.2.2]octane chloride |
| C79 | (R)-quinuclidin-3-yl 2-(2-oxopyrrolidin-1-yl)-2-phenylacetate |
| C80 | (3R)-1-(2-oxo-2-phenylethyl)-3-(2-(2-oxopyrrolidin-1-yl)-2-phenylacetoxy)-1-azoniabicyclo[2.2.2]octane chloride |
| C83 | (R)-quinuclidin-3-yl 2-(3-fluorophenyl)-2-(piperidin-1-yl)acetate |
| C84 | (3R)-3-(2-(3-fluorophenyl)-2-(piperidin-1-yl)acetoxy)-1-(2-oxo-2-phenylethyl)-1-azoniabicyclo[2.2.2]octane bromide |

| Compound | Chemical name |
|---|---|
| C87 | (R)-quinuclidin-3-yl 2-(piperidin-1-yl)-2-p-tolylacetate |
| C88 | (3R)-1-(2-oxo-2-phenylethyl)-3-(2-(piperidin-1-yl)-2-p-tolylacetoxy)-1-azoniabicyclo[2.2.2]octane trifluoroacetate trifluoroacetate anion |
| C91 | (R)-quinuclidin-3-yl 2-(4-methoxyphenyl)-2-(piperidin-1-yl)acetate |
| C92 | (3R)-3-(2-(4-methoxyphenyl)-2-(piperidin-1-yl)acetoxy)-1-(2-oxo-2-phenylethyl)-1-azoniabicyclo[2.2.2]octane trifluoroacetate, trifluoroacetate anion |
| C94 | (R)-quinuclidin-3-yl 2-(4-chlorophenyl)-2-(piperidin-1-yl)acetate |
| C95 | (3R)-3-(2-(4-chlorophenyl)-2-(piperidin-1-yl)acetoxy)-1-(2-oxo-2-phenylethyl)-1-azoniabicyclo[2.2.2]octane bromide |
| C98 | (R)-quinuclidin-3-yl 2-(4-fluorophenyl)-2-(piperidin-1-yl)acetate |
| C99 | (3R)-3-(2-(4-fluorophenyl)-2-(piperidin-1-yl)acetoxy)-1-(2-oxo-2-phenylethyl)-1-azoniabicyclo[2.2.2]octane chloride |
| C100 | (3R)-1-(2-(4-chlorophenyl)-2-oxoethyl)-3-(2-phenyl-2-(piperidin-1-yl)acetoxy)-1-azoniabicyclo[2.2.2]octane bromide |
| C102 | (R)-quinuclidin-3-yl 2-(2,4-difluorophenyl)-2-(piperidin-1-yl)acetate |
| C103 | (3R)-3-(2-(2,4-difluorophenyl)-2-(piperidin-1-yl)acetoxy)-1-(2-oxo-2-phenylethyl)-1-azoniabicyclo[2.2.2]octane chloride |
| C105 | (R)-quinuclidin-3-yl 2-(piperidin-1-yl)-2-(thiophen-2-yl)acetate |
| C106 | (3R)-1-(2-oxo-2-phenylethyl)-3-(2-(piperidin-1-yl)-2-(thiophen-2-yl)acetoxy)-1-azoniabicyclo[2.2.2]octane chloride |
| C108 | (R)-quinuclidin-3-yl 2-(piperidin-1-yl)-2-(thiophen-3-yl)acetate |
| C109 | (3R)-1-(2-oxo-2-phenylethyl)-3-(2-(piperidin-1-yl)-2-(thiophen-3-yl)acetoxy)-1-azoniabicyclo[2.2.2]octane chloride |

The compounds of formula (I) and (II) may be prepared according to known methods. Some of the processes which may be used are described below and reported in Scheme 1.

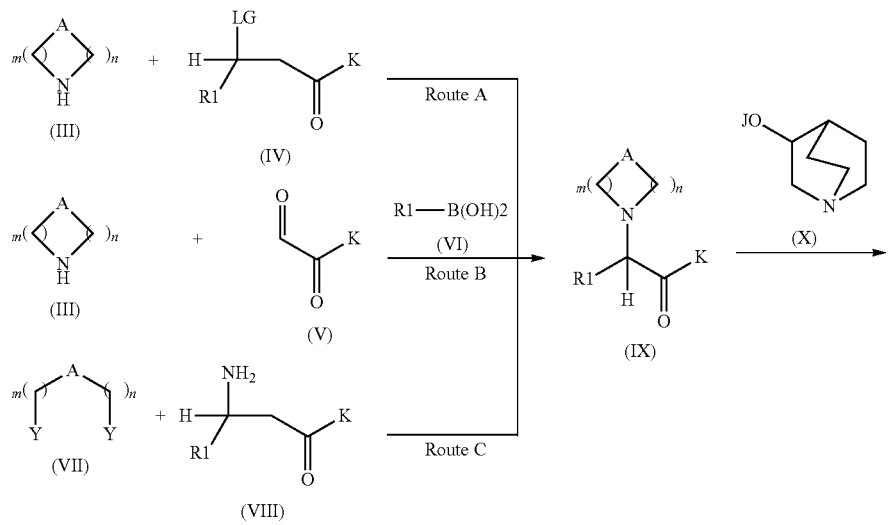

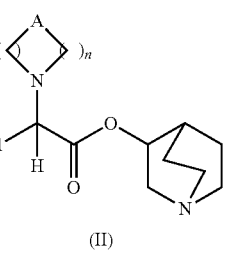

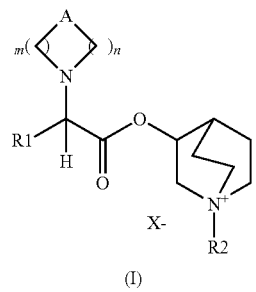

(I)

Procedure for the preparation of compounds of formula (I) and (II).

Compounds of formula (IX) may be prepared according to standard procedures extensively reported in literature (for example following the procedure reported by Kiskinen et al., in Tetrahedron, 1983, 39/9, 1627; Haurena et al. in J. O. C., 2010, 75/8, 264; Najer, Bulletin de la Societe Chimique de France, 1958, 1189; and Duan et al. Bioorganic and Medicinal Chemistry Letters, 2009, 19/6, 1610, all of which are incorporated herein by reference in their entireties). Most preferably, the compounds of formula (IX) may be prepared according to three different routes: A, B and C.

Route A. Compounds of formula (IX) may be prepared through the alkylation of a reagent of formula (III) with a compound of formula (IV), in which LG is a suitable leaving group (a halide such as a bromide or a sulfonic ester group such as a mesylate) and K is a carboxyl group in an optionally protected form (typically including carboxyalkyl ester groups (e.g. K=O($C_1$-$C_6$)alkyl) such as a carboxymethyl (K=OMe). This alkylation can be carried out following one of the standard procedures broadly reported in literature (for instance, Melloni et al., European Journal of Medicinal Chemistry, 1984, 19/3, 235; Duran et al., Journal of Medicinal Chemistry, 1965, 8, 598; Venkatesan, A. M. et al., Journal of Medicinal Chemistry, 2004, 47/25, 6255; and Wlasislaw, B. et al. Synthesis, 1997, 4, 420, all of which are incorporated herein by reference in their entireties).

In a typical procedure, the alkylation reaction is promoted by the presence of a base, for instance an amine selected from the group consisting of triethylamine, diisopropylethylamine, pyridine, and 4-dimethylaminopyridine or an inorganic base such as potassium carbonate or sodium hydride. The reaction is generally performed in a suitable solvent (e.g. acetonitrile, THF, or DMF) in a temperature range of about 0° C. to about 130° C. over a period of about 1 hour up to about 74 hours. The reaction may be conducted under conventional heating (using an oil bath) or under microwave heating. The reaction may be carried out in an open vessel or in a sealed tube.

Reagents of formula (IV) are commercially available or may be conveniently prepared according to standard procedures extensively reported in literature. For instance compounds of general formula (IV) in which LG is a halogen such as a bromine, may be prepared by halogenation of the opportunely substituted phenyl acetic ester (for example following the procedure reported by Epstein, J. W. in J. Med. Chem., 1981, 24/5, 481, which is incorporated herein by reference in its entirety). Alternatively, compounds of formula (IV) may be prepared starting from the appropriately substituted mandelic derivative (IV), using known procedures (a survey of the suitable reactions is given by Larock, L.C., Comprehensive Organic Transformation, Second edition (1999), John Wiley & Son Inc, pg 689-700, which is incorporated herein by reference in its entirety). The mandelic derivative of general formula (IV) can be directly coupled with reagent of formula (III) by means of Mitsunobu reaction (Kumara Swamy, K. C. et al. Chem. Rev. 2009, 109, 2551; and Powell, N. A. et al. Bioorganic and Medicinal Chemistry 2007, 15/17, 5912, which are incorporated herein by reference in their entireties). The reaction typically was conducted in the presence of a phospine (e.g. triphenylphosphine) and azodicarboxylate (e.g. diisopropyl azodicarboxylate or diethyl azodicarboxylate), in a suitable solvent (such as DCM and THF) and in a temperature range of −10° C. to 110° C. over a period of 1 hour up to 74 hours.

Route B. According to Route B, compounds of general formula (IX) might be prepared by means of a Petasis-Mannich reaction following one of the different procedures reported in literature (e.g.: Petasis N. A., Akritopoulou I., Tetrahedron Lett. 1993, 34, 583; Follmann, M., Synlett, 2005, 6, 1009; and Kausik K. N., Tetrahedron Letters, 2005, 46, 2025, which are incorporated herein by reference in their entireties). In a typical procedure, an equimolar mixture of amine (III), glyoxylic acid (V) and boronic acid (VI) were dissolved in a suitable solvent (e.g. dichloromethane, acetonitrile) and stirred. This reaction is usually performed in a temperature range of about 0° C. to about 110° C. over a period of about 1 hour to about 74 hours. The reaction may be conducted under conventional heating (using an oil bath) or under microwave heating. The reaction may be carried out in an open vessel or in a sealed tube.

Route C. Compounds of general formula (IX) might be prepared starting from the suitable aminoacid derivatives of general formula (VIII). These reagents can be converted into compounds of general formula (IX) using known protocols (e.g. Benasutti et al., Tetrahedron Asymmetry, 2006, 17/5, 842; Benson et al., J. O. C., 1988, 53/22, 5335; Cuevas et al., Synlett, 2007, 1, 119; and Juarez et al., Tetrahedron Asymmetry, 1997, 8/2, 203, which are incorporated herein by reference in their entireties). These protocols include, but are not limited to, reductive amination, amide formation or alkylation of aminoacid derivatives of formula (VIII) with reagents of general (VII), in which R1, A, K, m, and n are as defined above and Y could be an aldehyde group (CHO), a carboxylic acid (COOH), an acyl group (e.g. Y=COCl) or a suitable leaving group (an halide such as a bromide or a sulfonic ester group such as a mesilate).

Compounds of formula (IX) may be then converted into compounds of general formula (II) by coupling with compounds of general formula (X). This coupling may be conducted in several ways, in which K may be an alkoxy group, an hydroxyl group or an halogen such as chlorine (a survey of the suitable reactions is given by Carey, F. A. and Sundeberg, R. J. Advanced Organic Chemistry, Third Edition (1990), Plenum Press, New York and London, pg 145, which is incorporated herein by reference in its entirety).

In particular, in the case when K is a protected hydroxyl group such as an alkoxy group (e.g. K═OMe, OEt or OtBu), the ester (IX) could be either reacted with the opportune quinuclidin-3-ol salts or hydrolized to obtain the corresponding acid derivative (IX; K═OH).

In the first case, compounds of formula (II) are obtained reacting compounds of formula (IX), in which K is an alkoxy group (e.g. K═OMe), with quinuclidin-3-ol salts (X), in which J is Na, Li, or K. In a typical procedure, a solution of the esters (IX) and the opportune salts of quinuclidin-3-ol (previously performed or generated in situ) in a suitable solvent (e.g. toluene, DMF or NMP), is heated at temperature ranging from about 80° C. to about 200° C. over a period of about 1 hour to about 74 hours.

In the second case, hydrolysis of ester moiety in (IX) (e.g. K═OMe) may be performed treating these compounds with a suitable aqueous base selected from the group consisting of sodium, lithium, and potassium hydroxide in the opportune solvents (e.g. tetrahydrofuran, dioxane, water, etc). The reaction proceeds at room temperature (RT), over a period of 1 hour up to 36 hours. The resulting carboxylic acid could be coupled to quinuclidin-3-ol according to several protocols.

Alternative one. In a typical procedure, compounds (II) may be prepared by condensation between alcohol (X) (J═H) and acid (IX) (K═OH) under standard amidation and peptide coupling conditions. For instance, treatment of the acid (IX) with one or more equivalents of a commercially available condensing agent such as a carbodiimide (e.g. 1-(3-dimethylamino)propyl)-3-ethylcarbodiimide hydrochloride (EDC) and the like) for example in the presence of N-hydroxybenzotriazole (HOBt) followed by reaction of the activated intermediate with alcohol (X), results in the formation of compounds (II). An organic base such as triethylamine may be also present in the reaction mixture. The activated intermediate may be either isolated, or pre-formed or generated in situ. Suitable solvents for the coupling include, but are not limited to, halocarbon solvents (e.g. dichloromethane), tetrahydrofuran, dioxane, and acetonitrile. The reaction proceeds at temperature range from 0° C. up to 170° C., for a time in the range of about 1 hour up to 72 hours. The reaction may be carried out under conventional heating (using an oil bath) or under microwave irradiation. The reaction may be conducted either in an open vessel or in a sealed tube.

Alternative two. In the case where K is halogen such as chlorine, the alcohol (X) (J═H) is reacted with the suitable acyl halide (IX), using known procedures. The reaction may be promoted by a base such as triethylamine, pyridine and 4-dimethylaminopyridine, in a suitable solvent (e.g. dichloromethane). This reaction is performed in a temperature range from 0° C. to 130° C. over a period of 1 hour up to 74 hours. The reaction may be conducted under conventional heating (using an oil bath) or under microwave heating. The reaction may be carried out in an open vessel or in a sealed tube.

In some embodiments of the present invention, the needed acyl halide (IX) may be readily prepared from the corresponding acid (IX) (K═OH). This activation may be effected according to one of the standard procedures reported in the literature. For instance, treatment of acid (IX) (K═OH) with one or more equivalents of oxalyl chloride in the presence of a catalytic amount of dimethylformamide (DMF) in a halocarbon solvent, such as dichloromethane, at temperature ranging form 0° C. to 35° C., affords the required acyl chloride (IX) (K═Cl).

Alternative three. Alternatively, acylation of alcohol (X) (J═H) to give compounds of general formula (IX) may be accomplished using procedures which convert in situ the acid (IX) (K═OH) into the corresponding acyl halides. For example, alcohols (X) are reacted with acids (IX) (K═OH) in presence of triphenylphosphine and a halocarbon solvent such as carbon tetrachloride or dichloromethane, at about RT, in a maximum period of time of 16 hours (Lee, J. B. J. Am. Chem. Soc., 1966, 88, 3440, which is incorporated herein by reference in its entirety).

Alternative four. In another process for the preparation of the compounds of the present invention, acid (IX) (K═OH) may be activated with other commercially available activating agents such as bromotripyrrolidinophosphonium hexafluorophosphate (PyBrOP) or carbonylimidazole, in the suitable aprotic solvent (e.g. dichloromethane, tetrahydrofuran), at about RT. Subsequent reaction of the activated intermediate with alcohol (X) provides the desired compound of formula (II). The reaction may also require the use of an organic base such as diisopropylethylamine and usually proceeds at about RT.

Alternative five. In another process for the preparation of the compounds of the present invention, compounds (II) can be efficiently prepared by the condensation between acids (IX) (K═OH) and alcohol (X) (J═H) under typical Mitsunobu conditions (Kumara Swamy, K. C., Chem. Rev. 2009, 109, 2551-2651, which is incorporated herein by reference in its entirety). For example, acids (IX) and alcohol (X) are reacted in presence of a phosphine (e.g. triphenylphosphine) and an azadicarboxylate ester (e.g. diethyl azodicarboxylate or diisopropyl azodicarboxylate) in an aprotic solvent such as tetrahydrofuran. The reaction typically proceeds at temperature range from 0° C. up to 100° C., for a time in the range of about 30 minutes up to 72 hours.

Compounds of formula (II), in which R1, A, m, and n are defined hereinbefore, can be achieved either as single diastereoisomer or as a mixture of diastereoisomers. The quinuclidin-3-ol can feature either a R or a S configuration. If the R-enantiomer is used, compound (II) can be obtained in the S—R configuration, in the R—R configuration or as a mixture of diasteroisomers (R—R and S—R configuration).

When a mixture of diastereoisomers is achieved, it may be converted to compounds of formula (I) of Scheme 1 or can be most conveniently resolved to give the two single diasteroisomers, which in turn may be converted to compounds of formula (I) of Scheme 1. This separation can be accomplished using known procedures. These procedures include, but are not limited to, chromatography purification, preparative HPLC purification and crystallization. For example, the two diastereoisomers can be separated by flash chromatography on silica gel eluting with suitable solvents or mixture of solvents such as DCM and Methanol and the like. In another process of the present invention separation of distereoisomers may be obtained using a column filled with a chiral stationary phase, for example Chiralpack AY or Chiralcel OD or Chiralcel OZ, and eluting, for example, with acetonitrile and/or with mixtures of acetonitrile and an alcohol. Alternatively the separation of diasteroisomers may be most conveniently achieved by crystallization from an opportune solvent (e.g. ethyl ether), as a free base or after the formation of a suitable salt (e.g. (+)-tartaric acid)).

The alkylation of compounds of formula (II):

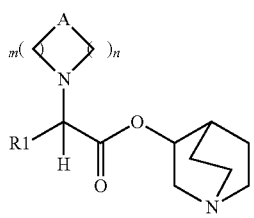

by alkylating agents of formula (XI):

in which X is a suitable leaving group selected from the group consisting of halide (i.e. bromine, iodine, chlorine) and sulfonate ester (i.e. tosylate, triflates, mesylate) provides compounds of general formula (I).

This kind of reaction is largely described in the literature under several different conditions, for instance, the reaction may be performed neat or in a suitable solvent selected from the group consisting of acetonitrile, DMF, DMSO, and tetrahydrofuran. The reaction typically proceeds at temperature range of from 0° C. up to 170° C., for a time in the range of few minutes up to 72 hours. The reaction may be carried out under conventional heating (using an oil bath) or under microwave irradiation. The reaction may be conducted either in an open vessel or in a sealed tube.

A compound of formula (I) and (II) in Scheme 1 can be either considered as a final product or as an intermediate to prepare other compounds of general formula (I) and (II). Thus, a moiety of R1, R2, or A group in general formula (I) and (II) could undergo reactions of oxidation, reduction or cleavage (e.g. to remove a protecting group) to afford other final compounds of general formula (I) and (II).

From the above, it should be clear to the skilled person that any of the described groups may be present as such or in any properly protected form. In particular, functional groups present in the intermediate and compounds and which could generate unwanted side reaction and by-products, may need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1981), which is incorporated herein by reference in its entirety).

Likewise, selective protection and deprotection of any of the said groups, for instance including carbonyl, hydroxyl or amino groups, may be accomplished according to very well known methods commonly employed in organic synthetic chemistry.

The present invention also provides pharmaceutical compositions of a compound of formula (I) or (II) in admixture with one or more pharmaceutically acceptable carrier or excipient, for example those described in Remington's Pharmaceutical Sciences Handbook, XVII Ed., Mack Pub., N.Y., U.S.A., which is incorporated herein by reference in its entirety.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the present invention including such solid forms as tablets, gelcaps, capsules, caplets, granules, lozenges, and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants, and the like. Time release capsules, tablets and gels are also advantageous in administering the compounds of the present invention.

Various liquid oral dosage forms can also be used for administering compounds of the present invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols.

Formulations for vaginal administration can be in the form of a cream, gel, paste, foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the present invention are preferably administered by inhalation. Inhalable preparations include powders for inhalation, propellant-driven pressurized metered dose aerosol inhalers, or propellant-free nebulised formulations.

For administration as a dry powder, single- or multi-dose inhalers known from the prior art may be utilized. In that case, the compound of the present invention in powder form may be filled in gelatine, plastic or other capsules, cartridges or blister packs or in a reservoir.

A diluent or carrier, generally non-toxic and chemically inert to the compound of the invention, e.g. lactose or any other additive suitable for improving the respirable fraction may be added to the powdered compound of the invention.

Propellant-driven pressurized metered dose aerosol inhalers contain the compound of the present invention either in solution or in dispersed form in at least a propellant gas such as a hydrofluoroalkane. The propellant-driven formulations may also contain other ingredients such as co-solvents, stabilizers and optionally other excipients.

The propellant-free inhalable formulations comprising the compound of the present invention may be in form of solutions or suspensions in an aqueous, alcoholic, or hydroalcoholic medium, and they may be delivered by jet or ultrasonic nebulizers or by soft-mist nebulizers.

The compounds of the present invention may be administered as the sole active agent or in combination with one or more pharmaceutical active ingredients currently used in the treatment of obstructive, inflammatory respiratory disorders, selected from the classes of beta2-agonists, corticosteroids and anticholinergic or antimuscarinic agents.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) and (II) can be administered for example, at a dosage of 0.001 to 1000 mg/day, preferably 0.1 to 500 mg/day.

When the compounds of formula (I) and (II) are administered by inhalation route, they are preferably given at a dosage of 0.001 to 500 mg/day, more preferably 0.1 to 200 mg/day.

The compounds of formula (I) and (II) may be administered for the prevention and/or treatment of any disease wherein M3 antagonists are active. Said disease include: diseases involving inflammation such as asthma and COPD, acute rhinitis; diseases involving the gastrointestinal tract such as peptic ulcer; diseases involving the cardiovascular system such as acute myocardial infarction; diseases involving the genitourinary tract such as renal colic; anticholinesterase and mushroom poisoning; uses in anesthesia; uses in ophthalmology. They also include neurological and psychiatric disorders such as Parkinsonism and motion sickness.

Preferably the compounds of formula (I) and (II) may be used for the prevention and/or treatment of respiratory diseases such as from mild to acute severe conditions of asthma and COPD.

Other respiratory diseases include bronchitis, bronchiolitis, bronchiectasis, acute nasoparyngitis, acute and chronic sinusitis, maxillary sinusitis, pharyngitis, tonsillitis, laryngitis, tracheitis, epiglottitis, croup, chronic disease of tonsils and adenoids, hypertrophy of tonsils and adenoids, peritonsillar abscess, rhinitis, abscess or ulcer and nose, pneumonia, viral and bacterial pneumonia, bronchopneumonia, influenza, extrinsic allergic alveolitis, coal workers' pneumoconiosis, asbestosis, pneumoconiosis, pneumonopathy, respiratory conditions due to chemical fumes, vapors and other external agents, emphysema, pleurisy, pneumothorax, abscess of lung and mediastinum, pulmonary congestion and hypostasis, postinflammatory pulmonary fibrosis, other alveolar and parietoalveolar pneumonopathy, idiopathic fibrosing alveolitis, Hamman-Rich syndrome, atelectasis, ARDS, acute respiratory failure, mediastinitis.

Other features of the invention will become apparent in the course of the following descriptions of exemplary embodiments which are given for illustration of the invention and are not intended to be limiting thereof.

EXAMPLES

In the following examples,
I=intermediates
C=compounds.

Example 1

Preparation of (3R)-1-(2-oxo-2-phenylethyl)-3-(2-phenyl-2-(piperidin-1-yl)acetoxy)-1-azonia bicyclo [2.2.2]octane bromide (C4)

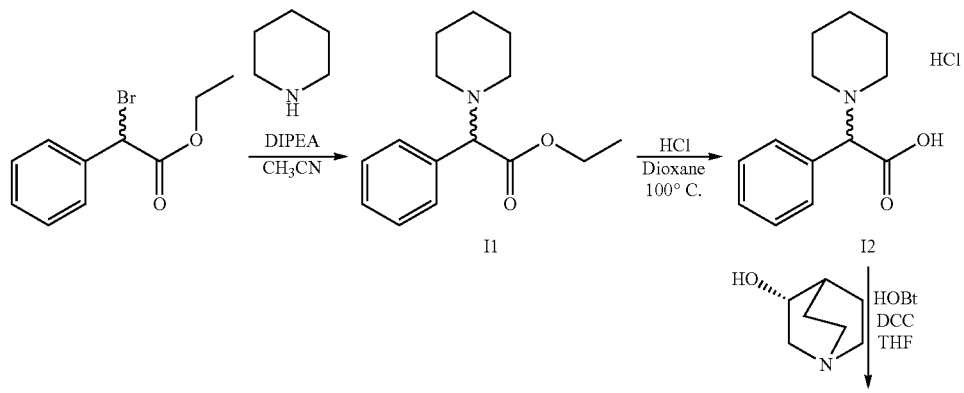

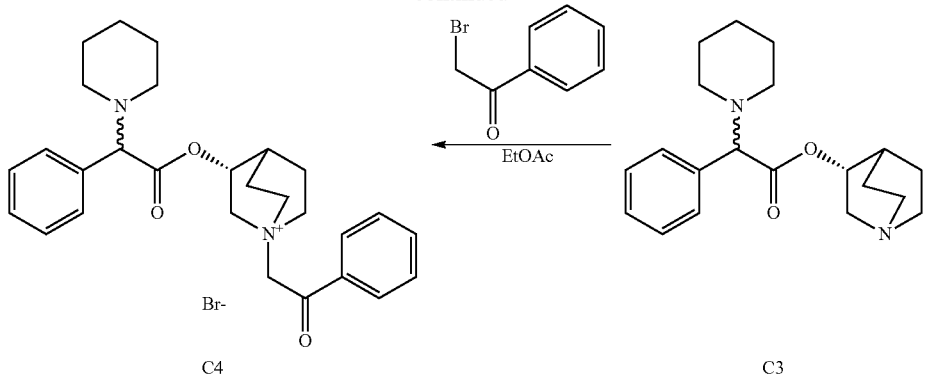

Preparation of ethyl 2-phenyl-2-(piperidin-1-yl)acetate (I1)

DIPEA (0.86 ml, 4.94 mmol) and piperidine (0.49 ml, 4.94 mmol) were sequentially added to a solution of ethyl 2-bromo-2-phenylacetate (0.72 ml, 4.11 mmol) in acetonitrile (13 ml). The pale yellow solution was stirred at room temperature monitoring by TLC (petroleum ether/EtOAc=9/1). After 1.5 hours complete conversion into the desired product was detected. Solvent was evaporated and the residue (pale yellow solid) was triturated with $Et_2O$ (30 ml). The solid was filtered off and the ethereal solution was evaporated to dryness. The residue was purified by flash chromatography (petroleum ether/EtOAc=95/5) to collect ethyl 2-phenyl-2-(piperidin-1-yl)acetate (990 mg, 97% yield) as a colorless oil.

$^1$H NMR (300 MHz, DMSO-$d_6$) ppm 7.03-7.54 (m, 5H), 4.05 (s, 1H), 3.93-4.20 (m, 2H), 2.23-2.45 (m, 4H), 1.29-1.59 (m, 6H), 1.13 (t, 3H).

Preparation of 2-phenyl-2-(piperidin-1-yl)acetic acid hydrochloride (I2)

Ethyl 2-phenyl-2-(piperidin-1-yl)acetate (985 mg, 3.98 mmol) was dissolved in dioxane (33 ml) and 37% HCl (10 ml) was slowly added. The reaction was refluxed for 48 hours and then it was evaporated under reduced pressure. The residue was triturated with acetonitrile (15 ml) and the solid was collected by filtration to obtain 2-phenyl-2-(piperidin-1-yl)acetic acid hydrochloride (876 mg, 86% yield) as a off-white solid. $^1$H NMR (300 MHz, DMSO-$d_6$) ppm 10.57 (br. s., 1H), 7.33-7.67 (m, 5H), 5.27 (s, 1H), 2.84-3.21 (m, 4H), 1.64-1.98 (m, 4H), 1.31-1.64 (m, 2H)

Preparation of (R)-quinuclidin-3-yl 2-phenyl-2-(piperidin-1-yl)acetate (C3)

2-Phenyl-2-(piperidin-1-yl)acetic acid hydrochloride (0.87 g, 3.40 mmol) was suspended in dry THF (34.0 ml) and, while stirring at room temperature, DCC (1.40 g, 6.80 mmol), HOBT (1.04 g, 6.80 mmol) and (R)-quinuclidin-3-ol (1.30 g, 10.21 mmol) were sequentially added. The white suspension was stirred at the same temperature overnight (UPLC-MS: complete conversion). THF was evaporated and the residue was taken up with EtOAc (30 ml) and washed with water (20 ml) and then with a sat. NaHCO3 (20 ml). The organic phase was dried over $Na_2SO_4$, filtered was evaporated. The crude was purified by flash chromatography (DCM/MeOH/NH4OH=98/2/0.2 to 97/3/0.3) to obtain (R)-quinuclidin-3-yl 2-phenyl-2-(piperidin-1-yl)acetate (40 mg, 40% yield) as a colorless oil.

$^1$H NMR (300 MHz, DMSO-$d_6$) ppm 7.26-7.44 (m, 5H) 4.64-4.77 (m, 1H) 4.07 (s, 1H) 2.97-3.15 (m, 1H) 2.55-2.71 (m, 3H) 2.40-2.48 (m, 2H) 2.31-2.40 (m, 4H) 1.71-1.95 (m, 1H) 1.33-1.63 (m, 9 μl) 1.18-1.32 (m, 1H).

Preparation of (3R)-1-(2-oxo-2-phenylethyl)-3-(2-phenyl-2-(piperidin-1-yl)acetoxy)-1-azonia bicyclo[2.2.2]octane bromide (C4)

2-Bromo-1-phenylethanone (91.0 mg, 0.46 mmol) was added to a solution of (R)-quinuclidin-3-yl 2-phenyl-2-(piperidin-1-yl)acetate (150 mg, 0.46 mmol) in EtOAc (10 ml). The mixture was stirred at room temperature for 3 hours. The precipitate was collected by suction filtration to obtain (3R)-1-(2-oxo-2-phenylethyl)-3-(2-phenyl-2-(piperidin-1-yl)acetoxy)-1-azoniabicyclo[2.2.2]octane bromide (191.7 g, 80% yield) as a white solid.

$^1$H NMR (300 MHz, DMSO-$d_6$) ppm 7.90-8.06 (m, 2H), 7.70-7.83 (m, 1H), 7.51-7.69 (m, 2H), 7.23-7.51 (m, 5 μl), 5.21 and 5.22 (s, 1H), 5.04-5.36 (m, 2 μl), 4.21 and 4.23 (s, 1H), 4.05-4.19 (m, 1H), 3.47-3.83 (m, 5H), 2.31-2.45 (m, 4H), 2.17-2.31 and 2.30-2.38 (m, 1H), 1.97-2.15 (m, 2H), 1.68-1.97 (m, 2H), 1.46-1.59 (m, 4H), 1.33-1.46 (m, 2H).

$^{13}$C NMR (75 MHz, DMSO-$d_6$) ppm 191.59 (s, 1C), 171.05 (s, 1C), 136.36 (s, 1C), 135.17 (s, 1C), 134.93 (s, 1C), 129.45 (s, 2C), 128.98 (s, 4C), 128.63 and 128.69 (s, 1C), 128.49 (s, 2C), 73.48 and 73.66 (s, 1C), 68.10 and 68.25 (s, 1C), 65.59 (s, 1C), 60.48 and 60.63 (br. s., 1C), 55.22 (s, 1C), 54.96 (s, 1C), 51.76 and 51.86 (s, 2C), 26.06 (s, 2C), 24.44 (s, 1C), 23.70 and 23.82 (s, 1C), 20.79 (s, 1C), 18.11 and 18.27 (s, 1C).

UPLC-MS (ESI POS): 447.13 (M+).

Example 2

Preparation of (3R)-1-(2-oxo-2-(thiophen-2-yl)ethyl)-3-(2-phenyl-2-(piperidin-1-yl)acetoxy)-1-azonia-bicyclo[2.2.2]octane trifluoroacetate trifluoroacetate anion (C5)

Scheme 3

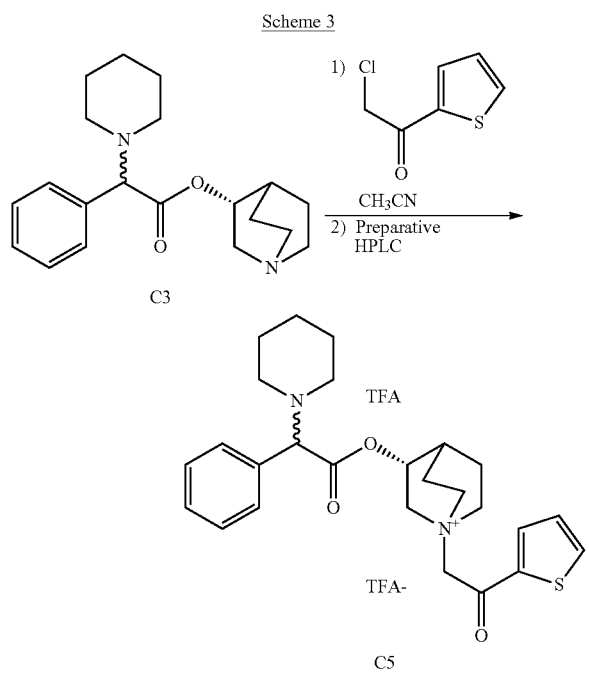

2-Chloro-1-(thiophen-2-yl)ethanone (32 mg, 0.22 mmol) was added to a solution of (R)-quinuclidin-3-yl 2-phenyl-2-(piperidin-1-yl)acetate (60 mg, 0.18 mmol) in acetonitrile (2 ml). The reaction was stirred at room temperature overnight (UPLC-MS: complete conversion). The crude was purified by preparative HPLC-MS to obtain (3R)-1-(2-oxo-2-(thiophen-2-yl)ethyl)-3-(2-phenyl-2-(piperidin-1-yl)acetoxy)-1-azonia-bicyclo[2.2.2]octane trifluoroacetate trifluoroacetate anion (43.3 mg, 35% yield) as a colorless oil.

$^1$H NMR (400 MHz, DMSO-d6) ppm 8.15-8.25 (m, 1H), 7.99-8.09 (m, 1H), 7.46-7.66 (m, 5H), 7.27-7.41 (m, 1H), 5.28-5.41 (m, 1H), 4.92-5.12 (m, 3H), 4.00-4.23 (m, 1H), 3.20-3.92 (m, 5H), 2.70-3.14 (m, 4H), 1.52-2.46 (m, 11H);

UPLC-MS (ESI POS) 453.25 (M+).

Example 3

Preparation of (3R)-1-(2-(4-chlorophenyl)-2-oxoethyl)-3-(2-phenyl-2-(piperidin-1-yl)acetoxy)-1-azoniabicyclo[2.2.2]octane bromide (C6)

Scheme 4

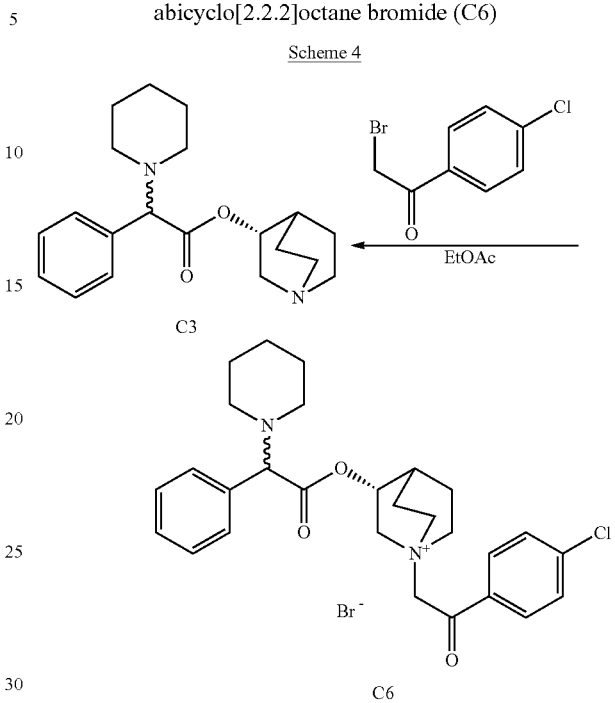

2-Bromo-1-(4-chlorophenyl)ethanone (49.8 mg, 0.21 mmol) was added to a solution of (R)-quinuclidin-3-yl 2-phenyl-2-(piperidin-1-yl)acetate (70 mg, 0.21 mmol) in ethyl acetate (2 ml). The reaction was stirred at room temperature overnight (UPLC-MS: complete conversion). Et$_2$O (1 ml) was added and the white precipitate was collected by suction filtration and dried under vacuum to obtain (3R)-1-(2-(4-chlorophenyl)-2-oxoethyl)-3-(2-phenyl-2-(piperidin-1-yl)acetoxy)-1-azoniabicyclo[2.2.2]octane bromide (93.5 mg, 78% yield) as a white solid.

$^1$H NMR (300 MHz, DMSO-d6) ppm 7.85-8.06 (m, 2H), 7.62-7.77 (m, 2H), 7.29-7.52 (m, 5H), 5.22 (d, 1H), 5.17 and 5.18 (s, 2H), 4.20 and 4.23 (s, 1H), 4.05-4.18 (m, 1H), 3.51-3.81 (m, 5H), 2.19-2.47 (m, 5H), 1.69-2.15 (m, 4H), 1.31-1.63 (m, 6H).

UPLC-MS (ESI POS) 481.31 (M+).

The compounds listed in Table 1 were obtained as previously described for C6, by alkylation of C3 with the suitable commercially available alkyl bromide.

TABLE 1

| Compound | Structure | Yield | Analytical |
|---|---|---|---|
| C7 | 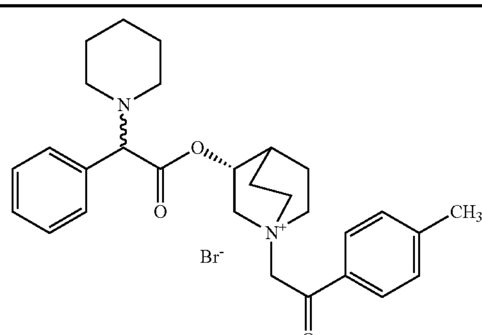 | 77% | LC-MS (ESI POS): 461.44 (MH$^+$)<br>$^1$H NMR (300 MHz, DMSO-d$_6$) ppm 7.77-7.94 (m, 2 H), 7.29-7.57 (m, 7 H), 5.18-5.26 (m, 1 H), 5.15 (s, 2 H), 4.20 and 4.22 (s, 1 H), 4.01-4.18 (m, 1 H), 3.55-3.80 (m, 5 H), 2.42 (s, 3 H), 2.16-2.41 (m, 5 H), 1.65-2.13 (m, 4 H), 1.29-1.63 (m, 6 H). |

TABLE 1-continued

| Compound | Structure | Yield | Analytical |
|---|---|---|---|
| C8 | 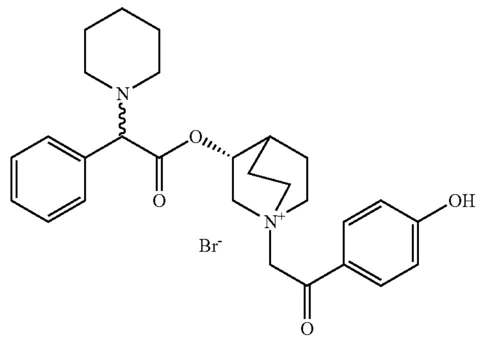 [SMILES: O=C(C[N+]12CCC(CC1)[C@@H](OC(=O)C(c1ccccc1)N1CCCCC1)C2)c1ccc(O)cc1 ; [Br-]] | 64.2% | LC-MS (ESI POS): 463.43 (MH⁺)<br>$^1$H NMR (300 MHz, DMSO-$d_6$) ppm 10.70 (s, 1 H), 7.78-7.96 (m, 2 H), 7.20-7.51 (m, 5 H), 6.77-7.03 (m, 2 H), 5.14-5.26 (m, 1 H), 5.08 (s, 2 H), 4.20 and 4.22 (s, 1 H), 3.94-4.18 (m, 1 H), 3.49-3.79 (m, 5 H), 2.18-2.44 (m, 5 H), 1.68-2.08 (m, 4 H), 1.30-1.56 (m, 6 H). |
| C9 | 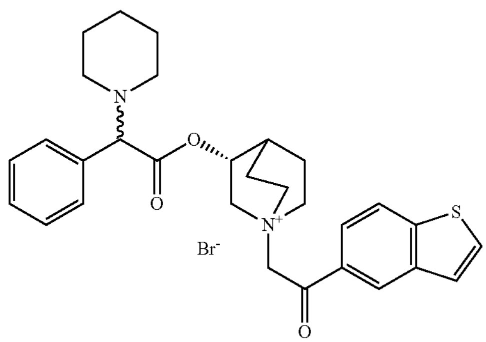 [SMILES: O=C(C[N+]12CCC(CC1)[C@@H](OC(=O)C(c1ccccc1)N1CCCCC1)C2)c1ccc2sccc2c1 ; [Br-]] | 81% | LC-MS (ESI POS): 503.41 (MH⁺)<br>$^1$H NMR (300 MHz, DMSO-$d_6$) ppm 8.53-8.65 (m, 1 H), 8.25 (d, 1 H), 7.97 (d, 1 H), 7.89-7.94 (m, 1 H), 7.67 (d, 1 H), 7.23-7.48 (m, 5 H), 5.29 (s, 2 H), 5.15-5.27 (m, 1 H), 4.22 and 4.24 (s, 1 H), 4.02-4.19 (m, 1 H), 3.52-3.85 (m, 5 H), 2.17-2.46 (m, 5 H), 1.75-2.17 (m, 4 H), 1.35-1.58 (m, 6 H). |
| C10 | 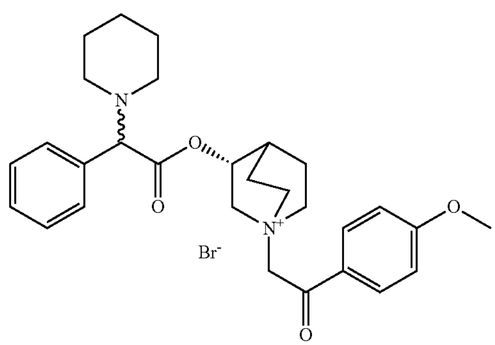 [SMILES: COc1ccc(C(=O)C[N+]23CCC(CC2)[C@@H](OC(=O)C(c2ccccc2)N2CCCCC2)C3)cc1 ; [Br-]] | 67.4% | LC-MS (ESI POS): 477.41 (MH⁺)<br>$^1$H NMR (300 MHz, Chloroform-d) ppm 8.02-8.21 (m, 2 H), 7.43-7.52 (m, 2 H), 7.32-7.42 (m, 3 H), 6.83-6.98 (m, 2 H), 5.71 snd 5.75 (d, 1 H), 5.52 and 5.65 (d, 1 H), 5.07-5.31 (m, 1 H), 4.50-4.68 (m, 1 H), 4.09-4.41 (m, 3 H), 4.08 (s, 1 H), 3.91-4.06 (m, 1 H), 3.85 (s, 3 H), 3.59-3.77 (m, 1 H), 2.30-2.56 (m, 5 H), 1.90-2.20 (m, 4 H), 1.38-1.87 (m, 6 H). |
| C11 | 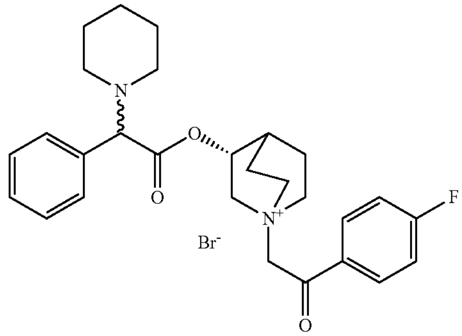 [SMILES: O=C(C[N+]12CCC(CC1)[C@@H](OC(=O)C(c1ccccc1)N1CCCCC1)C2)c1ccc(F)cc1 ; [Br-]] | 25.7% | LC-MS (ESI POS): 465.30 (MH⁺)<br>$^1$H NMR (300 MHz, DMSO-$d_6$) ppm 7.93-8.17 (m, 2 H), 7.22-7.62 (m, 7 H), 5.21-5.28 (m, 1 H), 5.19 and 5.20 (s, 2 H), 4.21 and 4.23 (s, 1 H), 4.05-4.17 (m, 1 H), 3.45-3.82 (m, 5 H), 2.19-2.44 (m, 5 H), 1.69-2.12 (m, 4 H), 1.30-1.58 (m, 6 H). |

TABLE 1-continued

| Compound | Structure | Yield | Analytical |
|---|---|---|---|
| C12 | 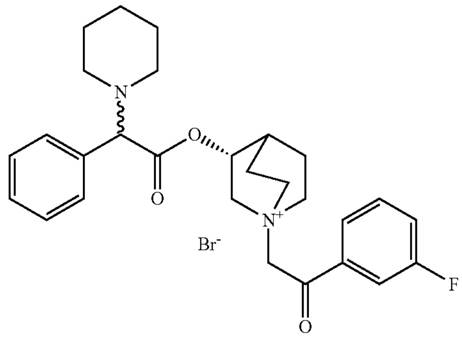 [SMILES: O=C(C[N+]12CCC(CC1)[C@@H](OC(=O)C(c1ccccc1)N1CCCCC1)C2)c1cccc(F)c1 ; [Br-]] | 57.3% | LC-MS (ESI POS): 465.28 (MH$^+$)<br>$^1$H NMR (300 MHz, DMSO-d$_6$) ppm 7.74-7.95 (m, 2 H), 7.57-7.74 (m, 2 H), 7.19-7.51 (m, 5 H), 5.22-5.27 (m, 1 H), 5.20 and 5.21 (br. s., 2 H), 4.21 and 4.23 (s, 1 H), 4.00-4.19 (m, 1 H), 3.45-3.81 (m, 5 H), 2.31-2.46 (m, 4 H), 2.18-2.31 (m, 1 H), 1.66-2.11 (m, 4 H), 0.95-1.65 (m, 6 H). |
| C13 | 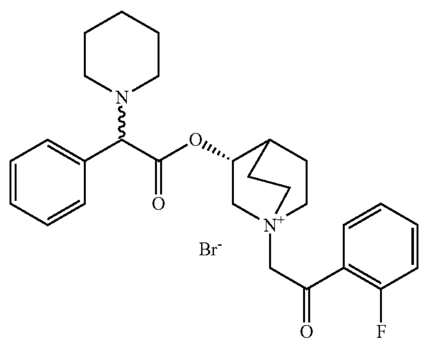 [SMILES: O=C(C[N+]12CCC(CC1)[C@@H](OC(=O)C(c1ccccc1)N1CCCCC1)C2)c1ccccc1F ; [Br-]] | 60.2% | LC-MS (ESI POS): 465.27 (MH$^+$)<br>$^1$H NMR (300 MHz, DMSO-d$_6$) ppm 7.89-8.07 (m, 1 H), 7.72-7.89 (m, 1 H), 7.20-7.56 (m, 7 H), 5.15-5.33 (m, 1 H), 4.89-5.11 (m, 2 H), 4.21 and 4.23 (s, 0 H), 4.05-4.20 (m, 1 H), 3.53-3.78 (m, 5 H), 2.29-2.45 (m, 5 H), 2.18-2.29 (m, 1 H), 1.70-2.10 (m, 4 H), 1.22-1.60 (m, 6 H). |
| C14 | 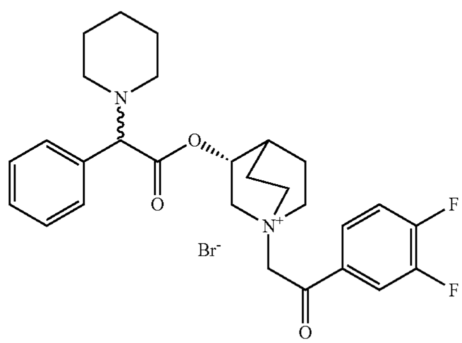 [SMILES: O=C(C[N+]12CCC(CC1)[C@@H](OC(=O)C(c1ccccc1)N1CCCCC1)C2)c1ccc(F)c(F)c1 ; [Br-]] | 25.6% | LC-MS (ESI POS): 483.24 (MH$^+$)<br>$^1$H NMR (300 MHz, DMSO-d$_6$) ppm 7.99-8.20 (m, 1 H), 7.84-7.96 (m, 1 H), 7.66-7.80 (m, 1 H), 7.26-7.48 (m, 5 H), 5.22 (dd, 1 H), 5.16 (s, 2 H), 4.20 (s, 1 H), 4.03-4.17 (m, 1 H), 3.48-3.78 (m, 5 H), 2.16-2.45 (m, 5 H), 1.65-2.16 (m, 4 H), 1.23-1.62 (m, 6 H) |
| C15 | 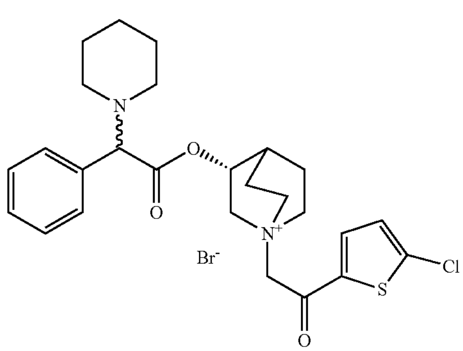 [SMILES: O=C(C[N+]12CCC(CC1)[C@@H](OC(=O)C(c1ccccc1)N1CCCCC1)C2)c1ccc(Cl)s1 ; [Br-]] | 99% | LC-MS (ESI POS): 487.27 (MH$^+$)<br>$^1$H NMR (300 MHz, DMSO-d$_6$) ppm 8.01 and 8.02 (d, 1 H), 7.43 and 7.44 (d, 1 H), 7.28-7.42 (m, 5 H), 5.14-5.26 (m, 1 H), 5.06 (s, 2 H), 4.19 and 4.22 (s, 1 H), 4.05-4.16 (m, 1 H), 3.47-3.81 (m, 5 H), 2.11-2.44 (m, 5 H), 1.63-2.11 (m, 4 H), 1.26-1.55 (m, 6 H). |

Example 4

Preparation of (3R)-1-(2-tert-butoxy-2-oxoethyl)-3-(2-phenyl-2-(piperidin-1-yl)acetoxy)-1-azoniabicyclo[2.2.2]octane bromide (C 16)

Scheme 5

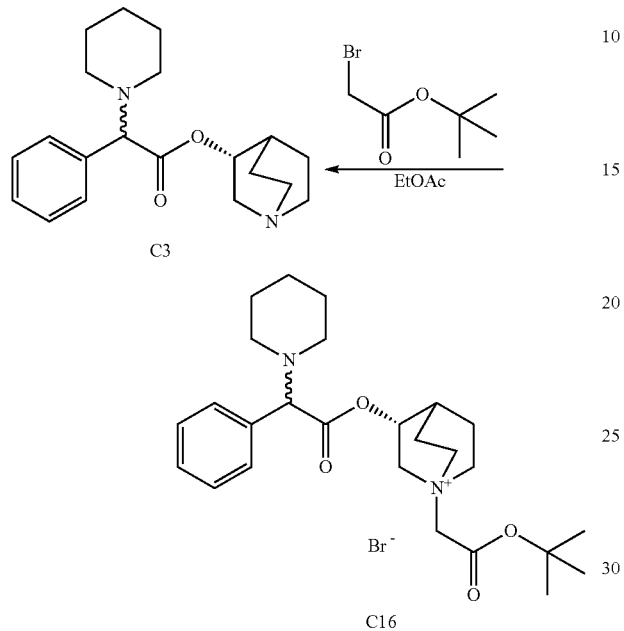

(R)-Quinuclidin-3-yl 2-phenyl-2-(piperidin-1-yl)acetate (120 mg, 0.36 mmol) was dissolved in ethyl acetate (3.65 ml) and 2-bromo-1-(thiazol-2-yl)ethanone (83 mg, 0.42 mmol) was added. The mixture was stirred at room temperature for 16 hours. The solvent was evaporated and the residue was purified by flash chromatography (DCM/MeOH=95/5 to 9/1) to obtain (3R)-1-(2-oxo-2-(thiazol-2-yl)ethyl)-3-(2-phenyl-2-(piperidin-1-yl)acetoxy)-1-azoniabicyclo[2.2.2]octane bromide (125 mg, 0.234 mmol, 64.0% yield) pale brown solid.

$^1$H NMR (300 MHz, DMSO-d6) ppm 7.19-7.53 (m, 5H), 5.05-5.25 (m, 1H), 4.25 and 4.27 (s, 2H), 4.17 and 4.20 (s, 1H), 3.90-4.12 (m, 1H), 3.39-3.72 (m, 5H), 2.15-2.45 (m, 5H), 1.65-2.08 (m, 4H), 1.47 (s, 9H), 1.35-1.59 (m, 6H);

UPLC-MS (ESI POS) 443.05 (M+).

The compounds listed in Table 2 were obtained as previously described for C16, by alkylation of C3 with the suitable commercially available alkyl bromide.

TABLE 2

| | | | |
|---|---|---|---|
| C17 | (structure) | 64% | LC-MS (ESI POS): 454.06 (MH$^+$)<br>$^1$H NMR (300 MHz, DMSO-d$_6$) ppm 8.39 (d, 1 H), 8.24 (d, 1 H), 7.13-7.54 (m, 5 H), 5.23 and 5.24 (s, 2 H), 5.13-5.22 (m, 1 H), 4.20 and 4.22 (s, 1 H), 4.04-4.18 (m, 1 H), 3.52-3.80 (m, 5 H), 2.36-2.44 (m, 4 H), 2.19-2.26 and 2.32-2.35 (m, 1 H), 1.63-2.10 (m, 4 H), 1.32-1.57 (m, 6 H). |
| C18 | (structure) | 64.7% | LC-MS (ESI POS): 510.26 (MH$^+$)<br>$^1$H NMR (300 MHz, DMSO-d$_6$) ppm 7.81-7.92 (m, 1 H) 7.25-7.48 (m, 5 H) 5.14-5.25 (m, 1 H) 5.00-5.11 (m, 2 H) 4.29-4.51 (m, 2 H) 4.00-4.27 (m, 2 H) 3.50-3.82 (m, 4 H) 2.82-3.15 (m, 1 H) 2.31-2.46 (m, 4 H) 2.19-2.31 (m, 1 H) 1.69-2.09 (m, 4 H) 1.45-1.60 (m, 4 H) 1.26-1.45 (m, 5 H). |

Example 5

Preparation of (3R)-1-(2-oxo-2-(thiophen-3-yl)ethyl)-3-(2-phenyl-2-(piperidin-1-yl)acetoxy)-1-azoniabicyclo[2.2.2]octane bromide (C 19)

Scheme 6

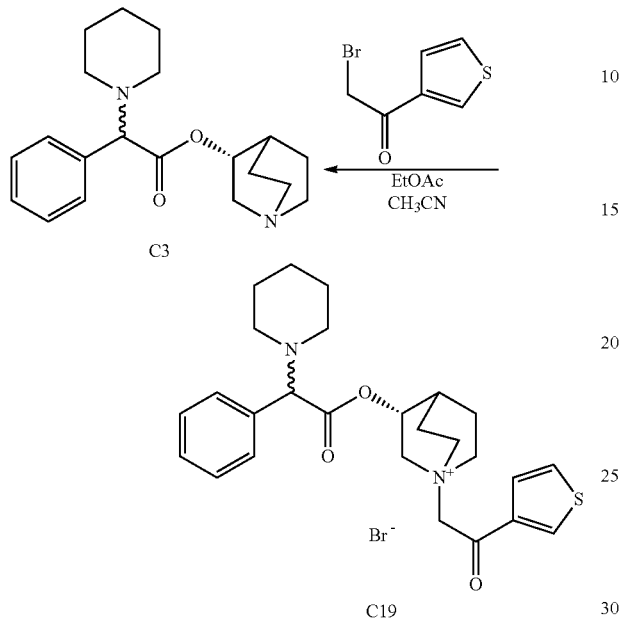

2-Bromo-1-(thiophen-3-yl)ethanone (54.9 mg, 0.27 mmol) was added to a solution of (R)-quinuclidin-3-yl 2-phenyl-2-(piperidin-1-yl)acetate (80 mg, 0.24 mmol) in ethyl acetate (1.2 ml) and acetonitrile (1.2 ml). The reaction was stirred at room temperature for 24 h (UPLC-MS: complete conversion). The solvents were evaporated and the residue was purified first by flash chromatography (DCM/MeOH=92/8) and then by trituration with $Et_2O$ to obtain compound (3R)-1-(2-oxo-2-(thiophen-3-yl)ethyl)-3-(2-phenyl-2-(piperidin-1-yl)acetoxy)-1-azoniabicyclo[2.2.2]octane bromide (96 mg, 73.9% yield) as a white solid.

$^1$H NMR (300 MHz, DMSO-d6) ppm 8.64 (dd, 1H) 7.74 (ddd, 1H) 7.56 (dd, 1H) 7.28-7.48 (m, 5H) 5.15-5.26 (m, 1H) 5.09 (s, 2H) 4.05-4.26 (m, 2H) 3.49-3.79 (m, 5H) 2.14-2.46 (m, 5H) 1.69-2.09 (m, 4H) 1.29-1.59 (m, 6H).

UPLC-MS (ESI POS) 453.32 (M+).

Example 6

Preparation of (3R)-1-((5-phenyl-1,2,4-oxadiazol-3-yl)methyl)-3-(2-phenyl-2-(piperidin-1-yl)acetoxy)-1-azoniabicyclo[2.2.2]octane chloride (C21)

Scheme 7

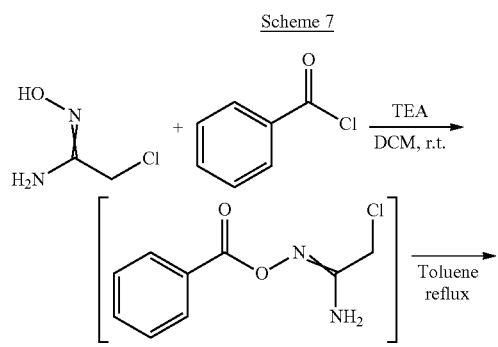

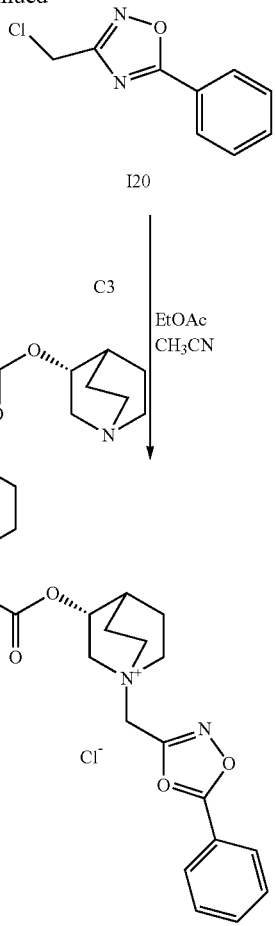

Preparation of 3-(chloromethyl)-5-phenyl-1,2,4-oxadiazole (I20)

Benzoyl chloride (1.60 ml, 13.8 mmol) was added to a suspension of 2-chloro-N'-hydroxyacetimidamide (1.0 g, 9.21 mmol) in DCM (25 ml), with stirring at room temperature. After 30 minutes, TEA (1.41 ml, 10.1 mmol) was added to the white suspension and the mixture was stirred for 30 additional minutes (UPLC-MS: complete conversion). The solution was diluted with DCM (20 ml) and water (30 ml) was added. The aqueous phase was extracted three times with DCM (15 ml×3) and then the combined organic phases were dried ($Na_2SO_4$) and evaporated. The crude was suspended in toluene (25 ml) and the mixture was heated to reflux for 6 h (UPLC-MS: complete conversion). The solvent was evaporated and the crude was purified by flash chromatography (petroleum ether/EtOAc=95/5) to obtain 3-(chloromethyl)-5-phenyl-1,2,4-oxadiazole (803 mg, 44.8% yield) as an off-white solid.

$^1$H NMR (300 MHz, DMSO-d6) ppm 8.06-8.20 (m, 2H), 7.69-7.79 (m, 1H), 7.57-7.69 (m, 2H), 4.96 (s, 2H).

Preparation of (3R)-1-((5-phenyl-1,2,4-oxadiazol-3-yl)methyl)-3-(2-phenyl-2-(piperidin-1-yl)acetoxy)-1-azoniabicyclo[2.2.2]octane chloride (C21)

To a solution of (R)-quinuclidin-3-yl 2-phenyl-2-(piperidin-1-yl)acetate (100 mg, 0.30 mmol) in EtOAc (2 ml) and acetonitrile (1 ml), was added 3-(chloromethyl)-5-phenyl-1,2,4-oxadiazole (71.1 mg, 0.36 mmol). The reaction was stirred at room temperature for 30 hours and then the solvents were evaporated. The residue was triturated with EtOAc (10 ml) and the solid was collected by suction filtration to obtain the title compound (113 mg, 71% yield) as a yellow solid.

$^1$H NMR (300 MHz, DMSO-d6) ppm 8.05-8.28 (m, 2H), 7.74-7.91 (m, 1H), 7.61-7.74 (m, 2H), 7.17-7.51 (m, 5H), 5.03-5.21 (m, 1H), 4.89 (s, 2H), 4.17 and 4.21 (s, 1H), 4.02-4.16 (m, 1H), 3.34-3.87 (m, 5H), 2.13-2.43 (m, 5H), 1.68-2.04 (m, 4H), 1.28-1.60 (m, 6H).

UPLC-MS (ESI POS) 487.11 (M+).

Example 7

Preparation of (3R)-3-(2-phenyl-2-(piperidin-1-yl)acetoxy)-1-((2-phenyloxazol-4-yl)methyl)-1-azoniabicyclo[2.2.2]octane chloride (C23)

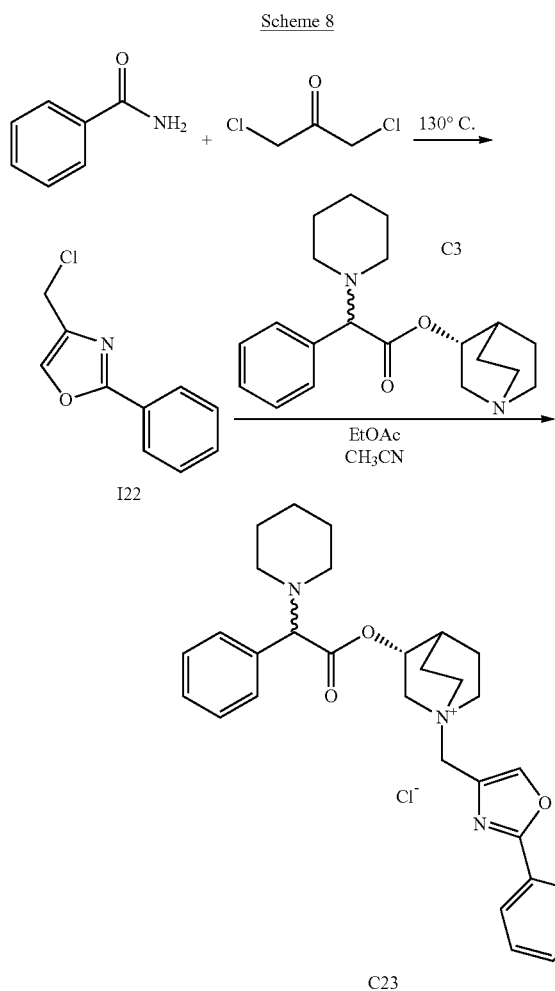

Preparation of 4-(Chloromethyl)-2-phenyloxazole (I22)

A mixture of benzamide (0.80 g, 6.60 mmol) and 1,3-dichloropropan-2-one (1.01 g, 7.92 mmol) was heated to 130° C. for 1 hour under nitrogen atmosphere. The crude was purified by crystallization from acetonitrile (25 ml): the suspension was heated to reflux and a brown solution with a white insoluble solid was obtained. It was filtered and the solution was cooled to room temperature. A precipitate formed and the suspension was filtered on a buckner funnel washing with acetonitrile (8 ml). The solid was recovered from the filter, dissolved in EtOAc (20 ml) and washed with 1N NaHCO$_3$ (15 ml). The organic phase was dried (Na$_2$SO$_4$) and evaporated to give 4-(chloromethyl)-2-phenyloxazole (315 mg, 25% yield) as a pale brown solid.

$^1$H NMR (300 MHz, DMSO-d6) ppm 8.27 (s, 1H), 7.89-8.09 (m, 2H), 7.39-7.68 (m, 3H), 4.74 (s, 2H).

Preparation of (3R)-3-(2-phenyl-2-(piperidin-1-yl)acetoxy)-1-((2-phenyloxazol-4-yl)methyl)-1-azoniabicyclo[2.2.2]octane chloride (C23)

To a solution of (R)-quinuclidin-3-yl 2-phenyl-2-(piperidin-1-yl)acetate (100 mg, 0.30 mmol) in EtOAc (2 ml) and acetonitrile (1 ml), was added 4-(chloromethyl)-2-phenyloxazole (70.7 mg, 0.36 mmol). The reaction was stirred at room temperature for 30 hours and then the solvents were evaporated. Purification by flash chromatography (DCM/MeOH=9/1) followed by trituration with Et$_2$O afforded (3R)-3-(2-phenyl-2-(piperidin-1-yl)acetoxy)-1-((2-phenyloxazol-4-yl)methyl)-1-azoniabicyclo[2.2.2]octane chloride (55 mg, 34.6% yield) as an off-white solid.

$^1$H NMR (300 MHz, DMSO-d6) ppm 8.46 and 8.47 (s, 1H), 7.95-8.09 (m, 2H), 7.52-7.67 (m, 3H), 7.21-7.40 (m, 5H), 4.97-5.26 (m, 1H), 4.43-4.74 (m, 2H), 4.15 and 4.17 (s, 1H), 3.88-4.01 (m, 1H), 3.13-3.72 (m, 5H), 2.24-2.42 (m, 4H), 2.12-2.21 and 2.26-2.36 (m, 1H), 1.68-2.02 (m, 4H), 1.28-1.55 (m, 6H).

UPLC-MS (ESI POS) 486.27 (M+).

Example 8

Preparation of (3R)-1-(2-(isoxazol-3-ylamino)-2-oxoethyl)-3-(2-phenyl-2-(piperidin-1-yl)acetoxy)-1-azoniabicyclo[2.2.2]octane chloride (C25).

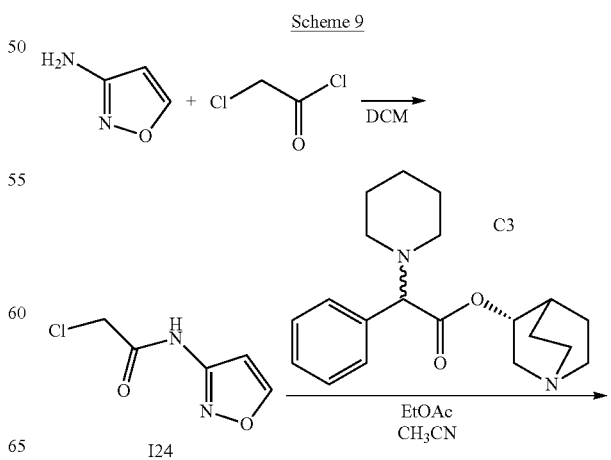

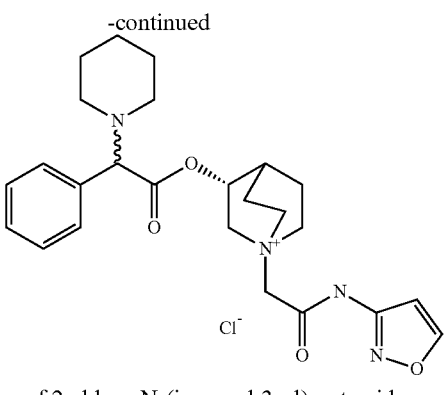

Preparation of 2-chloro-N-(isoxazol-3-yl)acetamide (I24) C25

2-Chloroacetyl chloride (0.21 ml, 2.66 mmol) was dissolved in DCM (10 ml) and the solution was cooled to 0° C. with an ice-bath. Isoxazol-3-amine (0.41 ml, 5.58 mmol) was added dropwise and a white suspension was obtained. The mixture was stirred at room temperature for 2 hours, then the suspension was evaporated and the residue was purified by flash chromatography (ether/EtOAc=8/2 to 7/3) to obtain 2-chloro-N-(isoxazol-3-yl)acetamide (367 mg, 86% yield) as an off-white solid.

$^1$H NMR (300 MHz, DMSO-d6) ppm 11.38 (br. s., 1H), 8.82 (d, 1H), 6.91 (d, 1H), 4.32 (s, 2H).

(3R)-1-(2-(isoxazol-3-ylamino)-2-oxoethyl)-3-(2-phenyl-2-(piperidin-1-yl)acetoxy)-1-azoniabicyclo[2.2.2]octane chloride (C25)

To a solution of (R)-quinuclidin-3-yl 2-phenyl-2-(piperidin-1-yl)acetate (100 mg, 0.30 mmol) in EtOAc (2 ml) and acetonitrile (1 ml), was added 2-chloro-N-(isoxazol-3-yl)acetamide (58.7 mg, 0.36 mmol). The reaction was stirred at room temperature for 30 hours and then the solvents were evaporated. Purification by flash chromatography (DCM/MeOH=9/1) followed by trituration with Et$_2$O afforded the title compound (55 mg, 36.9% yield) as an off-white solid.

$^1$H NMR (300 MHz, DMSO-d6) ppm 11.86 (br. s., 1H) 8.88 (d, 1H) 7.18-7.55 (m, 5H) 6.89 (d, 1H) 5.03-5.31 (m, 1H) 4.38 (d, 2H) 4.19 (s, 1H) 4.08-4.24 (m, 1H) 3.44-3.83 (m, 5H) 2.30-2.46 (m, 4H) 2.13-2.28 (m, 1H) 1.69-2.08 (m, 4H) 1.45-1.61 (m, 4H) 1.40 (m, 2H).

UPLC-MS (ESI POS) 453.15 (M+).

Example 9

Preparation of (3R)-1-(4-fluorophenethyl)-3-(2-phenyl-2-(piperidin-1-yl)acetoxy)-1-azoniabicyclo[2.2.2]octane 2,2,2-trifluoroacetate (C26)

Scheme 10

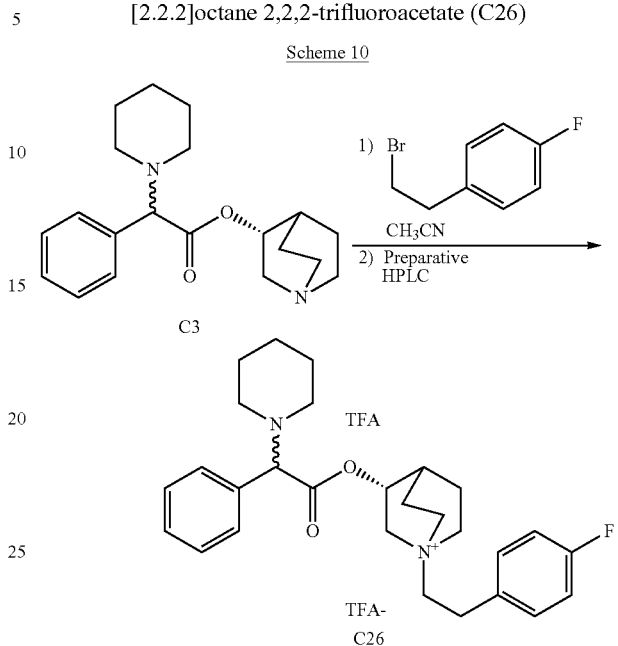

(R)-quinuclidin-3-yl 2-phenyl-2-(piperidin-1-yl)acetate (200 mg, 0.61 mmol) was dissolved in acetonitrile (3.1 ml) and 1-(2-bromoethyl)-4-fluorobenzene (0.17 ml, 1.22 mmol) was added. The reaction was heated at 100° C. for 1 hour under microwave irradiation. The solution was evaporated and the crude was purified first by flash chromatography (DCM/MeOH=9/1) and then by preparative HPLC to give the title compound (77 mg, 19% yield) as a pale yellow gummy solid.

$^1$H NMR (300 MHz, DMSO-d6) ppm 7.39-7.58 (m, 5H) 7.28-7.39 (m, 2H) 7.05-7.22 (m, 2H) 5.17-5.32 (m, 1H) 4.71 (br. s., 1H) 3.85-4.06 (m, 1H) 3.14-3.67 (m, 7H) 2.90-3.09 (m, 2H) 2.62-2.84 (m, 4H) 2.20 (d, 1H) 1.72-2.12 (m, 4H) 1.59-1.71 (m, 4H) 1.41-1.56 (m, 2H).

UPLC-MS (ESI POS) 451.25 (M+).

Example 10

Preparation of (3R)-3-(2-(4-methylpiperidin-1-yl)-2-phenylacetoxy)-1-(2-oxo-2-phenylethyl)-1-azoniabicyclo[2.2.2]octane bromide (C33)

Scheme 11

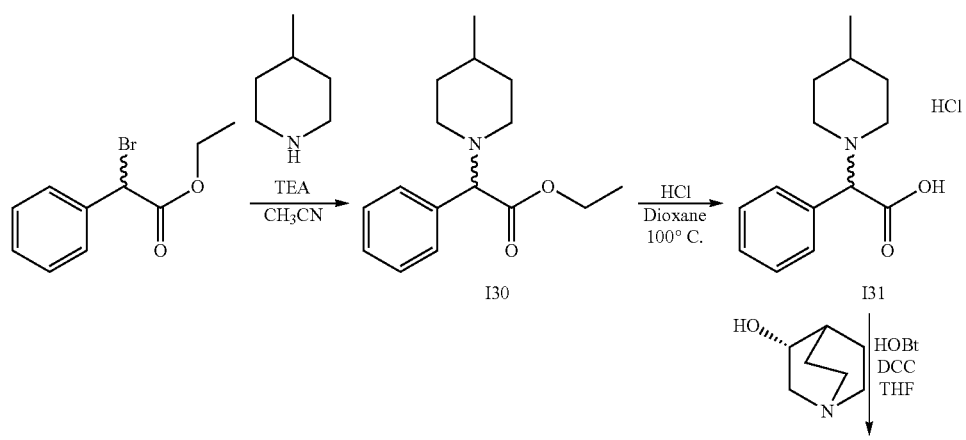

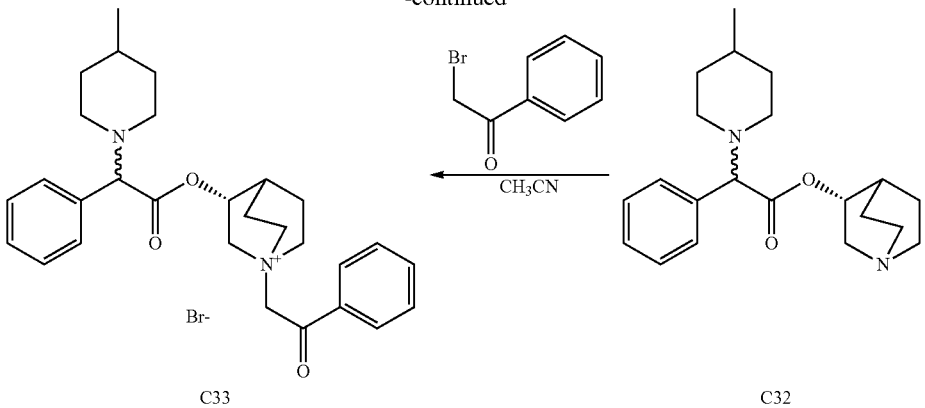

C33   C32

Preparation of ethyl 2-(4-methylpiperidin-1-yl)-2-phenylacetate (I30)

4-Methylpiperidine (0.17 ml, 1.48 mmol), ethyl 2-bromo-2-phenylacetate (0.22 ml, 1.23 mmol), and TEA (0.21 ml, 1.48 mmol) were dissolved in acetonitrile (6 ml) and stirred at room temperature for 48 hours. The volatiles were evaporated and the crude residue was purified by flash chromatography (petroleum ether/AcOEt=95/5) to obtain ethyl 2-(4-methylpiperidin-1-yl)-2-phenylacetate (225 mg, 69.8% yield) as a colourless oil.

UPLC-MS (ESI POS) 262.2 (M+).

Preparation of 2-(4-methylpiperidin-1-yl)-2-phenylacetic acid hydrochloride (I31)

Ethyl 2-(4-methylpiperidin-1-yl)-2-phenylacetate (225 mg, 0.86 mmol) and 37% aq HCl (0.52 ml, 17.2 mmol) were dissolved in Dioxane (7 ml) and heated under microwave irradiation into a sealed vial at 100° C. for 8 hours. The solvents were evaporated, the residue was suspended in EtOAc and evaporated. The residue was suspended in EtOAc/Et$_2$O (1/1), sonicated and filtered under suction to obtain 2-(4-methylpiperidin-1-yl)-2-phenylacetic acid hydrochloride (223 mg, 96% yield) as a white solid $^1$H NMR (300 MHz, DMSO-d6) ppm 10.29 (br. s., 1H), 7.27-7.80 (m, 5H), 5.21 (s, 1H), 2.79-3.17 (m, 4H), 1.66-1.91 (m, 2H), 1.39-1.66 (m, 3H), 0.92 (d, 3H).

Preparation of (R)-quinuclidin-3-yl 2-(4-methylpiperidin-1-yl)-2-phenylacetate (C32)

2-(4-Methylpiperidin-1-yl)-2-phenylacetic acid hydrochloride (105 mg, 0.39 mmol), HOBT (119 mg, 0.78 mmol), and DCC (161 mg, 0.78 mmol) were dissolved in dry THF (5 ml). (R)-quinuclidin-3-ol (149 mg, 1.17 mmol) was added and the reaction mixture was stirred at room temperature for 16 hours. THF was evaporated, the residue was dissolved in EtOAc and washed with sat. NaHCO$_3$, water and brine. The organic layer was dried over Na$_2$SO$_4$, filtered and evaporated. The crude was purified by flash chromatography (DCM/MeOH=9/1) to obtain (R)-quinuclidin-3-yl 2-(4-methylpiperidin-1-yl)-2-phenylacetate (58 mg, 43.5% yield).

Preparation of (3R)-3-(2-(4-methylpiperidin-1-yl)-2-phenylacetoxy)-1-(2-oxo-2-phenylethyl)-1-azoniabicyclo[2.2.2]octane bromide (C33)

(R)-Quinuclidin-3-yl 2-(4-methylpiperidin-1-yl)-2-phenylacetate (58 mg, 0.17 mmol) and 2-bromo-1-phenylethanone (37.1 mg, 0.19 mmol) were dissolved in acetonitrile (3 ml) and stirred at room temperature overnight. The solvent was evaporated and the residue was tritured with Et$_2$O and filtered under vacuum. The recovered solid was further purified by preparative HPLC to obtain (3R)-3-(2-(4-methylpiperidin-1-yl)-2-phenylacetoxy)-1-(2-oxo-2-phenylethyl)-1-azoniabicyclo[2.2.2]octane bromide (5 mg, 5.5% yield) as a colorless oil.

$^1$H NMR (300 MHz, DMSO-d$_6$) ppm 7.90-8.03 (m, 2H), 7.70-7.82 (m, 1H), 7.58-7.67 (m, 2H), 7.53 (br. s., 5H), 5.27-5.42 (m, 1H), 5.15 (s, 2H), 4.03-4.22 (m, 1H), 3.69-3.88 (m, 5H), 2.77-3.44 (m, 4H), 2.18-2.24 (m, 1H), 1.14-2.16 (m, 10H), 0.92 (d, 3H).

UPLC-MS (ESI POS) 461.08 (M+).

Example 11

Preparation of (3R)-1-(2-oxo-2-phenylethyl)-3-(2-phenyl-2-(pyrrolidin-1-yl)acetoxy)-1-azoniabicyclo[2.2.2]octane chloride (C37)

Scheme 12

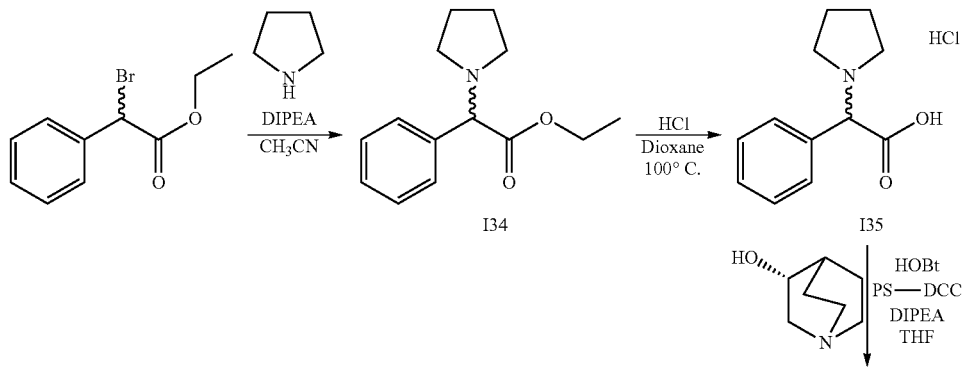

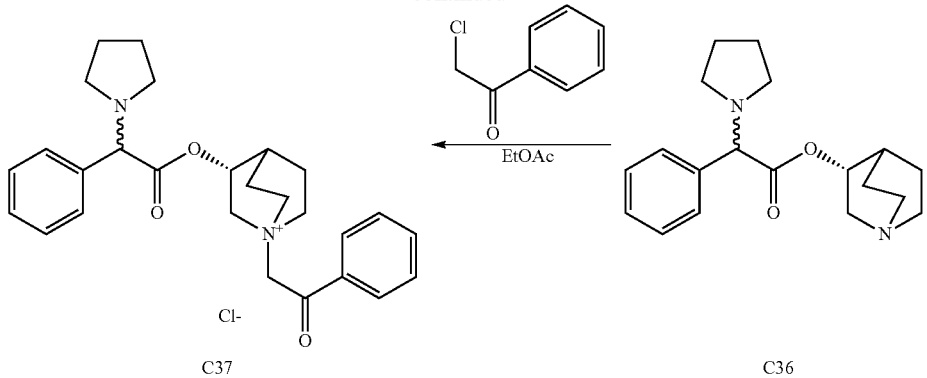

Preparation of ethyl 2-phenyl-2-(pyrrolidin-1-yl)acetate (I34)

Ethyl 2-bromo-2-phenylacetate (0.22 ml, 1.23 mmol) was dissolved in acetonitrile (4.0 ml). DIPEA (0.26 ml, 1.48 mmol) and pyrrolidine (0.12 ml, 1.48 mmol) were sequentially added and the solution was stirred at room temperature for 1.5 hours. Acetonitrile was evaporated and the residue was purified by flash chromatography (petroleum ether/EtOAc=9/1) to obtain ethyl 2-phenyl-2-(pyrrolidin-1-yl)acetate (315 mg, quantitative yield) as a colorless oil.

$^1$H NMR (300 MHz, DMSO-d6) ppm 7.39-7.47 (m, 2H), 7.26-7.39 (m, 3H), 4.09 (dq, 1H), 4.03 (dq, 1H), 3.98 (s, 1H), 2.24-2.48 (m, 4H), 1.58-1.82 (m, 4H), 1.11 (t, 3H).

Preparation of 2-phenyl-2-(pyrrolidin-1-yl)acetic acid hydrochloride (I35)

Ethyl 2-phenyl-2-(pyrrolidin-1-yl)acetate (0.31 g, 1.33 mmol) was dissolved in dioxane (11 ml) and 37% HCl (1.09 ml, 13.3 mmol) was added dropwise. The mixture was stirred at reflux overnight. Then 37% HCl (1.09 ml, 13.3 mmol) was added again and the reaction was refluxed for additional 24 hours. The solvent was evaporated, the residue was triturated with acetonitrile (10 ml) and the suspension was filtered on a buckner funnel. The solid was recovered to obtain 2-phenyl-2-(pyrrolidin-1-yl)acetic acid hydrochloride (0.25 g, 79% yield) as a white solid.

$^1$H NMR (300 MHz, DMSO-d6) ppm 11.12 (br. s., 1H), 7.56-7.71 (m, 2H), 7.38-7.55 (m, 3H), 5.30 (s, 1H), 3.19-3.65 (m, 2H), 2.88-3.19 (m, 2H), 1.73-2.09 (m, 4H).

Preparation of (R)-quinuclidin-3-yl 2-phenyl-2-(pyrrolidin-1-yl)acetate (C36)

PS-DCC (loading: 1.25 mmol/g; 0.99 g, 1.24 mmol) was suspended in dry THF (12 ml). HOBT (0.19 g, 1.24 mmol), 2-phenyl-2-(pyrrolidin-1-yl)acetic acid hydrochloride (0.15 g, 0.62 mmol) and (R)-quinuclidin-3-ol (0.24 g, 1.86 mmol) were sequentially added. The mixture was shaken overnight and then PS-DCC was filtered washing with EtOAc and THF. The solution was evaporated and the residue was dissolved in EtOAc (30 ml) and washed with water (15 ml) and with a sat. NaHCO$_3$ (20 ml). The organic phase was dried (Na$_2$SO$_4$), filtered and evaporated. The crude was purified by flash chromatography (DCM/MeOH=92/8 to 85/15) to obtain (R)-quinuclidin-3-yl 2-phenyl-2-(pyrrolidin-1-yl)acetate (53 mg, 27.2% yield) as a colorless oil.

$^1$H NMR (300 MHz, DMSO-d6) ppm 7.40-7.53 (m, 2H), 7.18-7.40 (m, 3H), 4.53-4.88 (m, 1H), 4.01 (s, 1H), 2.92-3.14 (m, 1H), 2.55-2.70 (m, 5H), 2.12-2.41 (m, 4H), 1.73-1.92 (m, 1H), 1.65-1.72 (m, 4H), 1.08-1.63 (m, 4H).

Preparation of (3R)-1-(2-oxo-2-phenylethyl)-3-(2-phenyl-2-(pyrrolidin-1-yl)acetoxy)-1-azoniabicyclo[2.2.2]octane chloride (C37)

(R)-Quinuclidin-3-yl 2-phenyl-2-(pyrrolidin-1-yl)acetate (51 mg, 0.16 mmol) was dissolved in ethyl acetate (1.6 ml) and 2-chloro-1-phenylethanone (25.1 mg, 0.16 mmol) was added. The solution was stirred at room temperature for 3.5 days. The suspension was evaporated and the residue was purified by flash chromatography (DCM/MeOH=9/1 to 85/15) to obtain (3R)-1-(2-oxo-2-phenylethyl)-3-(2-phenyl-2-(pyrrolidin-1-yl)acetoxy)-1-azoniabicyclo[2.2.2]octane chloride (44 mg, 57.8% yield) as a yellow vitreous solid.

$^1$H NMR (300 MHz, DMSO-d6) ppm 7.86-8.05 (m, 2H), 7.70-7.83 (m, 1H), 7.57-7.66 (m, 2H), 7.44-7.53 (m, 2H), 7.29-7.44 (m, 3H), 5.23 and 5.25 (s, 1H), 5.11-5.23 (m, 1H), 4.13 and 4.14 (s, 1H), 4.00-4.23 (m, 1H), 3.45-3.83 (m, 5H), 2.53-2.59 (m, 1H), 2.32-2.46 (m, 4H), 2.15-2.34 (m, 1H), 1.46-2.12 (m, 8H).

UPLC-MS (ESI POS) 433.13 (M+).

Example 12

Preparation of (3R)-3-(2-morpholino-2-phenylacetoxy)-1-(2-oxo-2-phenylethyl)-1-azoniabicyclo[2.2.2]octane chloride (C41)

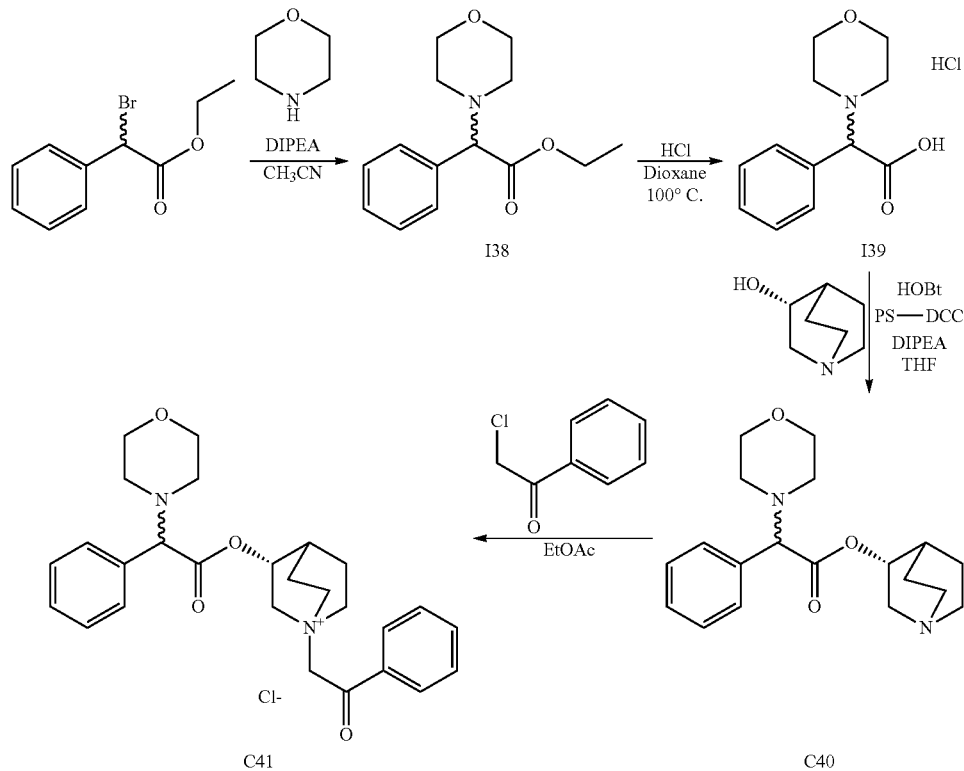

Scheme 13

Preparation of ethyl 2-morpholino-2-phenylacetate (I38)

Ethyl 2-bromo-2-phenylacetate (0.22 ml, 1.23 mmol) was dissolved in acetonitrile (4.0 ml) and DIPEA (0.26 ml, 1.48 mmol) and morpholine (0.13 ml, 1.481 mmol) were sequentially added. The solution was stirred at room temperature for 1.5 hours. Acetonitrile was evaporated and the residue was purified by flash chromatography (petroleum ether/EtOAc=85/15) to obtain ethyl 2-morpholino-2-phenylacetate (345 mg, quantitative yield) as a colorless oil.

$^1$H NMR (300 MHz, DMSO-d6) ppm 7.20-7.46 (m, 5H), 4.09 (s, 1H), 4.12 (dq, 1H), 4.06 (dq, 1H), 3.47-3.70 (m, 4H), 2.31-2.41 (m, 4H), 1.13 (t, 3H).

Preparation of 2-morpholino-2-phenylacetic acid hydrochloride (I39)

Ethyl 2-morpholino-2-phenylacetate (0.34 g, 1.36 mmol) was dissolved in dioxane (11.4 ml) and 37% HCl (1.1 ml, 13.6 mmol) was added dropwise. The mixture was stirred at reflux overnight. 37% HCl (1.1 ml, 13.6 mmol) was added and the reaction was refluxed for additional 24 hours. The solvent was evaporated and the residue was triturated with acetonitrile (10 ml) to obtain 2-morpholino-2-phenylacetic acid hydrochloride (0.22 g, 63.7% yield) as a white solid.

$^1$H NMR (300 MHz, DMSO-d6) ppm 11.79 (s, 1H), 7.56-7.72 (m, 2H), 7.37-7.56 (m, 3H), 5.25 (s, 1H), 3.60-4.10 (m, 4H), 3.27 (br. s., 2H), 2.96 (br. s., 2H).

Preparation of (R)-quinuclidin-3-yl 2-morpholino-2-phenylacetate (C40)

PS-DCC (loading: 1.25 mmol/g; 0.93 g, 1.16 mmol) was suspended in dry THF (11.6 ml) and HOBT (0.18 g, 1.16 mmol), 2-morpholino-2-phenylacetic acid hydrochloride (0.15 g, 0.58 mmol) and (R)-quinuclidin-3-ol (0.22 g, 1.75 mmol) were sequentially added. The mixture was shaken overnight and then PS-DCC was filtered off washing with EtOAc and THF. The solution was evaporated and the residue was dissolved in EtOAc (30 ml) and washed with water and then with a sat. NaHCO$_3$. The organic phase was dried (Na$_2$SO$_4$), filtered and evaporated. The crude was purified by flash chromatography (DCM/MeOH=95/5 to 85/15) to obtain (R)-quinuclidin-3-yl 2-morpholino-2-phenylacetate (45 mg, 23.4% yield) as a colorless oil.

$^1$H NMR (300 MHz, DMSO-d6) ppm 7.11-7.51 (m, 5H), 4.60-4.82 (m, 1H), 4.10 (s, 1H), 3.48-3.66 (m, 4H), 2.91-3.18 (m, 1H), 2.54-2.78 (m, 4H), 2.18-2.45 (m, 5H), 1.71-1.93 (m, 1H), 1.05-1.69 (m, 4H)

Preparation of (3R)-3-(2-morpholino-2-phenylacetoxy)-1-(2-oxo-2-phenylethyl)-1-azoniabicyclo[2.2.2]octane chloride (C41)

(R)-Quinuclidin-3-yl 2-morpholino-2-phenylacetate (43 mg, 0.13 mmol) was dissolved in ethyl acetate (1.3 ml) and 2-chloro-1-phenylethanone (22.1 mg, 0.14 mmol) was added. The solution was stirred at room temperature for two days. The solvent was evaporated and the residue was triturated with Et$_2$O to obtain (3R)-3-(2-morpholino-2-phenylacetoxy)-1-(2-oxo-2-phenylethyl)-1-azoniabicyclo[2.2.2]octane chloride (53 mg, 84% yield) as a pale yellow solid.

$^1$H NMR (300 MHz, DMSO-d6) ppm 7.85-8.04 (m, 2H), 7.70-7.84 (m, 1H), 7.55-7.69 (m, 2H), 7.27-7.54 (m, 5H), 5.25 and 5.27 (s, 2H), 5.11-5.25 (m, 1H), 4.23 and 4.26 (s, 1H), 4.04-4.22 (m, 1H), 3.62-3.83 (m, 5H), 3.54-3.62 (m, 4H), 2.39-2.47 (m, 4H), 2.16-2.25 (m, 1H), 1.59-2.15 (m, 4H).

UPLC-MS (ESI POS) 449.24 (M+).

Example 13

Preparation of (3R)-1-(2-oxo-2-phenylethyl)-3-(2-phenyl-2-thiomorpholinoacetoxy)-1-azoniabicyclo[2.2.2]octane chloride (C45)

$^1$H NMR (300 MHz, DMSO-d6) ppm 7.10-7.83 (m, 5H), 4.31 (s, 1H), 4.14 (dq, 1H), 4.09 (dq, 1H), 2.55-2.87 (m, 8H), 1.15 (t, 3H).

Preparation of 2-phenyl-2-thiomorpholinoacetic acid hydrochloride (I43)

37% aq HCl (1.1 ml, 13.5 mmol) was added dropwise to a solution of ethyl 2-phenyl-2-thiomorpholinoacetate (0.36 g, 1.35 mmol) in dioxane (11 ml). The mixture was stirred at reflux overnight. Then 37% aq HCl (1.1 ml, 13.5 mmol) was added again and the reaction was refluxed for additional 24 hours. Solvents were evaporated, the residue was triturated with acetonitrile and collected by suction filtration to obtain 2-phenyl-2-thiomorpholinoacetic acid hydrochloride (0.13 g, 34.4% yield) as a off-white solid.

$^1$H NMR (300 MHz, DMSO-d6) ppm 7.09-7.78 (m, 5H), 5.26 (s, 1H), 3.09-3.41 (m, 4H), 2.98 (br. s., 4H).

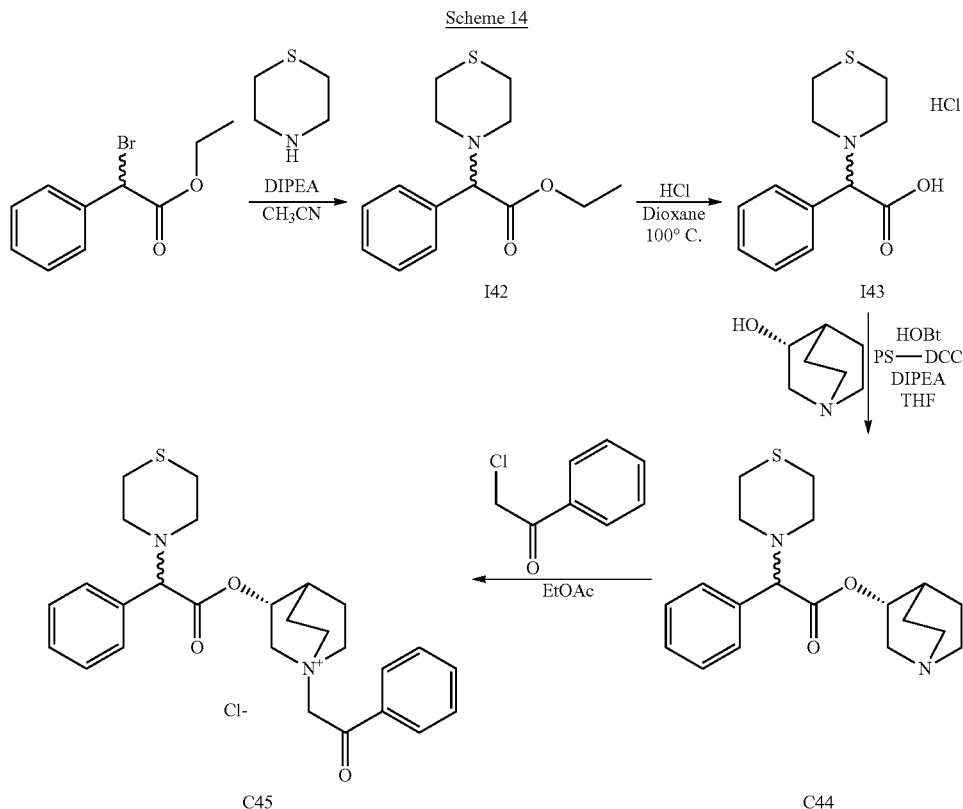

Scheme 14

Preparation of ethyl 2-phenyl-2-thiomorpholinoacetate (I42)

Ethyl 2-bromo-2-phenylacetate (0.22 ml, 1.23 mmol) was dissolved in acetonitrile (4.0 ml). DIPEA (0.26 ml, 1.481 mmol) and thiomorpholine (0.15 ml, 1.41 mmol) were sequentially added and the solution was stirred at room temperature for 1.5 hours. Acetonitrile was evaporated and the residue was purified by flash chromatography (petroleum ether/EtOAc=95/5) to obtain ethyl 2-phenyl-2-thiomorpholinoacetate (362 mg, quantitative yield) as a colorless oil.

Preparation of (R)-quinuclidin-3-yl 2-phenyl-2-thiomorpholinoacetate (C44)

PS-DCC (loading: 1.25 mmol/g; 0.73 g, 0.91 mmol) was suspended in dry THF (9 ml). HOBT (0.14 g, 0.91 mmol), 2-phenyl-2-thiomorpholinoacetic acid hydrochloride (0.12 g, 0.46 mmol) and (R)-quinuclidin-3-ol (0.17 g, 1.37 mmol) were sequentially added. The mixture was shaken overnight. PS-DCC was filtered off and washed with EtOAc and THF. The solution was evaporated and the residue was portioned between EtOAc and water. The organic phase was washed with sat. NaHCO$_3$, dried (Na$_2$SO$_4$), filtered and evaporated. The crude was purified by flash chromatography (DCM/

MeOH=95/5 to 85/15) to obtain (R)-quinuclidin-3-yl 2-phenyl-2-thiomorpholinoacetate (70 mg, 44.2% yield) as a colorless oil.

Preparation of (3R)-1-(2-oxo-2-phenylethyl)-3-(2-phenyl-2-thiomorpholinoacetoxy)-1-azoniabicyclo[2.2.2]octane chloride (C45)

(R)-quinuclidin-3-yl 2-phenyl-2-thiomorpholinoacetate (68 mg, 0.20 mmol) was dissolved in ethyl acetate (2 ml) and 2-chloro-1-phenylethanone (33.4 mg, 0.22 mmol) was added. The solution was stirred at room temperature for two days. The solvent was evaporated and the residue was triturated with Et$_2$O. The suspension was filtered on a buckner funnel to obtain (3R)-1-(2-oxo-2-phenylethyl)-3-(2-phenyl-2-thiomorpholinoacetoxy)-1-azoniabicyclo[2.2.2]octane chloride (89 mg, 0.178 mmol, 91% yield) as an off-white solid.

$^1$H NMR (300 MHz, DMSO-d6) ppm 7.89-8.08 (m, 2H), 7.71-7.83 (m, 1H), 7.56-7.67 (m, 2H), 7.27-7.49 (m, 5H), 5.27 (s, 2H), 5.20-5.25 (m, 1H), 4.46 (s, 1H), 4.01-4.28 (m, 1H), 3.48-3.82 (m, 5H), 2.57-2.88 (m, 8H), 2.23-2.42 (m, 1H), 1.58-2.16 (m, 4H).

UPLC-MS (ESI POS) 465.09 (M+).

Example 14

Preparation of (3R)-3-(2-(4-methyl-3-oxopiperazin-1-yl)-2-phenylacetoxy)-1-(2-oxo-2-phenylethyl)-1-azoniabicyclo[2.2.2]octane chloride (C53)

Preparation of ethyl 2-(4-methyl-3-oxopiperazin-1-yl)-2-phenylacetate (I50)

DIPEA (0.52 ml, 2.96 mmol) and 1-methylpiperazin-2-one hydrochloride (0.22 g, 1.48 mmol) were sequentially added to a solution of ethyl 2-bromo-2-phenylacetate (0.22 ml, 1.23 mmol) in acetonitrile (4 ml). The reaction was stirred at room temperature for 1.5 hours. DIPEA (0.13 ml, 0.74 mmol) was added again and the reaction was stirred at room temperature overnight. The solvent was evaporated and the crude was purified by flash chromatography (DCM/Acetone=9/1) to obtain ethyl 2-(4-methyl-3-oxopiperazin-1-yl)-2-phenylacetate (256 mg, 75% yield) as a yellow oil.

$^1$H NMR (300 MHz, DMSO-d6) ppm 6.91-7.66 (m, 5H), 4.28 (s, 1H), 3.99-4.22 (m, 2H), 3.23 (t, 2H), 3.00 (s, 2H), 2.80 (s, 3H), 2.61-2.71 (m, 2H), 1.14 (t, 3H).

Preparation of 2-(4-methyl-3-oxopiperazin-1-yl)-2-phenylacetic acid (I51)

Ethyl 2-(4-methyl-3-oxopiperazin-1-yl)-2-phenylacetate (250 mg, 0.90 mmol) was dissolved in ethanol (8.6 ml) and water (4.3 ml). Lithium hydroxide (28.2 mg, 1.18 mmol) was added and the reaction was stirred at room temperature for three days. A second portion of lithium hydroxide (4.33 mg, 0.18 mmol) was added and the reaction was stirred at room temperature for 24 hours. EtOH was evaporated and 1N HCl was added to the aqueous solution till pH 7. The water was evaporated and the residue was suspended in acetonitrile and

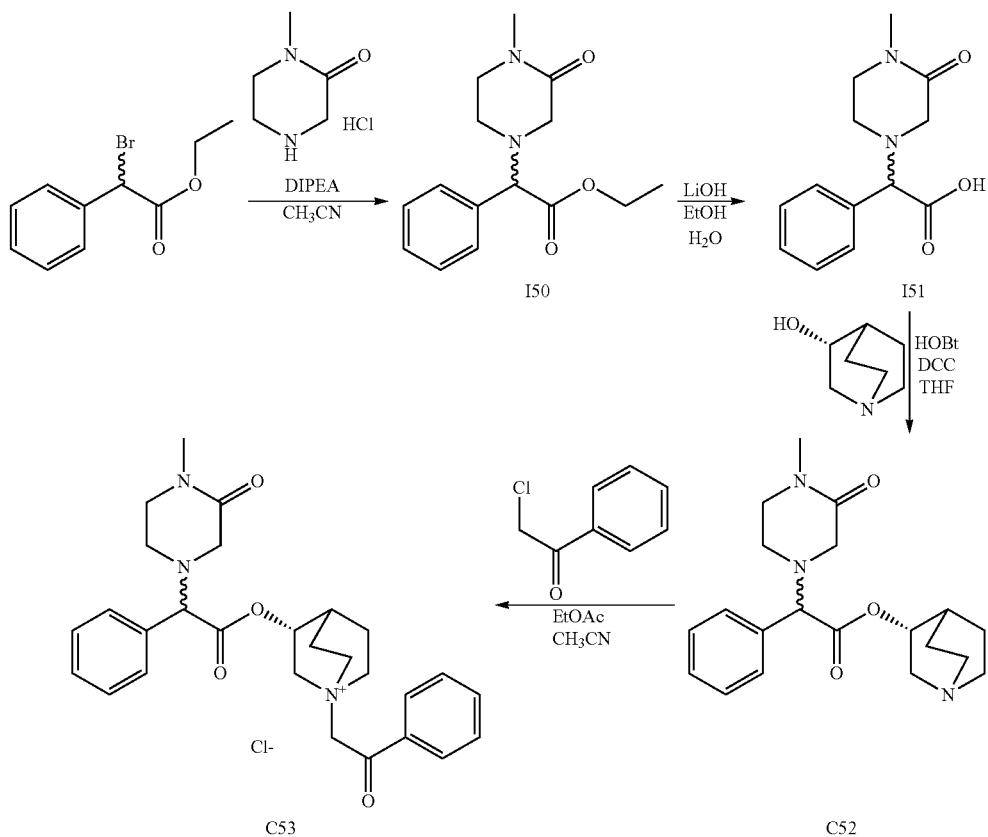

Scheme 15 filtered on a buckner funnel washing with acetonitrile to obtain 170 mg of desired compound as a white solid. The compound was used in the next step without any further purification.

$^1$H NMR (300 MHz, DMSO-d6) ppm 7.34-7.51 (m, 2H), 7.08-7.34 (m, 3H), 3.66 (s, 1H), 3.18 (t, 2H), 3.14 (d, 1H), 2.89 (d, 1H), 2.79 (s, 3H), 2.55-2.71 (m, 2H)

Preparation of (R)-quinuclidin-3-yl 2-(4-methyl-3-oxopiperazin-1-yl)-2-phenylacetate (C52)

2-(4-Methyl-3-oxopiperazin-1-yl)-2-phenylacetic acid (170 mg, 0.68 mmol) was suspended in dry THF (6 ml) and DCC (283 mg, 1.37 mmol), HOBT (185 mg, 1.37 mmol) and (R)-quinuclidin-3-ol (174 mg, 1.37 mmol) were sequentially added. The reaction was stirred at room temperature for two days and then the insoluble was filtered off. The solution was evaporated and the residue was purified by flash chromatography (DCM/MeOH/NH4OH=96/4/0.4) to obtain (R)-quinuclidin-3-yl 2-(4-methyl-3-oxopiperazin-1-yl)-2-phenylacetate (175 mg, 54.1% yield over 2 steps) as a off-white spongy solid $^1$H NMR (300 MHz, DMSO-d6) ppm 7.09-7.60 (m, 5H), 4.64-4.87 (m, 1H), 4.28 (s, 1H), 3.24 (t, 2H), 3.04-3.14 (m, 1H), 3.01 (s, 2H), 2.81 (s, 3H), 2.66-2.72 (m, 2H), 2.54-2.65 (m, 4H), 2.35-2.47 (m, 1H), 1.70-1.81 and 1.85-1.95 (m, 1H), 1.06-1.69 (m, 4H).

Preparation of (3R)-3-(2-(4-methyl-3-oxopiperazin-1-yl)-2-phenylacetoxy)-1-(2-oxo-2-phenylethyl)-1-azoniabicyclo[2.2.2]octane chloride (C53)

(R)-Quinuclidin-3-yl 2-(4-methyl-3-oxopiperazin-1-yl)-2-phenylacetate (169 mg, 0.47 mmol) was dissolved in a mixture of ethyl acetate (3 ml) and acetonitrile (1.5 ml). 2-Chloro-1-phenylethanone (80 mg, 0.52 mmol) was added and the reaction was stirred at room temperature for 5 hours. The solvent was evaporated and the residue was triturated with EtOAc (10 ml). The product was purified by flash chromatography (DCM/MeOH=9/1 to 85/15) to obtain (3R)-3-(2-(4-methyl-3-oxopiperazin-1-yl)-2-phenylacetoxy)-1-(2-oxo-2-phenylethyl)-1-azoniabicyclo[2.2.2]octane chloride (99 mg, 0.193 mmol, 40.9% yield) as a pale yellow spongy solid.

$^1$H NMR (300 MHz, DMSO-d6) ppm 7.90-8.12 (m, 2H), 7.68-7.85 (m, 1H), 7.55-7.68 (m, 2H), 7.27-7.51 (m, 5H), 5.28-5.38 (m, 2H), 5.17-5.27 (m, 1H), 4.41 and 4.45 (s, 1H), 4.10-4.28 (m, 1H), 3.51-3.86 (m, 5H), 3.21-3.29 (m, 2H), 3.11 (d, 1H), 3.02 (d, 1H), 2.82 (s, 3H), 2.67-2.77 (m, 2H), 2.17-2.25 and 2.34-2.42 (m, 1H), 1.52-2.13 (m, 4H);

UPLC-MS (ESI POS) 476.09 (M+).

Example 15

Preparation of (3R)-3-(2-(4-acetylpiperazin-1-yl)-2-phenylacetoxy)-1-(2-oxo-2-phenylethyl)-1-azoniabicyclo[2.2.2]octane chloride (C57)

Scheme 16

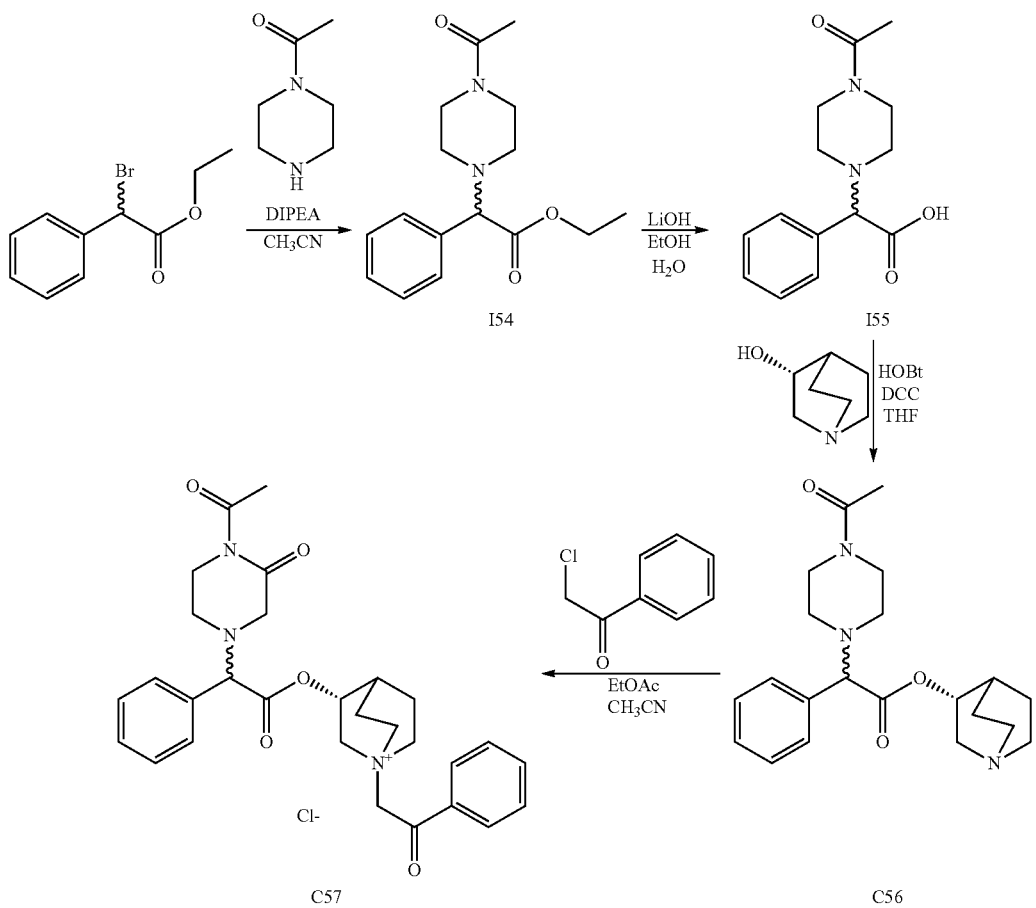

Preparation of ethyl 2-(4-acetylpiperazin-1-yl)-2-phenylacetate (I54)

Ethyl 2-bromo-2-phenylacetate (0.22 ml, 1.23 mmol) was dissolved in acetonitrile (4 ml) and DIPEA (0.28 ml, 1.60 mmol) and 1-(piperazin-1-yl)ethanone (0.21 g, 1.60 mmol) were sequentially added. The reaction was stirred at room temperature overnight. The solvent was evaporated and the residue was purified by flash chromatography (DCM/Acetone=9/1) to obtain ethyl 2-(4-acetylpiperazin-1-yl)-2-phenylacetate (341 mg, 95% yield) as a pale yellow oil.

$^1$H NMR (300 MHz, DMSO-d6) ppm 6.80-7.63 (m, 5H), 4.18 (s, 1H), 4.00-4.16 (m, 2H), 3.33-3.49 (m, 4H), 2.26-2.45 (m, 4H), 1.95 (s, 3H), 1.13 (t, 3H).

Preparation of 2-(4-acetylpiperazin-1-yl)-2-phenylacetic acid (I55)

Ethyl 2-(4-acetylpiperazin-1-yl)-2-phenylacetate (285 mg, 0.98 mmol) was dissolved in a mixture EtOH (6.5 ml) and water (3.3 ml). LiOH (23.5 mg, 0.98 mmol) was added and the reaction was stirred at room temperature overnight. LiOH (23.5 mg, 0.982 mmol) was added again and the mixture was stirred for additional 24 hours. EtOH was evaporated and 1N HCl was added dropwise to the aqueous solution till pH 6-7 before evaporating to dryness. The crude was purified by flash chromatography (DCM/MeOH=75/25) to obtain 2-(4-acetylpiperazin-1-yl)-2-phenylacetic acid (246 mg, 96% yield) as a white solid.

$^1$H NMR (300 MHz, DMSO-d6) ppm 7.37-7.49 (m, 2H), 7.20-7.37 (m, 3H), 3.90 (s, 1H), 3.26-3.50 (m, 4H), 2.15-2.47 (m, 4H), 1.95 (s, 3H).

Preparation of (R)-quinuclidin-3-yl 2-(4-acetylpiperazin-1-yl)-2-phenylacetate (C56)

2-(4-Acetylpiperazin-1-yl)-2-phenylacetic acid (238 mg, 0.91 mmol) was suspended in dry THF (9 ml) and, with stirring at room temperature under nitrogen atmosphere, DCC (374 mg, 1.81 mmol), HOBT (245 mg, 1.81 mmol) and (R)-quinuclidin-3-ol (231 mg, 1.81 mmol) were sequentially added. The reaction was reacted at the same temperature for three days. The solvent was evaporated and the crude was purified by flash chromatography (DCM/MeOH/NH$_4$OH=97/3/0.3). The product was suspended in THF/Acetonitrile (2/1; 10 ml) and the white solid was filtered off. The colourless solution was evaporated obtaining (R)-quinuclidin-3-yl 2-(4-acetylpiperazin-1-yl)-2-phenylacetate (218 mg, 64.7% yield) as a off-white spongy solid.

$^1$H NMR (300 MHz, DMSO-d6) ppm 7.22-7.55 (m, 5H), 4.61-4.80 (m, 1H), 4.19 (s, 1H), 3.36-3.54 (m, 4H), 3.04-3.19 (m, 1H), 2.54-2.78 (m, 4H), 2.28-2.46 (m, 5H), 1.95 (s, 3H), 1.68-1.80 (m, 1H), 1.02-1.67 (m, 4H)

Preparation of (3R)-3-(2-(4-acetylpiperazin-1-yl)-2-phenylacetoxy)-1-(2-oxo-2-phenylethyl)-1-azoniabicyclo[2.2.2]octane chloride (C57)

(R)-Quinuclidin-3-yl 2-(4-acetylpiperazin-1-yl)-2-phenylacetate (210 mg, 0.56 mmol) was dissolved in a mixture EtOAc (3.8 ml) and acetonitrile (1.8 ml). 2-Chloro-1-phenylethanone (96 mg, 0.62 mmol) was added and the reaction was stirred at room temperature for 16 hours. The solvent was evaporated and the crude was purified by flash chromatography (DCM/MeOH=9/1) to obtain (3R)-3-(2-(4-acetylpiperazin-1-yl)-2-phenylacetoxy)-1-(2-oxo-2-phenylethyl)-1-azoniabicyclo[2.2.2]octane chloride (178 mg, 59.9% yield) as an off-white spongy solid.

$^1$H NMR (300 MHz, DMSO-d6) ppm 7.89-8.08 (m, 2H), 7.70-7.87 (m, 1H), 7.55-7.69 (m, 2H), 7.30-7.52 (m, 5H), 5.29 (s, 2H), 5.17-5.28 (m, 1H), 4.34 (s, 1H), 4.08-4.25 (m, 1H), 3.37-3.86 (m, 9H), 2.31-2.47 (m, 4H), 2.17-2.29 (m, 1H), 1.98-2.12 (m, 2H), 1.96 (s, 3H), 1.59-1.94 (m, 2H).

UPLC-MS (ESI POS) 490.26 (M+).

Example 16

Preparation of (3R)-3-(2-(4-carbamoylpiperidin-1-yl)-2-phenylacetoxy)-1-(2-oxo-2-phenylethyl)-1-azoniabicyclo[2.2.2]octane chloride (C61)

Scheme 17

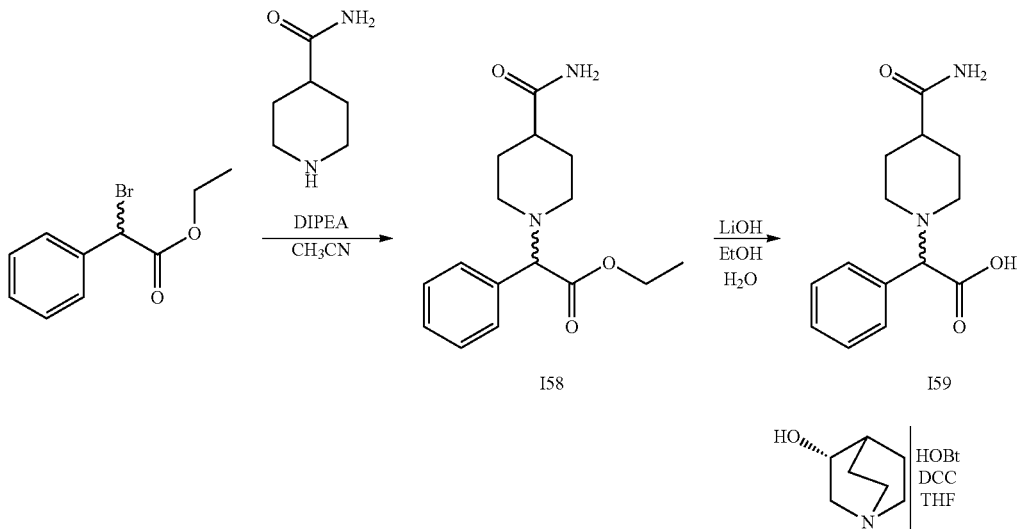

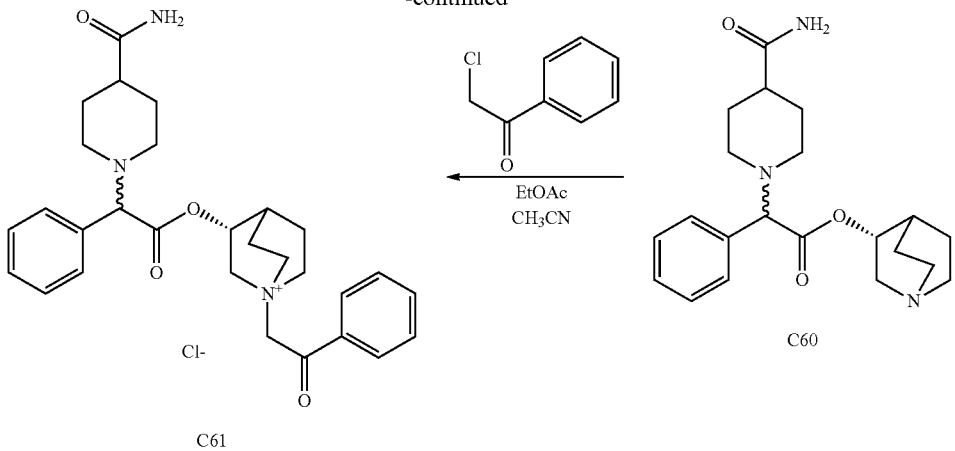

Preparation of ethyl 2-(4-carbamoylpiperidin-1-yl)-2-phenylacetate (I58)

Ethyl 2-bromo-2-phenylacetate (0.22 ml, 1.23 mmol) was dissolved in acetonitrile (4 ml). DIPEA (0.28 ml, 1.60 mmol) and piperidine-4-carboxamide (0.21 g, 1.60 mmol) were sequentially added. The reaction was stirred at room temperature overnight. The mixture was evaporated and the residue was purified by flash chromatography (DCM/Acetone=8/2). The solid was triturated with i-Pr$_2$O to obtain ethyl 2-(4-carbamoylpiperidin-1-yl)-2-phenylacetate (239 mg, 66.7% yield) as a pale yellow solid.

$^1$H NMR (300 MHz, DMSO-d6) ppm 7.26-7.47 (m, 5H), 7.15 (br. s., 1H), 6.66 (br. s., 1H), 3.95-4.27 (m, 3H), 2.75-2.90 (m, 1H), 2.59-2.75 (m, 1H), 2.12 (td, 1H), 1.97-2.06 (m, 1H), 1.92 (td, 1H), 1.44-1.77 (m, 4H), 1.14 (t, 3H).

Preparation of (R)-quinuclidin-3-yl 2-(4-carbamoylpiperidin-1-yl)-2-phenylacetate (C60)

2-(4-Carbamoylpiperidin-1-yl)-2-phenylacetic acid (145 mg, 0.55 mmol) was suspended in dry THF (5.5 ml) and DCC (240 mg, 1.16 mmol), HOBT (157 mg, 1.16 mmol) and (R)-quinuclidin-3-ol (148 mg, 1.16 mmol) were sequentially added. The mixture was stirred at room temperature under nitrogen atmosphere for 24 hours. The white solid was filtered off and the solution was evaporated. The crude was purified by flash chromatography (DCM/MeOH/NH$_4$OH=95/5/0.5) to obtain (R)-quinuclidin-3-yl 2-(4-carbamoylpiperidin-1-yl)-2-phenylacetate (78 mg, 38% yield) as an off-white spongy solid.

$^1$H NMR (300 MHz, DMSO-d6) ppm 7.26-7.46 (m, 5H) 7.16 (br. s., 1H) 6.66 (br. s., 1H) 4.58-4.80 (m, 1H) 4.11 (s, 1H) 2.94-3.16 (m, 1H) 2.78-2.94 (m, 1H) 2.54-2.76 (m, 4H) 2.33-2.47 (m, 1H) 1.72-2.30 (m, 5H) 1.35-1.72 (m, 7H) 1.07-1.35 (m, 1H).

Preparation of 2-(4-carbamoylpiperidin-1-yl)-2-phenylacetic acid (I59)

Ethyl 2-(4-carbamoylpiperidin-1-yl)-2-phenylacetate (202 mg, 0.69 mmol) was dissolved in a mixture EtOH (4.6 ml) and water (2.3 ml), and lithium hydroxide (50.0 mg, 2.09 mmol) was added. The reaction was stirred at room temperature overnight. LiOH (33.3 mg, 1.39 mmol) was added in two portions in the following two days. EtOH was evaporated and 1N HCl was added dropwise to the aqueous solution till pH 6-7. The solution was evaporated and the residue was purified by flash chromatography (DCM/MeOH=7/3 to 6/4) to obtain 2-(4-carbamoylpiperidin-1-yl)-2-phenylacetic acid (155 mg, 85% yield) as a white solid.

$^1$H NMR (300 MHz, DMSO-d6) ppm 7.38-7.48 (m, 2H), 7.25-7.38 (m, 3H), 7.20 (br. s., 1H), 6.70 (br. s., 1H), 3.96 (s, 1H), 3.05-3.24 (m, 1H), 2.62-2.79 (m, 1H), 2.26 (td, 1H), 1.98-2.18 (m, 2H), 1.52-1.89 (m, 4H).

Preparation of (3R)-3-(2-(4-carbamoylpiperidin-1-yl)-2-phenylacetoxy)-1-(2-oxo-2-phenylethyl)-1-azoniabicyclo[2.2.2]octane chloride (C61)

(R)-Quinuclidin-3-yl 2-(4-carbamoylpiperidin-1-yl)-2-phenylacetate (72 mg, 0.19 mmol) was dissolved in a mixture EtOAc (1.3 ml) and acetonitrile (0.6 ml). 2-Chloro-1-phenylethanone (33.0 mg, 0.21 mmol) was added and the mixture was reacted at the same temperature for three days. The mixture was evaporated and the crude was purified by flash chromatography (DCM/MeOH=85/15 to 8/2) to obtain (3R)-3-(2-(4-carbamoylpiperidin-1-yl)-2-phenylacetoxy)-1-(2-oxo-2-phenylethyl)-1-azoniabicyclo[2.2.2]octane chloride (34 mg, 33.3% yield) as a pale yellow solid.

$^1$H NMR (300 MHz, DMSO-d6) ppm 7.94-8.04 (m, 2H), 7.69-7.82 (m, 1H), 7.55-7.67 (m, 2H), 7.30-7.49 (m, 5H), 7.20 (br. s., 1H), 6.68 (br. s., 1H), 5.32 (s, 2H), 5.18-5.28 (m, 1H), 4.24 (s, 1H), 4.10-4.33 (m, 1H), 3.51-3.88 (m, 5H), 2.83-2.97 (m, 1H), 2.69-2.82 (m, 1H), 1.38-2.40 (m, 12H).

UPLC-MS (ESI POS) 490.23 (M+).

Example 17

Preparation of (3R)-3-(2-(3,5-dimethylpiperidin-1-yl)-2-phenylacetoxy)-1-(2-oxo-2-phenylethyl)-1-azoniabicyclo[2.2.2]octane bromide (C64)

Scheme 18

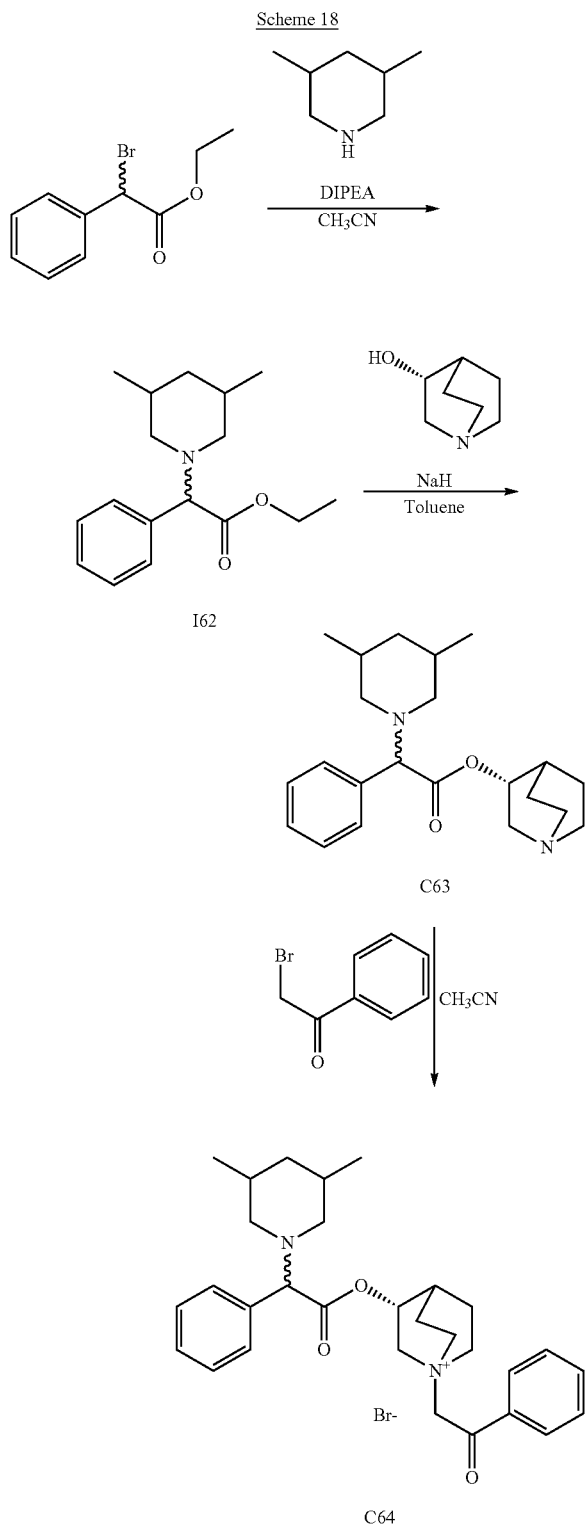

Preparation of ethyl 2-(3,5-dimethylpiperidin-1-yl)-2-phenylacetate (I62)

Ethyl 2-bromo-2-phenylacetate (0.22 ml, 1.23 mmol), 3,5-dimethylpiperidine (0.20 ml, 1.48 mmol), and DIPEA (0.26 ml, 1.48 mmol) were dissolved in acetonitrile (12 ml) and stirred at room temperature for 16 hours. Acetonitrile was evaporated and the crude was purified by flash chromatography (Petroleum ether/EtOAc=95/5) to obtain ethyl 2-(3,5-dimethylpiperidin-1-yl)-2-phenylacetate (203 mg, 59.7% yield) as colourless oil.

$^1$H NMR (300 MHz, DMSO-d6) ppm 7.24-7.42 (m, 5H) 3.99-4.19 (m, 3H) 2.69-2.80 (m, 1H) 2.57-2.68 (m, 1H) 1.49-1.73 (m, 4H) 1.36-1.48 (m, 1H) 1.13 (t, 3H) 0.79 (d, 3H) 0.72 (d, 3H) 0.39-0.56 (m, 1H)

Preparation of (R)-quinuclidin-3-yl 2-(3,5-dimethylpiperidin-1-yl)-2-phenylacetate (C63)

(R)-quinuclidin-3-ol (175 mg, 1.38 mmol) and NaH (60% dispersion in mineral oil, 52.3 mg, 1.31 mmol) were suspended in dry toluene (9 ml) under nitrogen atmosphere and stirred at room temperature for 20 minutes. Ethyl 2-(3,5-dimethylpiperidin-1-yl)-2-phenylacetate (200 mg, 0.73 mmol) was added and the resulting mixture was stirred at 100° C. for 24 hours. NaH (60% dispersion in mineral oil, 8.72 mg, 0.36 mmol) was added again and the mixture was refluxed for others 24 hours. The reaction was cooled and partitioned between water and ethyl ether. The organic layer was collected and dried over $Na_2SO_4$, filtered and evaporated. The crude compound was purified by flash chromatography (DCM/MeOH=9/1) to obtain (R)-quinuclidin-3-yl 2-(3,5-dimethylpiperidin-1-yl)-2-phenylacetate (125 mg, 48.3% yield) as a colourless oil.

$^1$H NMR (300 MHz, DMSO-d6) ppm 7.22-7.46 (m, 5H) 4.63-4.80 (m, 1H) 4.10 (s, 1H) 2.97-3.15 (m, 1H) 2.75-2.88 (m, 1H) 2.54-2.71 (m, 5H) 2.14-2.46 (m, 1H) 1.73-1.94 (m, 1H) 1.37-1.73 (m, 8H) 1.05-1.37 (m, 1H) 0.79 (d, 3H) 0.72 (d, 3H) 0.39-0.57 (m, 1H)

Preparation of (3R)-3-(2-(3,5-dimethylpiperidin-1-yl)-2-phenylacetoxy)-1-(2-oxo-2-phenylethyl)-1-azoniabicyclo[2.2.2]octane bromide (C64)

(R)-quinuclidin-3-yl 2-(3,5-dimethylpiperidin-1-yl)-2-phenylacetate (120 mg, 0.34 mmol) and 2-bromo-1-phenylethanone (73.7 mg, 0.37 mmol) were dissolved in acetonitrile (5 ml) and stirred at room temperature for 16 hours. Acetonitrile was evaporated, the residue was taken up with little EtOAc (2 ml) and then $Et_2O$ was added. The white solid that precipitated out was recovered by suction filtration and washed on the filter paper with $Et_2O$. The solid was dried to obtain (3R)-3-(2-(3,5-dimethylpiperidin-1-yl)-2-phenylacetoxy)-1-(2-oxo-2-phenylethyl)-1-azoniabicyclo[2.2.2]octane bromide (115.8 mg, 61.9% yield).

1H NMR (300 MHz, DMSO-d6) ppm 7.91-8.04 (m, 2H), 7.71-7.83 (m, 1H), 7.57-7.68 (m, 2H), 7.20-7.49 (m, 5H), 5.23-5.26 (m, 1H), 5.22 (br. s., 2H), 4.29 (s, 1H), 4.07-4.20 (m, 1H), 3.49-3.86 (m, 5H), 2.63-2.91 (m, 2H), 2.20-2.42 (m, 1H), 1.39-2.17 (m, 9H), 0.82 (d, 3H), 0.75 (d, 3H), 0.38-0.64 (m, 1H);

UPLC-MS (ESI POS) 475.26 (M+).

Example 18

Preparation of (3R)-3-(2-(4,4-difluoropiperidin-1-yl)-2-phenylacetoxy)-1-(2-oxo-2-phenylethyl)-1-azoniabicyclo[2.2.2]octane chloride (C70)

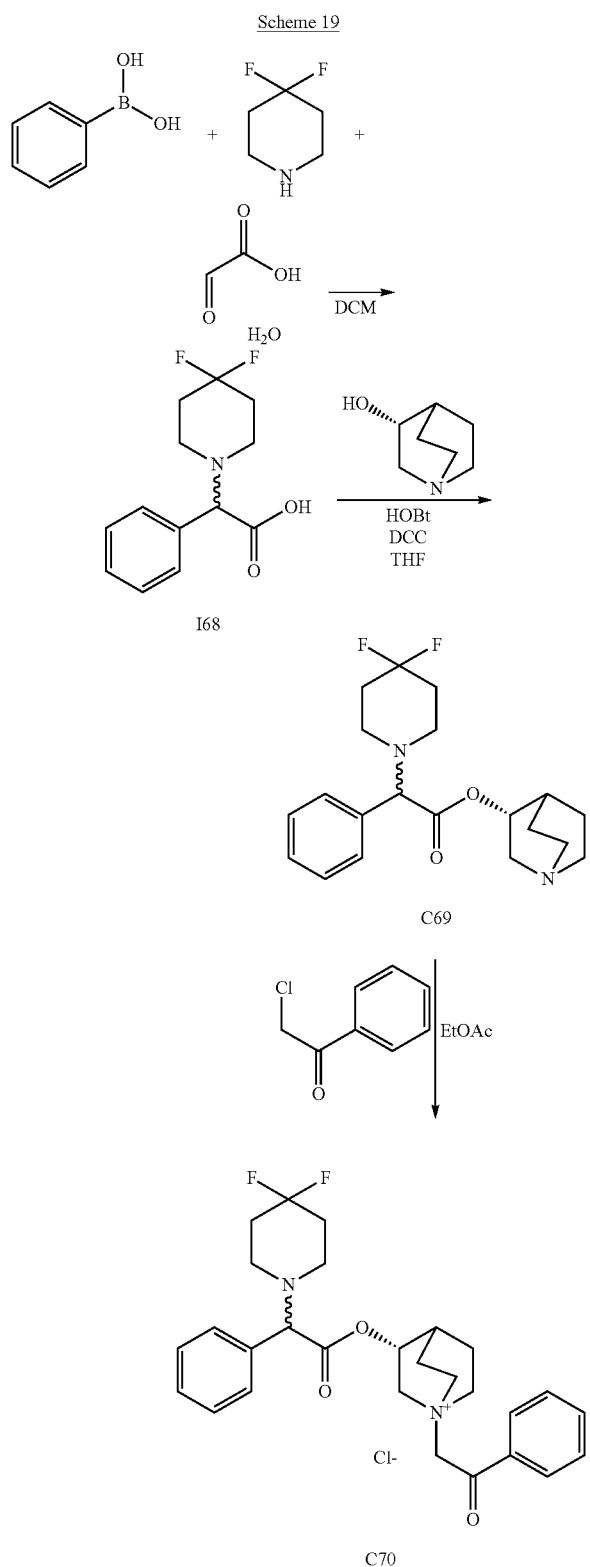

Preparation of 2-(4,4-Difluoropiperidin-1-yl)-2-phenylacetic acid (I68)

A mixture of phenylboronic acid (400 mg, 3.28 mmol), 4,4-difluoropiperidine (397 mg, 3.28 mmol) and 2-oxoacetic acid hydrate (302 mg, 3.28 mmol) in DCM (30 ml) was stirred at room temperature overnight. DCM was evaporated and crude was purified by flash-chromatography (DCM/MeOH=8/2) to obtain the title compound (512 mg, 61.1% yield) as a white solid.

UPLC-MS (ESI POS) 256.3 (MH+).

Preparation of (R)-Quinuclidin-3-yl 2-(4,4-difluoropiperidin-1-yl)-2-phenylacetate (C69)

A mixture of 2-(4,4-difluoropiperidin-1-yl)-2-phenylacetic acid (512 mg, 2.01 mmol), (R)-quinuclidin-3-ol (306 mg, 2.41 mmol), DCC (497 mg, 2.41 mmol) and HOBT (369 mg, 2.41 mmol) in THF (20 ml) was stirred at room temperature over a week-end. THF was evaporated, the crude was taken up with EtOAc and washed twice with 2M $K_2CO_3$ and then with brine. The organic phase was dried over $Na_2SO_4$, filtered and evaporated to dryness. The crude was purified by flash-chromatography (DCM/MeOH=9/1) to obtain the title compound (348 mg, 47.6% yield) as a yellow sticky oil.

UPLC-MS (ESI POS) 365.2 (MH+).

Preparation of (3R)-3-(2-(4,4-difluoropiperidin-1-yl)-2-phenylacetoxy)-1-(2-oxo-2-phenylethyl)-1-azoniabicyclo[2.2.2]octane chloride (C70)

2-Chloro-1-phenylethanone (31.0 mg, 0.20 mmol) was added to a solution of (R)-quinuclidin-3-yl 2-(4,4-difluoropiperidin-1-yl)-2-phenylacetate (24b) (73 mg, 0.20 mmol) in ethyl acetate (3 ml). The reaction was stirred at room temperature overnight. The solvent was evaporated under reduced pressure and the residue was triturated with $Et_2O$ (4 ml). A white precipitate was formed and it was collected by suction filtration and dried under vacuum at 40° C. overnight, to obtain (3R)-3-(2-(4,4-difluoropiperidin-1-yl)-2-phenylacetoxy)-1-(2-oxo-2-phenylethyl)-1-azoniabicyclo[2.2.2]octane chloride (81 mg, 78% yield).

$^1$H NMR (300 MHz, DMSO-d6) ppm 7.93-8.04 (m, 2H) 7.71-7.83 (m, 1H) 7.57-7.66 (m, 2H) 7.32-7.50 (m, 5H) 5.15-5.31 (m, 2H) 4.48 and 4.52 (s, 1H) 4.08-4.23 (m, 1H) 3.54-3.80 (m, 5H) 2.54-2.70 (m, 4H) 2.21-2.31 and 2.23-2.30 (m, 1H) 1.67-2.13 (m, 8H).

UPLC-MS (ESI POS) 483.24 (M+).

Example 19

Preparation of (3R)-3-(2-(azepan-1-yl)-2-phenylacetoxy)-1-(2-oxo-2-phenylethyl)-1-azoniabicyclo[2.2.2]octane chloride (C73)

Scheme 20

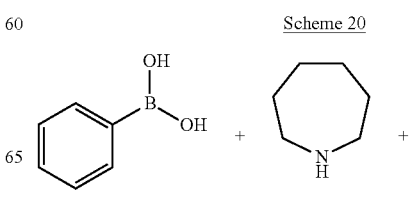

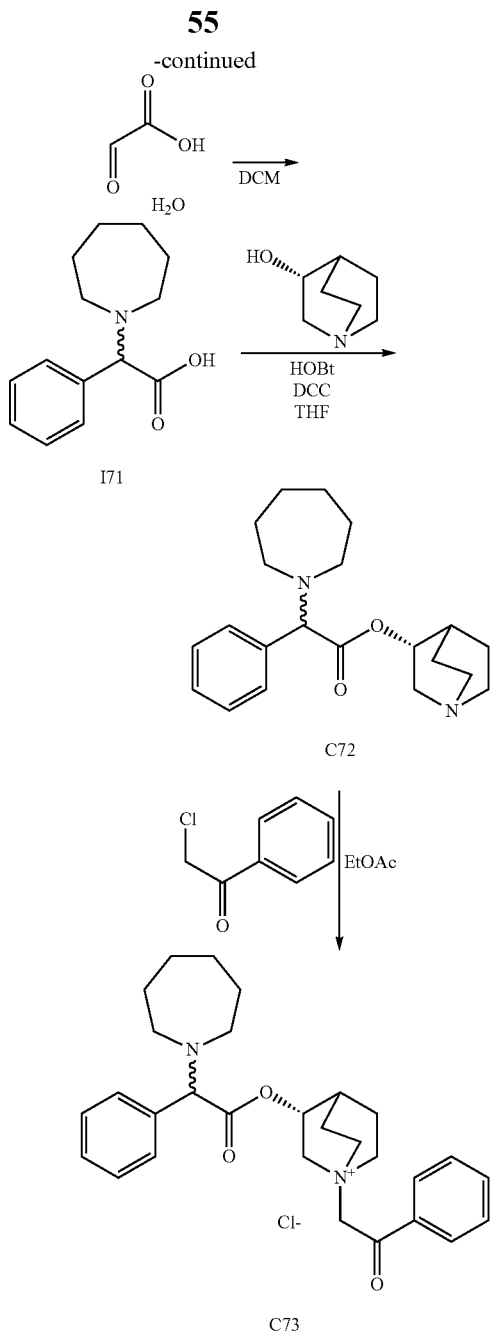

HOBT (375 mg, 2.45 mmol) and DCC (505 mg, 2.45 mmol) in THF (20 ml) was stirred at room temperature over a weekend. THF was evaporated, the crude was taken up with EtOAc and washed twice with 2M K₂CO₃ and then with brine. The organic phase was dried over Na₂SO₄, filtered and evaporated to dryness. The crude was purified by flash-chromatography (DCM/MeOH=95/5) to get (R)-quinuclidin-3-yl 2-(azepan-1-yl)-2-phenylacetate (110 mg, 15.7% yield) as a white solid.

Preparation of (3R)-3-(2-(azepan-1-yl)-2-phenylacetoxy)-1-(2-oxo-2-phenylethyl)-1-azoniabicyclo [2.2.2]octane chloride (C73)

2-Chloro-1-phenylethanone (46.9 mg, 0.30 mmol) was added to a solution of (R)-quinuclidin-3-yl 2-(azepan-1-yl)-2-phenylacetate (104 mg, 0.30 mmol) in ethyl acetate (3 ml). The reaction was stirred at room temperature overnight then Et₂O (2 mL) was added, the suspension was sonicated, filtered and dried under vacuum at 40° C. overnight to obtain the title compound (99 mg, 65.6% yield) as a white solid.

¹H NMR (300 MHz, DMSO-d6) ppm 7.91-8.08 (m, 2H) 7.70-7.84 (m, 1H) 7.56-7.65 (m, 2H) 7.25-7.49 (m, 5H) 5.13-5.39 (m, 2H) 4.59 and 4.61 (s, 1H) 4.06-4.30 (m, 1H) 3.48-3.83 (m, 4H) 2.58-2.79 (m, 4H) 2.25-2.33 and 2.33-2.42 (m, 1H) 1.76-2.20 (m, 4H) 1.40-1.70 (m, 8H).

UPLC-MS (ESI POS) 461.25 (M+).

Example 20

Preparation of (3R)-3-(2-((R)-2-methylpyrrolidin-1-yl)-2-phenylacetoxy)-1-(2-oxo-2-phenylethyl)-1-azoniabicyclo[2.2.2]octane chloride (C76)

Scheme 21

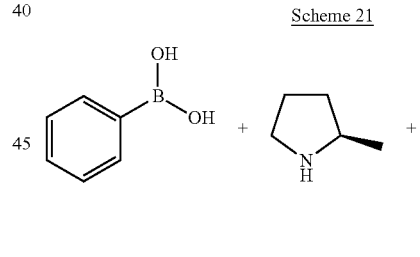

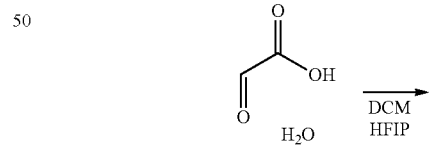

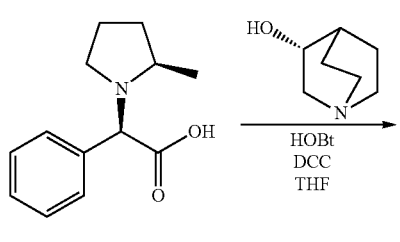

Preparation of 2-(azepan-1-yl)-2-phenylacetic acid (I71)

A mixture of phenylboronic acid (400 mg, 3.28 mmol), azepane (0.37 ml, 3.28 mmol) and 2-oxoacetic acid hydrate (302 mg, 3.28 mmol) dissolved in DCM (30 ml) was stirred at room temperature overnight. DCM was removed under vacuum and the crude was purified by flash chromatography (DCM/MeOH=8/2) to obtain the title compound (476 mg, 62.2% yield) as a white solid.

Preparation of (R)-quinuclidin-3-yl 2-(azepan-1-yl)-2-phenylacetate (C72)

A mixture of 2-(azepan-1-yl)-2-phenylacetic acid (476 mg, 2.04 mmol), (R)-quinuclidin-3-ol (311 mg, 2.45 mmol),

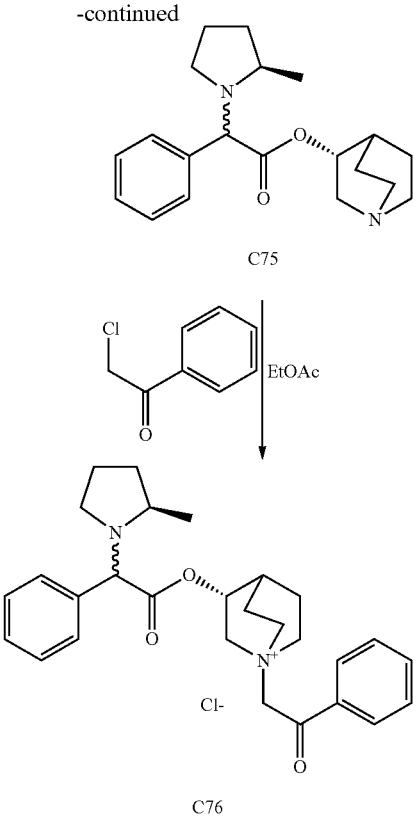

Preparation of (R)-2-(R)-2-Methylpyrrolidin-1-yl)-2-phenylacetic acid (I74)

(R)-2-Methylpyrrolidine (0.33 ml, 3.26 mmol) and phenylboronic acid (397 mg, 3.26 mmol) were sequentially added to a solution of 2-oxoacetic acid hydrate (300 mg, 3.26 mmol) in DCM (14.7 ml) and 1,1,1,3,3,3-hexafluoropropan-2-ol (1.6 ml). The mixture was stirred at room temperature for a day, then the solvent was evaporated and the crude was purified by flash chromatography (DCM/MeOH=8/2) to collect the title compound (615 mg, 86% yield) as a off-white solid.

$^1$H NMR (300 MHz, DMSO-d6) ppm 7.14-7.78 (m, 5H), 4.36 (s, 1H), 3.30 (tq, 1H), 3.03 (ddd, 1H), 2.69 (dt, 1H), 1.94-2.21 (m, 1H), 1.64-1.94 (m, 2H), 1.45-1.64 (m, 1H), 1.23 (d, 3H).

UPLC-MS (ESI POS) 220.0 (MH+).

Preparation of (R)-quinuclidin-3-yl 2-((R)-2-methylpyrrolidin-1-yl)-2-phenylacetate (C75)

To a suspension of (R)-2-((R)-2-methylpyrrolidin-1-yl)-2-phenylacetic acid 22c (150 mg, 0.68 mmol) in dry THF (6.8 ml), were added DCC (282 mg, 1.37 mmol), HOBT (185 mg, 1.37 mmol) and (R)-quinuclidin-3-ol (174 mg, 1.37 mmol). The mixture was stirred at room temperature under nitrogen for 24 hours. The pale yellow suspension was filtered washing with THF (5 ml) and the yellow solution was evaporated. The crude was purified by flash chromatography (DCM/MeOH=95/5 to 9/1 and then with DCM/MeOH/NH$_4$OH=95/5/0.2) to collect the title compound (48 mg, 21.4% yield) as a colorless oil.

$^1$H NMR (300 MHz, DMSO-d6) ppm 7.22-7.47 (m, 10H) 4.77 (dt, 1H) 4.62-4.72 (m, 1H) 4.54 (s, 1H) 4.37 (s, 1H) 3.13 (ddd, 1H) 2.90-3.07 (m, 2H) 2.55-2.86 (m, 10H) 2.45 (br. s., 1H) 2.31-2.44 (m, 1H) 2.18-2.29 (m, 1H) 1.76-2.00 (m, 5H) 1.41-1.72 (m, 10H) 1.13-1.41 (m, 5H) 0.95 (d, 3H) 0.91 (d, 3H).

UPLC-MS (ESI POS) 329.0 (MH+).

Preparation of (3R)-3-(2-((R)-2-methylpyrrolidin-1-yl)-2-phenylacetoxy)-1-(2-oxo-2-phenylethyl)-1-azoniabicyclo[2.2.2]octane chloride (C76)

(R)-Quinuclidin-3-yl 2-((R)-2-methylpyrrolidin-1-yl)-2-phenylacetate (24c) (44 mg, 0.13 mmol) was dissolved in a mixture ethyl acetate (0.9 ml) and acetonitrile (0.4 ml). 2-Chloro-1-phenylethanone (22.8 mg, 0.15 mmol) was added and the mixture was stirred at room temperature for 48 hours. The solution was evaporated and the residue was purified first by flash chromatography (DCM/MeOH=90/10 to 85/15) and then by trituration with Et$_2$O/DCM (about 5/1) to obtain the title compound (23 mg, 35.5% yield) as a pale yellow solid.

$^1$H NMR (300 MHz, DMSO-d6) ppm 7.91-8.10 (m, 2H), 7.70-7.83 (m, 1H), 7.54-7.70 (m, 2H), 7.22-7.52 (m, 5H), 5.23 and 5.26 (s, 2H), 5.24-5.34 (m, 1H), 5.13-5.22 (m, 1H), 4.53 and 4.66 (s, 1H), 4.02-4.29 (m, 1H), 3.48-3.85 (m, 5H), 2.62-3.09 (m, 2H), 2.31-2.42 (m, 1H), 1.49-2.31 (m, 7H), 1.28-1.46 (m, 1H), 0.95 and 0.99 (d, 3H).

UPLC-MS (ESI POS) 447.07 (M+).

Example 21

Preparation of (3R)-1-(2-oxo-2-phenylethyl)-3-(2-(2-oxopyrrolidin-1-yl)-2-phenylacetoxy)-1-azoniabicyclo[2.2.2]octane chloride (C80)

Scheme 22

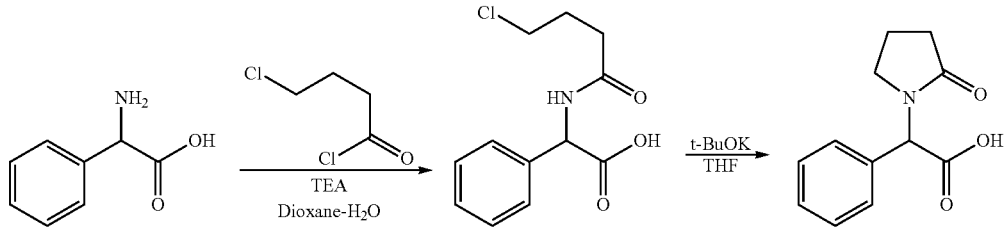

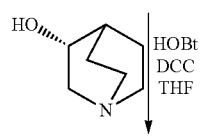

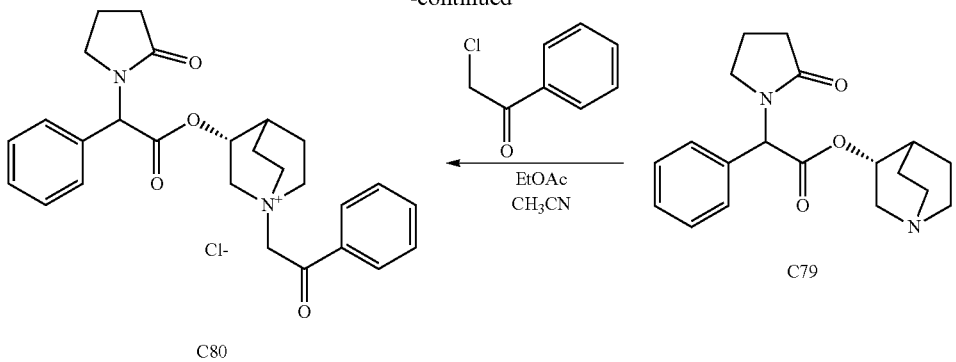

Preparation of 2-(4-chlorobutanamido)-2-phenylacetic acid (I77)

2-Amino-2-phenylacetic acid (1.00 g, 6.62 mmol) and TEA (2.77 ml, 19.8 mmol) were dissolved in a mixture of dioxane (13.2 ml) and water (13.2 ml). The mixture was cooled at 0° C. with an ice-bath and 4-chlorobutanoyl chloride (814 μl, 7.28 mmol) was added dropwise. The mixture was stirred at the same temperature for 1 hour and then dioxane was evaporated. The aqueous solution was acidified with 1N HCl and then was extracted three times with EtOAc (20 ml×3). The organic phase was dried (Na$_2$SO$_4$) and evaporated. The crude pale yellow oil was purified by flash chromatography (DCM/MeOH=9/1) and the collected compound was triturated with Et$_2$O (about 15 ml) to obtain the title compound (658 mg, 38.9% yield) as a white solid.

$^1$H NMR (300 MHz, DMSO-d6) ppm 8.59 (d, 1H), 7.09-7.57 (m, 5H), 5.33 (d, 1H), 3.63 (t, 2H), 2.24-2.45 (m, 2H), 1.94 (quin, 2H).

UPLC-MS (ESI) 255.9 m/z (MH+).

Preparation of 2-(2-oxopyrrolidin-1-yl)-2-phenylacetic acid (I78)

2-(4-Chlorobutanamido)-2-phenylacetic acid (650 mg, 2.54 mmol) was dissolved in dry THF (8.5 ml) and the solution was cooled to 0° C. with an ice-bath stirring under nitrogen atmosphere. Potassium tert-butoxide (599 mg, 5.34 mmol) was added in three portions and a white suspension was obtained. The mixture was stirred at the same temperature for 15 minutes. 1N HCl was added dropwise till pH 2-3 and than the mixture was diluted with water (10 ml) and extracted three times with EtOAc (15 ml×3). The organic phase was dried (Na$_2$SO$_4$) and evaporated to obtain the title compound (352 mg, 63.2% yield) as a pale yellow spongy sticky solid.

$^1$H NMR (300 MHz, DMSO-d6) ppm 13.05 (br. s., 1H) 7.32-7.47 (m, 3H) 7.21-7.32 (m, 2H) 5.68 (s, 1H) 3.51 (td, 1H) 2.86 (td, 1H) 2.20-2.34 (m, 2 μl) 1.70-2.03 (m, 2H).

UPLC-MS (ESI) 219.9 m/z (MH+).

Preparation of (R)-quinuclidin-3-yl 2-(2-oxopyrrolidin-1-yl)-2-phenylacetate (C79)

A mixture of 2-(2-oxopyrrolidin-1-yl)-2-phenylacetic acid (345 mg, 1.57 mmol), DCC (649 mg, 3.15 mmol), HOBT (425 mg, 3.15 mmol) and (R)-quinuclidin-3-ol (400 mg, 3.15 mmol) in dry THF (15.7 ml) was stirred at room temperature for 24 hours. The yellow suspension was filtered washing the white solid with THF. The yellow solution was evaporated and the crude was purified by flash chromatography (DCM/MeOH=96/4+0.4% NH$_4$OH) to collect the title compound (482 mg, 93% yield) as a pale yellow oil.

$^1$H NMR (300 MHz, DMSO-d6) ppm 7.17-7.50 (m, 5H), 5.75 (s, 1H), 4.74-4.91 (m, 1H), 3.43-3.54 (m, 1H), 3.05-3.20 (m, 1H), 2.92 (td, 1H), 2.53-2.76 (m, 5H), 2.30 (t, 2H), 1.77-2.05 (m, 3H), 1.11-1.74 (m, 4H);

UPLC-MS (ESI) 329.0 m/z (MH+).

Preparation of (3R)-1-(2-oxo-2-phenylethyl)-3-(2-(2-oxopyrrolidin-1-yl)-2-phenylacetoxy)-1-azoniabicyclo[2.2.2]octane chloride (C80)

2-Chloro-1-phenylethanone (62.1 mg, 0.40 mmol) was added to a solution of (R)-quinuclidin-3-yl 2-(2-oxopyrrolidin-1-yl)-2-phenylacetate (120 mg, 0.36 mmol) in EtOAc (2.4 ml) and acetonitrile (1.2 ml). The pale yellow solution was stirred at room temperature for three days. The solvent was evaporated and the crude was purified by flash chromatography (DCM/MeOH=9/1) to collect the title compound (118 mg, 66.9% yield) as an off-white spongy solid.

$^1$H NMR (300 MHz, DMSO-d6) ppm 7.92-8.09 (m, 2H), 7.70-7.83 (m, 1H), 7.53-7.70 (m, 2H), 7.23-7.53 (m, 5H), 5.83 (s, 1H), 5.26-5.39 (m, 3H), 4.10-4.43 (m, 1H), 3.40-3.97 (m, 6H), 2.85-3.08 (m, 1H), 2.26-2.46 (m, 3H), 1.63-2.15 (m, 6H).

UPLC-MS (ESI) 447.21 m/z (M+).

Example 22

Preparation of (3R)-3-(2-(3-fluorophenyl)-2-(piperidin-1-yl)acetoxy)-1-(2-oxo-2-phenylethyl)-1-azoniabicyclo[2.2.2]octane bromide (C 84)

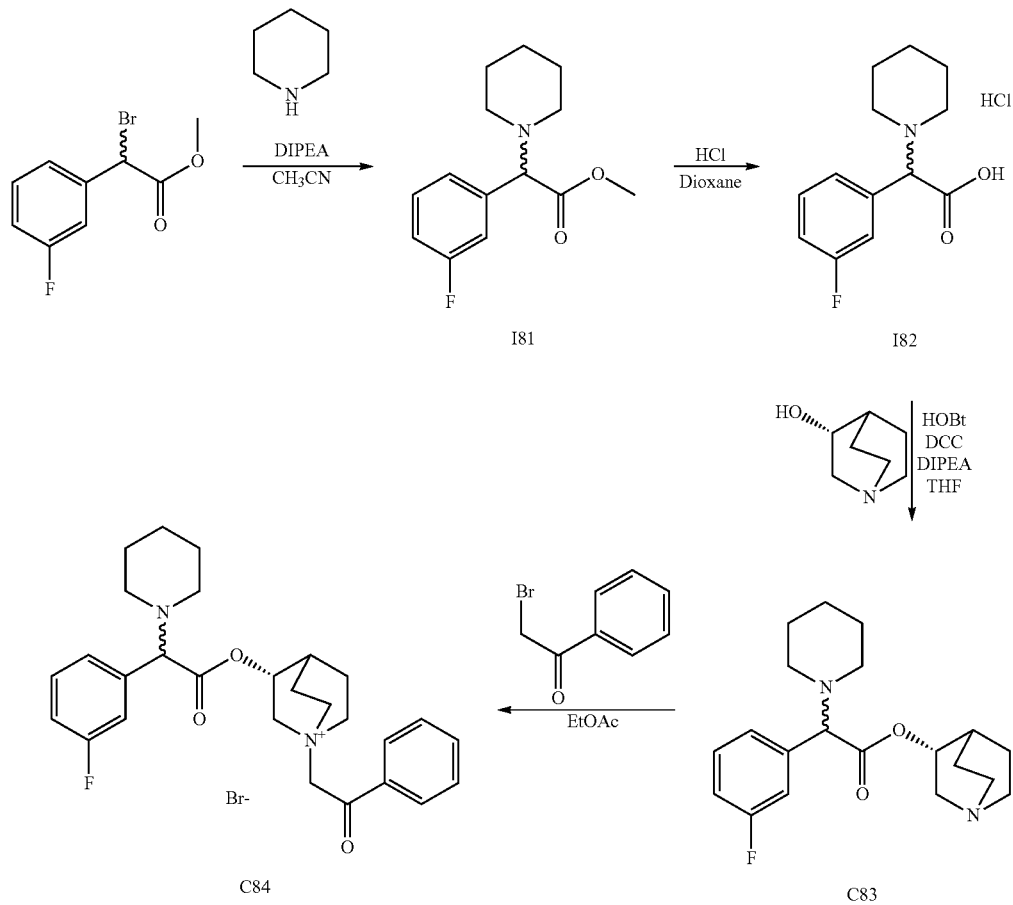

Preparation of methyl 2-(3-fluorophenyl)-2-(piperidin-1-yl)acetate (I81)

Methyl 2-bromo-2-(3-fluorophenyl)acetate (310 mg, 1.25 mmol), piperidine (0.15 ml, 1.51 mmol), and DIPEA (0.26 ml, 1.51 mmol) were dissolved in acetonitrile (15 ml) and stirred at room temperature for 16 hours. The solvent was evaporated and the crude was purified by flash chromatography (petroleum ether/EtOAc=9/1) to afford methyl 2-(3-fluorophenyl)-2-(piperidin-1-yl)acetate (224 mg, 71% yield) as a colorless oil.

UPLC-MS (ESI) 252.1 m/z (MH+).

Preparation of 2-(3-fluorophenyl)-2-(piperidin-1-yl) acetic acid hydrochloride (I82)

Methyl 2-(3-fluorophenyl)-2-(piperidin-1-yl)acetate (224 mg, 0.89 mmol) and 37% HCl (813 µl, 26.7 mmol) were dissolved in dioxane (3 ml) and stirred under microwave irradiation at 100° C. for 6 hours. The solvents were evaporated and the residue was triturated with Et$_2$O and sonicated. The solid was collected by suction filtration, washed with Et$_2$O and dried under vacuum overnight to collect 2-(3-fluorophenyl)-2-(piperidin-1-yl)acetic acid hydrochloride (230 mg, 94% yield).

$^1$H NMR (300 MHz, DMSO-d6) ppm 7.58 (td, 1H), 7.50 (ddd, 1H), 7.44 (ddd, 1H), 7.38 (dddd, 1H), 5.31 (s, 1H), 2.90-3.07 (m, 4H), 1.39-1.92 (m, 6H).

Preparation of (R)-quinuclidin-3-yl 2-(3-fluorophenyl)-2-(piperidin-1-yl)acetate (C83)

2-(3-Fluorophenyl)-2-(piperidin-1-yl)acetic acid hydrochloride (225 mg, 0.82 mmol), DCC (339 mg, 1.64 mmol), and HOBT (252 mg, 1.64 mmol) were dissolved in dry THF (9 ml). (R)-quinuclidin-3-ol (314 mg, 2.47 mmol) was added and the reaction mixture was stirred at room temperature for 16 hours. THF was evaporated, the residue was taken up with EtOAc and washed with sat. NaHCO$_3$, water and brine. The organic layer was dried over Na$_2$SO$_4$, filtered and evaporated to dryness. The crude was purified by flash chromatography (DCM/MeOH=9/1) to obtain (R)-quinuclidin-3-yl 2-(3-fluorophenyl)-2-(piperidin-1-yl)acetate (166 mg, 58.3 yield).

$^1$H NMR (300 MHz, DMSO-d6) ppm 7.31-7.53 (m, 1H), 7.01-7.31 (m, 3H), 4.73 (td, 1H), 4.15 (s, 1H), 2.98-3.20 (m, 1H), 2.55-2.78 (m, 4H), 2.30-2.47 (m, 5H), 1.74-1.85 and 1.85-1.95 (m, 1H), 1.01-1.68 (m, 10H).

Preparation of (3R)-3-(2-(3-fluorophenyl)-2-(piperidin-1-yl)acetoxy)-1-(2-oxo-2-phenylethyl)-1-azoniabicyclo[2.2.2]octane bromide (C84)

(R)-Quinuclidin-3-yl 2-(3-fluorophenyl)-2-(piperidin-1-yl)acetate (164 mg, 0.47 mmol) and 2-bromo-1-phenylethanone (104 mg, 0.52 mmol) were dissolved in acetonitrile (5 ml) and stirred at room temperature for 16 hours. The solvent was evaporated and the crude was triturated with Et$_2$O, filtered under suction and washed with EtOAc and Et$_2$O (1/1) to obtain (3R)-3-(2-(3-fluorophenyl)-2-(piperidin-1-yl)acetoxy)-1-(2-oxo-2-phenylethyl)-1-azoniabicyclo[2.2.2]octane bromide (180.5 mg; 69.9% yield) as a white solid.

$^1$H NMR (300 MHz, DMSO-d6) ppm 7.91-8.08 (m, 2H), 7.71-7.88 (m, 1H), 7.56-7.70 (m, 2H), 7.38-7.53 (m, 1H), 7.08-7.37 (m, 3H), 5.24-5.31 (m, 1H), 5.23 and 5.24 (br. s., 2H), 4.30 and 4.31 (s, 1H), 4.04-4.23 (m, 1H), 3.52-3.89 (m, 5H), 2.22-2.47 (m, 5H), 1.76-2.17 (m, 4H), 1.28-1.63 (m, 6H);

UPLC-MS (ESI) 465.18 m/z (M+).

Example 23

Preparation of (3R)-1-(2-oxo-2-phenylethyl)-3-(2-(piperidin-1-yl)-2-p-tolylacetoxy)-1-azoniabicyclo[2.2.2]octane trifluoroacetate trifluoroacetate anion (C88)

Preparation of methyl 2-(piperidin-1-yl)-2-p-tolylacetate (I85)

To a solution of methyl 2-bromo-2-p-tolylacetate (2.50 g, 10.3 mmol) in acetonitrile, was added piperidine (2.06 ml, 20.6 mmol) and the mixture was reacted for 2 hours at room temperature. The solvent was evaporated and the resulting crude was portioned between water and EtOAc. The aqueous phase was extracted with EtOAc, the organic phases were combined, dried over Na$_2$SO$_4$, filtered and evaporated to dryness. The crude was purified by flash chromatography (petroleum ether/EtOAc=9/1) to obtain methyl 2-(piperidin-1-yl)-2-p-tolylacetate (273 mg, 21% yield) as a colourless oil.

UPLC-MS (ESI) 248.2 m/z (MH+).

Preparation of 2-(piperidin-1-yl)-2-p-tolylacetic acid hydrochloride (I86)

To a solution of methyl 2-(piperidin-1-yl)-2-p-tolylacetate (273 mg, 1.10 mmol) in dioxane (2 ml), was added 37% HCl (3.35 ml, 110 mmol). The reaction was heated under microwave irradiation at 100° C. for 4 hours. The solvents were evaporated and the residue was triturated with Et$_2$O to collect 2-(piperidin-1-yl)-2-p-tolylacetic acid hydrochloride (242 mg, 81% yield) as a white solid.

$^1$H NMR (300 MHz, DMSO-d6) ppm 10.27 (br. s., 1H), 7.39-7.52 (m, 2H), 7.21-7.39 (m, 2H), 5.19 (s, 1H), 2.80-3.18 (m, 4H), 2.34 (s, 3H), 1.79 (br. s., 4H), 1.50 (br. s., 2H).

Scheme 24

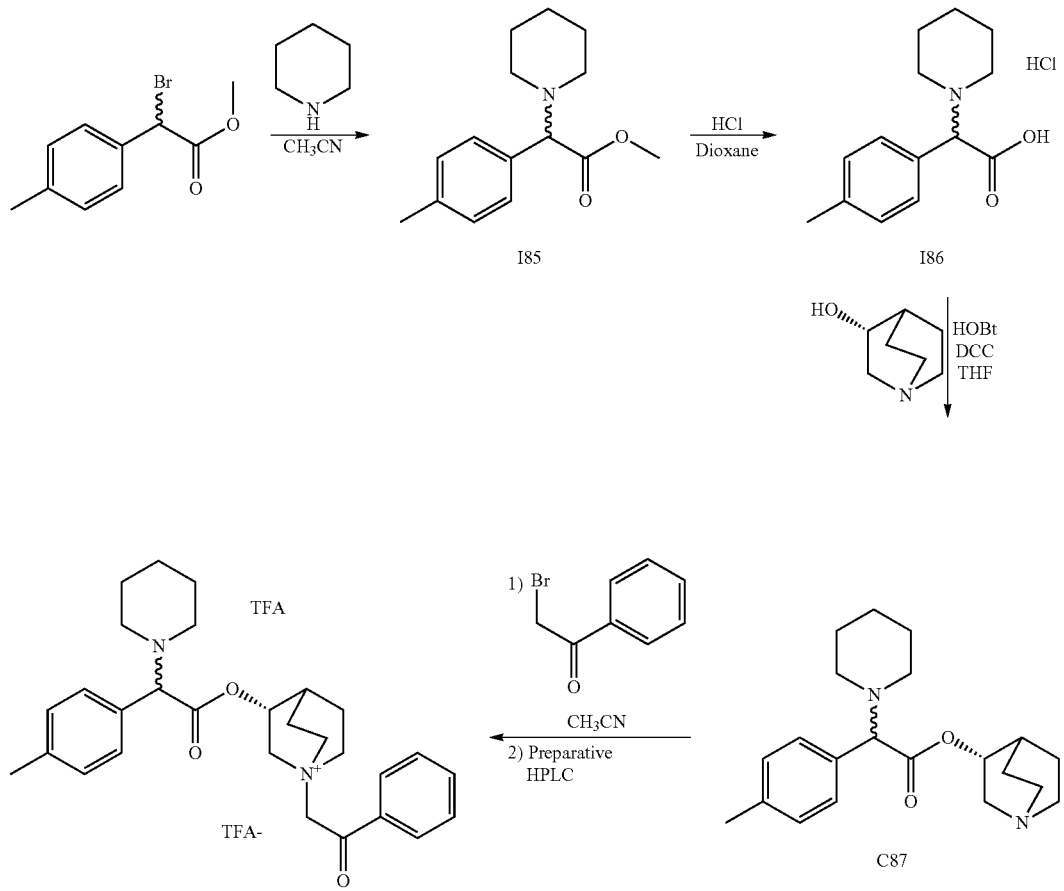

Preparation of (R)-quinuclidin-3-yl 2-(piperidin-1-yl)-2-p-tolylacetate (C87)

2-(Piperidin-1-yl)-2-p-tolylacetic acid hydrochloride (242 mg, 0.90 mmol), DCC (370 mg, 1.79 mmol) and HOBT (275 mg, 1.79 mmol) were dissolved in dry THF (10 ml). (R)-quinuclidin-3-ol (342 mg, 2.69 mmol) was added and the mixture was stirred at room temperature for 16 hours. THF was evaporated and the residue was taken up with EtOAc and washed with sat. NaHCO$_3$, water and brine. The organic layer was recovered, dried over Na$_2$SO$_4$, filtered and evaporated. The crude was purified by flash chromatography (DCM/MeOH=9/1) to obtain (R)-quinuclidin-3-yl 2-(piperidin-1-yl)-2-p-tolylacetate (169 mg, 55% yield) as a colourless oil.

$^1$H NMR (300 MHz, DMSO-d6) ppm 7.23-7.38 (m, 2H), 7.06-7.23 (m, 2H), 4.56-4.78 (m, 1H), 4.00 and 4.01 (s, 1H), 3.03 and 3.09 (ddd, 1H), 2.54-2.77 (m, 4H), 2.39-2.47 (m, 1H), 2.30-2.39 (m, 4H), 2.29 (s, 3H), 1.73-1.82 and 1.85-1.93 (m, 1H), 1.08-1.74 (m, 10H)

Preparation of (3R)-1-(2-oxo-2-phenylethyl)-3-(2-(piperidin-1-yl)-2-p-tolylacetoxy)-1-azoniabicyclo[2.2.2]octane trifluoroacetate trifluoroacetate anion (C88)

(R)-Quinuclidin-3-yl 2-(piperidin-1-yl)-2-p-tolylacetate (160 mg, 0.47 mmol) and 2-bromo-1-phenylethanone (102 mg, 0.51 mmol) were dissolved in acetonitrile (5 ml) and stirred at room temperature for 16 hours. The solvent was evaporated and the crude residue was triturated with Et$_2$O and collected by suction filtration. The solid was then purified by flash chromatography (DCM/MeOH=9/1) and finally by preparative HPLC to obtain (3R)-1-(2-oxo-2-phenylethyl)-3-(2-(piperidin-1-yl)-2-p-tolylacetoxy)-1-azoniabicyclo[2.2.2]octane trifluoroacetate trifluoroacetate anion (114 mg, 35.4% yield) as a white powder.

$^1$H NMR (300 MHz, DMSO-d6) ppm 7.91-8.02 (m, 2H), 7.71-7.81 (m, 1H), 7.55-7.67 (m, 2H), 7.42-7.51 (m, 2H), 7.29-7.42 (m, 2H), 5.30-5.44 (m, 2H), 5.16 and 5.19 (s, 2H), 4.01-4.29 (m, 1H), 3.36-3.91 (m, 5H), 2.69-3.11 (m, 4 H), 2.36 (s, 3H), 2.22 and 2.45 (br. s., 1H), 1.24-2.16 (m, 10H);

UPLC-MS (ESI) 461.13 m/z (M+).

Example 24

Preparation of (3R)-3-(2-(4-methoxyphenyl)-2-(piperidin-1-yl)acetoxy)-1-(2-oxo-2-phenylethyl)-1-azoniabicyclo[2.2.2]octane trifluoroacetate, trifluoroacetate anion (C92)

Scheme 25

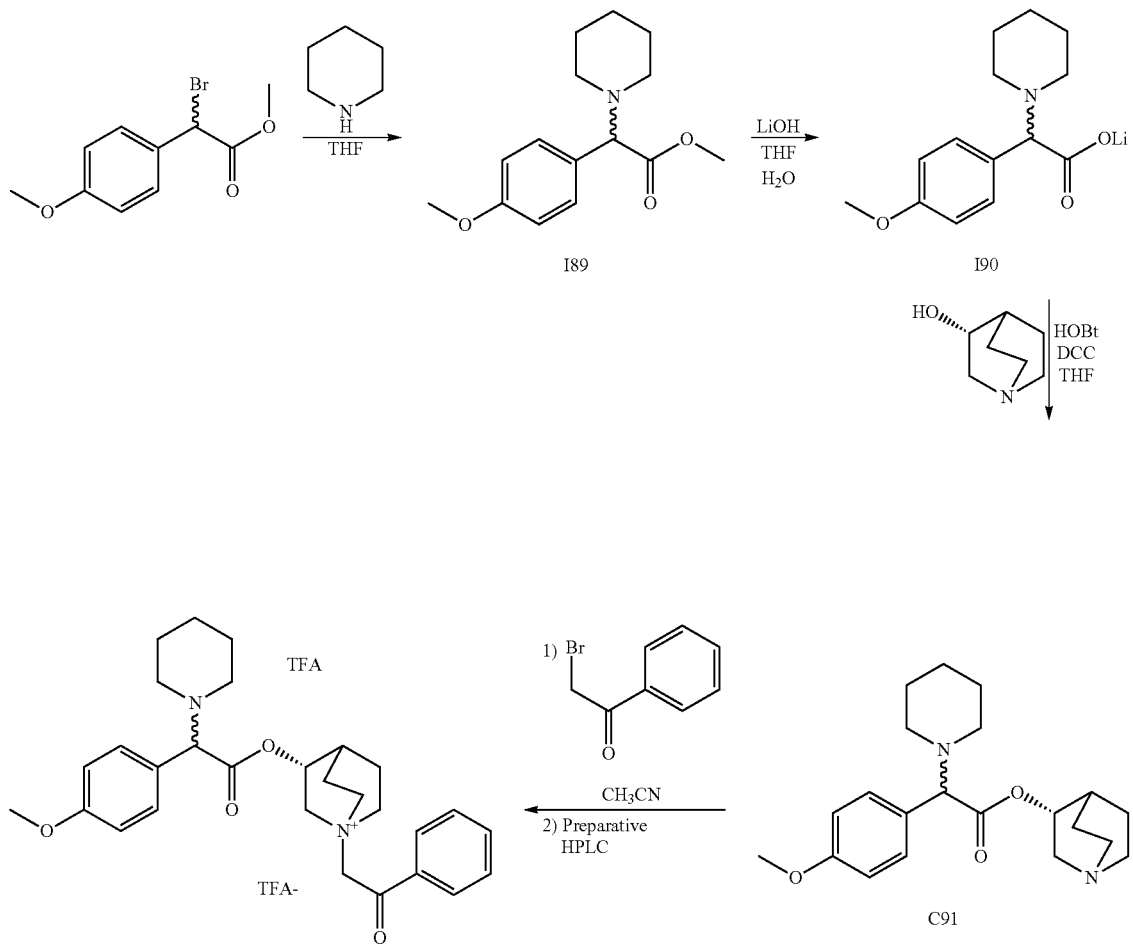

Preparation of methyl 2-(4-methoxyphenyl)-2-(piperidin-1-yl)acetate (I89)

To a solution of methyl 2-bromo-2-(4-methoxyphenyl)acetate (2.5 g, 9.65 mmol) in THF (50 ml), was added piperidine (1.64 g, 19.3 mmol) and the mixture reacted for 2 hours at room temperature. The solvent was evaporated and the resulting crude was portioned between water and EtOAc. The aqueous phase was extracted with EtOAc, the organic phases were combined, dried over $Na_2SO_4$, filtered and evaporated to dryness. The crude was purified by flash chromatography (petroleum ether/EtOAc=85/15) to obtain (methyl 2-(4-methoxyphenyl)-2-(piperidin-1-yl)acetate (1.81 g, 71.4% yield).

UPLC-MS (ESI) 264.2 m/z (MH+).

Preparation of lithium 2-(4-methoxyphenyl)-2-(piperidin-1-yl)acetate (I90)

Methyl 2-(4-methoxyphenyl)-2-(piperidin-1-yl)acetate (400 mg, 1.52 mmol) was dissolved in THF/water (12 ml/4 ml). Lithium hydroxide hydrate (127 mg, 3.04 mmol) was added and the solution was stirred at room temperature for 8 hours. Then a second portion of lithium hydroxide hydrate (63.7 mg, 1.52 mmol) was added and the mixture was stirred at 40° C. for 16 hours, then at 50° C. for 7 hours. The solvents were evaporated, the residue was taken up with $Et_2O$ and the insoluble were filtered off. The clear solution was evaporated to obtain lithium 2-(4-methoxyphenyl)-2-(piperidin-1-yl)acetate (384 mg, 99% yield) as a white solid.

Preparation of (R)-quinuclidin-3-yl 2-(4-methoxyphenyl)-2-(piperidin-1-yl)acetate (C91)

Lithium 2-(4-methoxyphenyl)-2-(piperidin-1-yl)acetate (384 mg, 1.50 mmol), DCC (621 mg, 3.01 mmol), and HOBT (461 mg, 3.01 mmol) were dissolved in dry THF (16 ml). (R)-quinuclidin-3-ol (574 mg, 4.51 mmol) was added and the mixture was stirred at room temperature for 16 hours. THF was evaporated and the crude was dissolved in EtOAc, washed with sat. $NaHCO_3$, water and brine. The organic layer was dried over $Na_2SO_4$, filtered and evaporated. The crude was purified by flash chromatography (DCM/MeOH/$NH_4OH$=9/1/0.02) to obtain (R)-quinuclidin-3-yl 2-(4-methoxyphenyl)-2-(piperidin-1-yl)acetate (207 mg, 38.4% yield) as a colourless oil.

$^1$H NMR (300 MHz, DMSO-d6) ppm 7.23-7.37 (m, 2H), 6.80-6.99 (m, 2H), 4.55-4.84 (m, 1H), 3.97 (s, 1H), 3.74 and 3.75 (s, 3H), 3.02 and 3.07 (ddd, 1H), 2.54-2.70 (m, 5H), 2.17-2.47 (m, 4H), 1.72-1.81 and 1.84-1.93 (m, 1H), 1.06-1.70 (m, 10H).

Preparation of (3R)-3-(2-(4-methoxyphenyl)-2-(piperidin-1-yl)acetoxy)-1-(2-oxo-2-phenylethyl)-1-azoniabicyclo[2.2.2]octane trifluoroacetate, trifluoroacetate anion (C92)

(R)-Quinuclidin-3-yl 2-(4-methoxyphenyl)-2-(piperidin-1-yl)acetate (207 mg, 0.58 mmol) and 2-bromo-1-phenylethanone (126 mg, 0.63 mmol) were dissolved in acetonitrile (6 ml) and stirred at room temperature for 18 hours. The solvent was evaporated and the residue was triturated with $Et_2O$ and then purified by flash chromatography (DCM/MeOH:88/22) and preparative HPLC to collect the title compound (51 mg, 12.5% yield) as a colourless oil.

$^1$H NMR (300 MHz, DMSO-d6) ppm 10.48 (br. s., 1H), 7.89-8.11 (m, 2H), 7.69-7.84 (m, 1H), 7.56-7.69 (m, 2H), 7.42-7.56 (m, 2H), 6.91-7.25 (m, 2H), 5.32-5.54 (m, 2H), 5.17 and 5.20 (s, 2H), 3.99-4.32 (m, 1H), 3.81 (s, 3H), 3.37-3.74 (m, 5H), 2.61-3.15 (m, 4H), 2.19-2.30 and 2.40-2.55 (m, 1H), 1.21-2.14 (m, 10H);

UPLC-MS (ESI) 477.23 m/z (M+).

Example 25

Preparation of (3R)-3-(2-(4-chlorophenyl)-2-(piperidin-1-yl)acetoxy)-1-(2-oxo-2-phenylethyl)-1-azoniabicyclo[2.2.2]octane bromide (C95)

Scheme 26

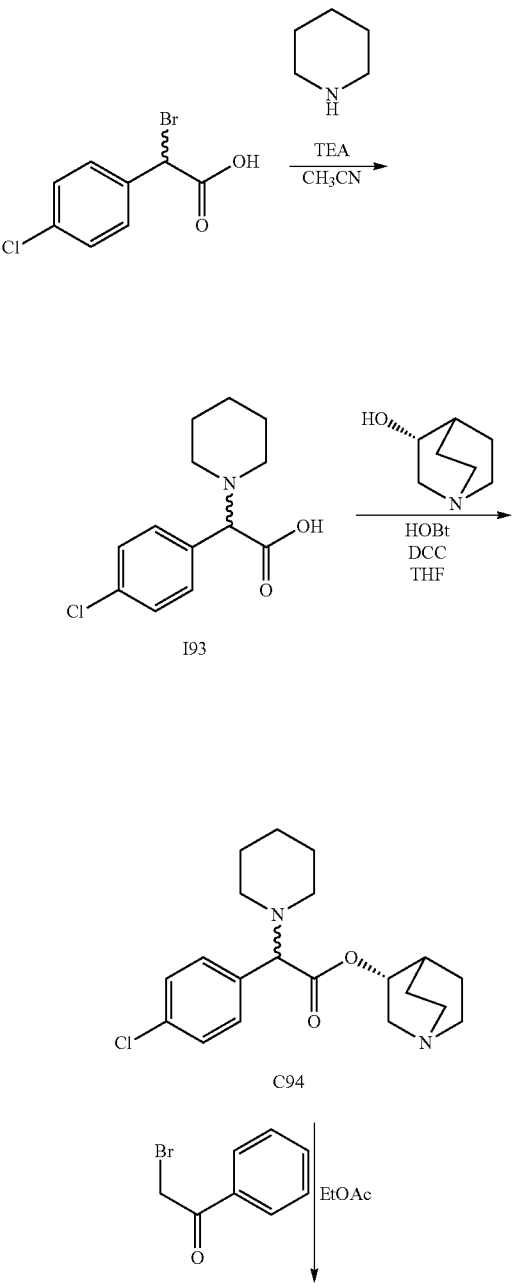

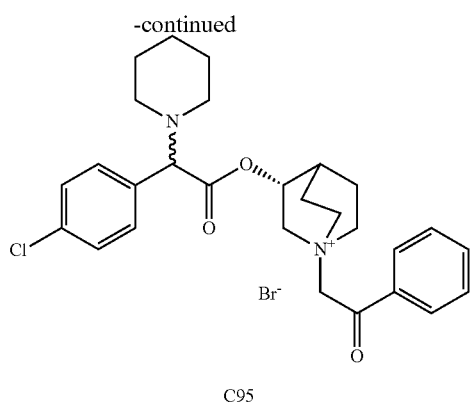

C95

Preparation of 2-(4-chlorophenyl)-2-(piperidin-1-yl) acetic acid (I93)

2-Bromo-2-(4-chlorophenyl)acetic acid (300 mg, 1.20 mmol), piperidine (125 µl, 1.26 mmol) and TEA (503 µl, 3.61 mmol) were dissolved in acetonitrile (6 ml). The resulting reaction was stirred at room temperature for 48 hours. Acetonitrile was evaporated, the residue was triturated with acetonitrile/petroleum ether (9/1) and filtered by suction filtration to collect 2-(4-chlorophenyl)-2-(piperidin-1-yl)acetic acid (190 mg, 62.3% yield) as a white solid.

Preparation of (R)-quinuclidin-3-yl 2-(4-chlorophenyl)-2-(piperidin-1-yl)acetate (C94)

2-(4-Chlorophenyl)-2-(piperidin-1-yl)acetic acid (190 mg, 0.75 mmol), DCC (309 mg, 1.50 mmol), and HOBT (229 mg, 1.50 mmol) were dissolved in dry THF (8 ml). (R)-quinuclidin-3-ol (286 mg, 2.25 mmol) was added and the reaction was stirred at room temperature for 16 hours. THF was evaporated and the residue was dissolved in EtOAc and washed with 1M NaHCO$_3$, water and brine. The organic layer was separated, dried over Na$_2$SO$_4$, filtered and evaporated. The crude compound was purified by flash chromatography (DCM/MeOH/NH$_4$OH=9 5/5/0.1) to obtain (R)-quinuclidin-3-yl 2-(4-chlorophenyl)-2-(piperidin-1-yl)acetate (167 mg, 61.5% yield) as a colorless oil.

$^1$H NMR (300 MHz, DMSO-d6) ppm 7.33-7.47 (m, 4H), 4.57-4.95 (m, 1H), 4.12 (s, 1H), 3.04 and 3.09 (ddd, 1H), 2.56-2.78 (m, 4H), 2.18-2.47 (m, 5H), 1.72-1.83 and 1.85-1.95 (m, 1H), 1.09-1.70 (m, 10H).

Preparation of (3R)-3-(2-(4-chlorophenyl)-2-(piperidin-1-yl)acetoxy)-1-(2-oxo-2-phenylethyl)-1-azoniabicyclo[2.2.2]octane bromide (C95)

(R)-quinuclidin-3-yl 2-(4-chlorophenyl)-2-(piperidin-1-yl)acetate (100 mg, 0.28 mmol) and 2-bromo-1-phenylethanone (60.3 mg, 0.30 mmol) were dissolved in acetonitrile (4 ml) and stirred at room temperature for 16 hours. The solvent was evaporated and the resulting residue was purified by flash chromatography (DCM/MeOH=9/1) to obtain (3R)-3-(2-(4-chlorophenyl)-2-(piperidin-1-yl)acetoxy)-1-(2-oxo-2-phenylethyl)-1-azoniabicyclo[2.2.2]octane bromide (98 mg, 63.3% yield) as white powder.

$^1$H NMR (300 MHz, DMSO-d6) ppm 7.94-8.03 (m, 2H) 7.71-7.81 (m, 1H) 7.57-7.67 (m, 2H) 7.41-7.51 (m, 4H) 5.14-5.29 (m, 3H) 4.24-4.30 (m, 1H) 4.05-4.21 (m, 1H) 3.52-3.82 (m, 5H) 2.34-2.45 (m, 4H) 2.20-2.34 (m, 1H) 1.78-2.16 (m, 4H) 1.29-1.66 (m, 6H);

UPLC-MS (ESI) 481.25 m/z (M+).

Example 26

Preparation of 3R)-3-(2-(4-fluorophenyl)-2-(piperidin-1-yl)acetoxy)-1-(2-oxo-2-phenylethyl)-1-azoniabicyclo[2.2.2]octane chloride (C99)

Scheme 27

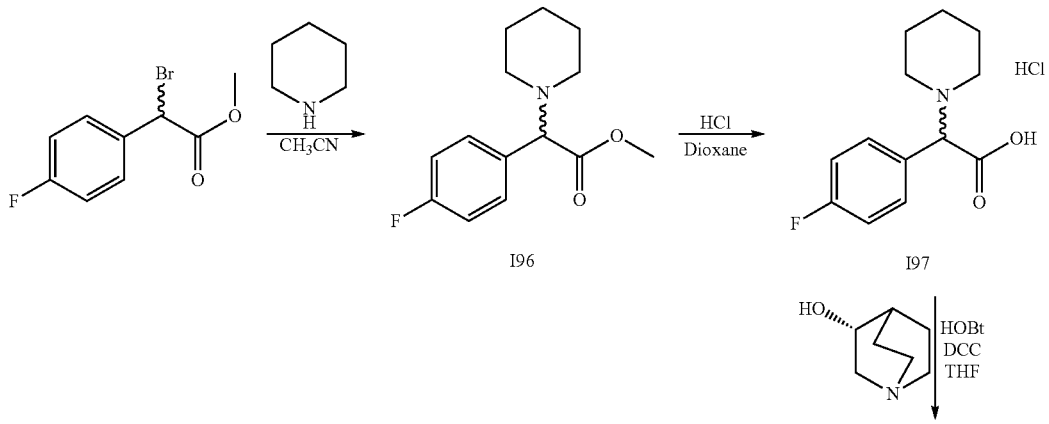

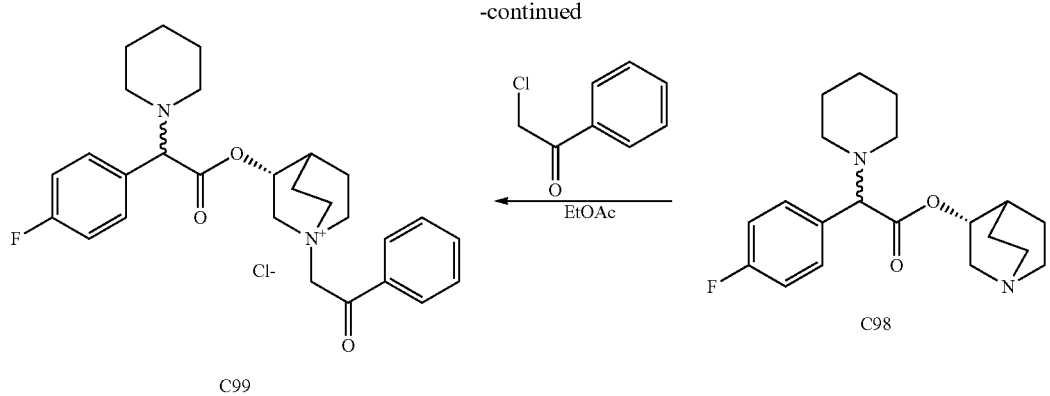

Preparation of methyl 2-(4-fluorophenyl)-2-(piperidin-1-yl)acetate (I96)

Methyl 2-bromo-2-(4-fluorophenyl)acetate (538 mg, 2.18 mmol) was dissolved in CH₃CN (6.6 ml) and piperidine (258 µl, 2.61 mmol) and N-ethyl-N-isopropylpropan-2-amine (456 µl, 2.61 mmol) were added sequentially. The solution was stirred at room temperature for 3 hours, then the solvent was evaporated and the crude was purified with flash chromatography (Petroleum ether/EtOAc=9/1) to collect methyl 2-(4-fluorophenyl)-2-(piperidin-1-yl)acetate (320 mg, 58.5% yield) as a colourless oil.

Preparation of 2-(4-fluorophenyl)-2-(piperidin-1-yl) acetic acid hydrochloride (I97)

37% Hydrogen chloride (4.18 ml, 50.9 mmol) was added to a solution of methyl 2-(4-fluorophenyl)-2-(piperidin-1-yl)acetate (320 mg, 1.27 mmol) in dioxane (5 ml). The reaction was stirred under microwave irradiation at 100° C. for 5 hours. The solvent was evaporated and the solid triturated with acetonitrile to obtain 2-(4-fluorophenyl)-2-(piperidin-1-yl)acetic acid hydrochloride (255 mg, 73% yield) as a white solid.

Preparation of (R)-quinuclidin-3-yl 2-(4-fluorophenyl)-2-(piperidin-1-yl)acetate (C98)

2-(4-Fluorophenyl)-2-(piperidin-1-yl)acetic acid hydrochloride (255 mg, 0.93 mmol) was dissolved in dry THF (10 ml) and (R)-quinuclidin-3-ol (355 mg, 2.79 mmol), DCC (384 mg, 1.86 mmol), HOBt (285 mg, 1.86 mmol) were added. The mixture was stirred at room temperature for 16 hours. THF was evaporated and the residue was taken up with EtOAc and washed with sat. NaHCO₃, water and brine. The organic phase was dried over Na₂SO₄, filtered and evaporated. The crude was purified by flash chromatography (DCM/MeOH/NH₄OH=98/2/0.2) to obtain (R)-quinuclidin-3-yl 2-(4-fluorophenyl)-2-(piperidin-1-yl)acetate (126 mg, 39.0% yield) as a white solid.

Preparation of (3R)-3-(2-(4-fluorophenyl)-2-(piperidin-1-yl)acetoxy)-1-(2-oxo-2-phenylethyl)-1-azoniabicyclo[2.2.2]octane chloride (C99)

2-Chloro-1-phenylethanone (29.5 mg, 0.19 mmol) was added to a solution of (R)-quinuclidin-3-yl 2-(4-fluorophenyl)-2-(piperidin-1-yl)acetate (60 mg, 0.17 mmol) in EtOAc (3 ml). 2-Chloro-1-phenylethanone (8.85 mg, 0.06 mmol) were added and stirring was kept for 4 additional hours. Et₂O was added and the precipitate was collected by suction filtration to obtain (3R)-3-(2-(4-fluorophenyl)-2-(piperidin-1-yl)acetoxy)-1-(2-oxo-2-phenylethyl)-1-azoniabicyclo[2.2.2]octane chloride (49.9 mg, 57.5% yield) as a gummy yellow solid.

¹H NMR (300 MHz, DMSO-d6) ppm 7.91-8.09 (m, 2H), 7.69-7.80 (m, 1H), 7.56-7.69 (m, 2H), 7.39-7.55 (m, 2H), 7.10-7.30 (m, 2H), 5.24 and 5.26 (s, 2H), 5.10-5.23 (m, 1H), 4.24 and 4.25 (s, 1H), 4.09-4.22 (m, 1H), 3.51-3.82 (m, 5H), 2.20-2.45 (m, 4H), 1.71-2.16 (m, 5H), 1.33-1.61 (m, 6H)

UPLC-MS (ESI) 465.24 m/z (MH+).

Example 27

Preparation of (3R)-1-(2-(4-chlorophenyl)-2-oxoethyl)-3-(2-phenyl-2-(piperidin-1-yl)acetoxy)-1-azoniabicyclo[2.2.2]octane bromide (C100)

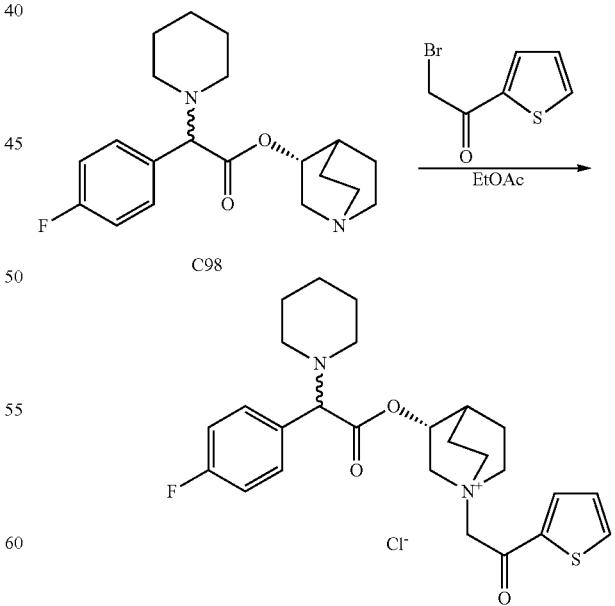

2-Chloro-1-(thiophen-2-yl)ethanone (30.6 mg, 0.19 mmol) was added to a solution of (R)-quinuclidin-3-yl 2-(4- fluorophenyl)-2-(piperidin-1-yl)acetate (60 mg, 0.17 mmol) in EtOAc (3 ml). The reaction was stirred at room temperature for 16 hours. Et₂O was added the precipitate was collected by filtration and purified by flash chromatography (DCM/MeOH/NH₄OH=97/3/0.3) to obtain (3R)-3-(2-(4-fluorophenyl)-2-(piperidin-1-yl)acetoxy)-1-(2-oxo-2-(thiophen-2-yl) ethyl)-1-azoniabicyclo[2.2.2]octane chloride (23 mg, 26.2% yield) as a white solid.

¹H NMR (300 MHz, DMSO-d6) ppm 8.18-8.31 (m, 2H) 8.03-8.18 (m, 1H) 7.79 (br. s., 1H) 7.40-7.62 (m, 1H) 7.31-7.40 (m, 2H) 7.03-7.31 (m, 1H) 5.06-5.41 (m, 2H) 3.97-4.31 (m, 2H) 3.51-3.88 (m, 5H) 2.33-2.46 (m, 4H) 1.71-2.08 (m, 5H) 1.29-1.67 (m, 6H);

UPLC-MS (ESI) 471.15 m/z (M+).

Example 28

Preparation of (3R)-3-(2-(2,4-difluorophenyl)-2-(piperidin-1-yl)acetoxy)-1-(2-oxo-2-phenylethyl)-1-azoniabicyclo[2.2.2]octane chloride (C103)

Scheme 29

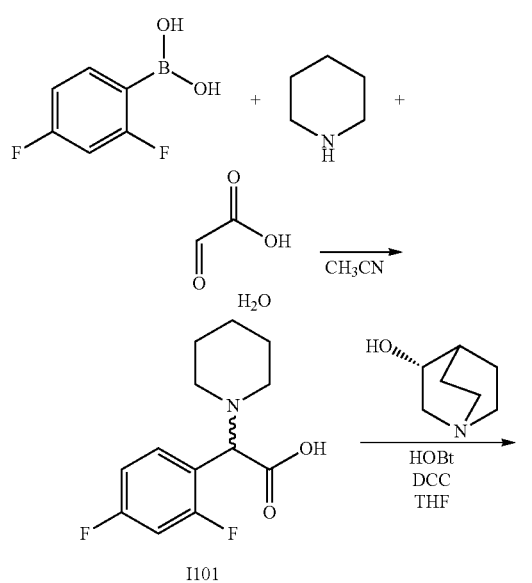

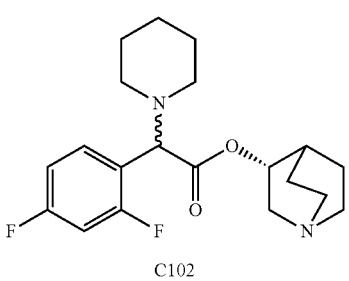

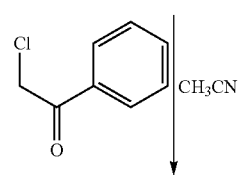

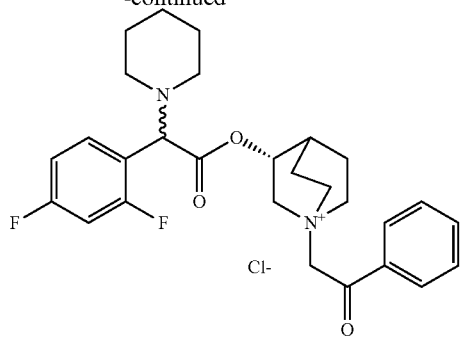

Preparation of 2-(2,4-difluorophenyl)-2-(piperidin-1-yl)acetic acid (I101)

2-Oxoacetic acid (141 mg, 1.90 mmol) and piperidine (0.16 ml, 1.90 mmol) were dissolved in acetonitrile (10 ml). 2,4-Difluorophenylboronic acid (300 mg, 1.90 mmol) was added and the mixture was stirred at reflux for 4 hours. The solvent was evaporated and the crude was purified by flash chromatography (DCM/MeOH=85/25) to obtain the title compound (307 mg, 63% yield) as an off-white solid.

¹H NMR (300 MHz, DMSO-d6) ppm 7.58 (td, 1H), 7.25 (ddd, 1H), 7.13 (m, 1H), 4.39 (s, 1H), 2.56-2.82 (m, 4H), 1.52-1.70 (m, 4H), 1.35-1.52 (m, 2H).

Preparation of (R)-quinuclidin-3-yl 2-(2,4-difluorophenyl)-2-(piperidin-1-yl)acetate (C102)

2-(2,4-Difluorophenyl)-2-(piperidin-1-yl)acetic acid (304 mg, 1.19 mmol), DCC (491 mg, 2.38 mmol), and HOBT (365 mg, 2.38 mmol) were dissolved in dry THF (12 ml). (R)-quinuclidin-3-ol (454 mg, 3.57 mmol) was added and the mixture was stirred at room temperature for 16 hours. THF was evaporated and the residue was taken up with EtOAc and washed with sat. NaHCO₃. The organic phase was dried over Na₂SO₄, filtered and evaporated to dryness. The crude was purified by flash chromatography (DCM/MeOH=9/1+0.1% NH4OH) to obtain the title product as colorless oil (280 mg, 64.5% yield).

¹H NMR (300 MHz, DMSO-d6) ppm 7.44-7.66 (m, 1H), 7.19-7.36 (m, 1H), 7.03-7.18 (m, 1H), 4.63-4.83 (m, 1H), 4.48 (s, 1H), 2.97-3.18 (m, 1H), 2.56-2.79 (m, 5 μl), 2.21-2.47 (m, 4H), 1.74-1.85 and 1.84-1.94 (m, 1H), 1.14-1.69 (m, 10H).

Preparation of (3R)-3-(2-(2,4-difluorophenyl)-2-(piperidin-1-yl)acetoxy)-1-(2-oxo-2-phenylethyl)-1-azoniabicyclo[2.2.2]octane chloride (C103)

(R)-quinuclidin-3-yl 2-(2,4-difluorophenyl)-2-(piperidin-1-yl)acetate (275 mg, 0.75 mmol) and 2-chloro-1-phenylethanone (128 mg, 0.83 mmol) were dissolved in acetonitrile (8 ml) and stirred at room temperature overnight. The solvent was evaporated and the residue was triturated with Et₂O and sonicated. The resulting precipitate was recovered by suction filtration and washed on the filter-paper with EtOAc and Et₂O to obtain the title compound (261 mg, 66.6% yield) as a white solid.

¹H NMR (300 MHz, DMSO-d6) ppm 7.94-8.03 (m, 2H) 7.71-7.80 (m, 1H) 7.49-7.66 (m, 3H) 7.24-7.35 (m, 1H) 7.10-

7.21 (m, 1H) 5.21-5.32 (m, 3H) 4.62 (s, 1H) 4.09-4.25 (m, 1H) 3.56-3.81 (m, 5H) 2.32-2.47 (m, 4H) 2.24-2.31 (m, 1H) 2.00-2.14 (m, 2H) 1.76-1.97 (m, 2H) 1.46-1.61 (m, 4H) 1.33-1.46 (m, 2H).

UPLC-MS (ESI) 483.24 m/z (M+).

Example 29

Preparation of (3R)-1-(2-oxo-2-phenylethyl)-3-(2-(piperidin-1-yl)-2-(thiophen-2-yl)acetoxy)-1-azoniabicyclo[2.2.2]octane chloride (C106)

Scheme 30

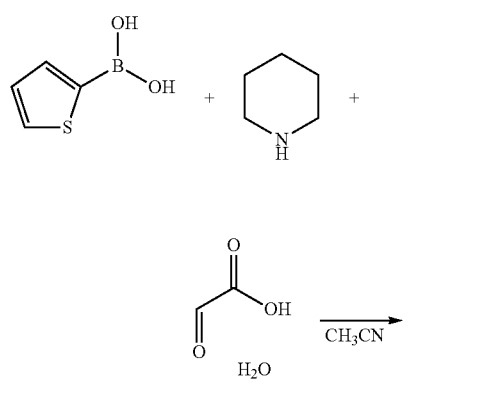

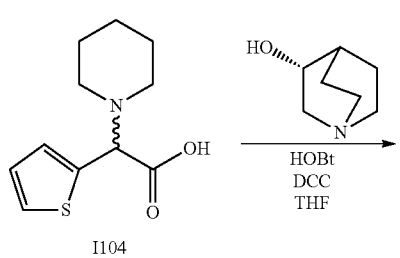

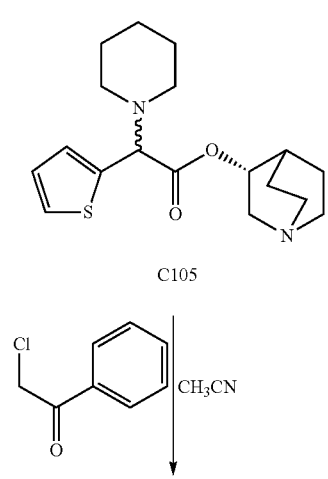

-continued

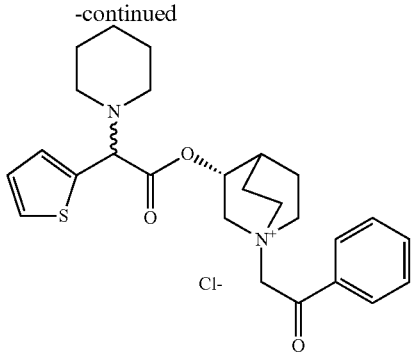

C106

Preparation of (R)-quinuclidin-3-yl 2-(piperidin-1-yl)-2-(thiophen-2-yl)acetate (I104)

A mixture of 2-oxoacetic acid hydrate (216 mg, 2.34 mmol), piperidine (0.23 ml, 2.34 mmol) and thiophen-2-ylboronic acid (300 mg, 2.34 mmol) in acetonitrile (11.7 ml) was heated to reflux for 2.5 hours. The reaction was cooled at room temperature and the suspension was filtered on a buckner funnel washing with acetonitrile (10 ml). The solid was recovered from the filter giving the title compound (528 mg, quantitative yield) as a white solid.

$^1$H NMR (300 MHz, DMSO-d6) ppm 7.54 (dd, 1H) 7.14 (dd, 1H) 7.02 (dd, 1H) 4.55 (s, 1H) 2.61-2.90 (m, 4H) 1.52-1.73 (m, 4H) 1.43 (q, 2H);

UPLC-MS (ESI) 225.9 m/z (MH+).

Preparation of (R)-quinuclidin-3-yl 2-(piperidin-1-yl)-2-(thiophen-2-yl)acetate (C105)

A mixture of 2-(piperidin-1-yl)-2-(thiophen-2-yl)acetic acid (250 mg, 1.11 mmol), DCC (458 mg, 2.22 mmol), HOBT (300 mg, 2.22 mmol) and (R)-quinuclidin-3-ol (282 mg, 2.22 mmol) in dry THF (11.1 ml) was stirred at room temperature under nitrogen atmosphere for 24 hours. The pale pink suspension was filtered washing with THF (5 ml) and the pale pink solution was evaporated. The crude was purified by flash chromatography (DCM/MeOH=95/5+0.4% NH$_4$OH) to obtain the title compound (132 mg, 35.6% yield) as a colorless oil.

$^1$H NMR (300 MHz, DMSO-d6) ppm 7.51 (dd, 1H) 7.02-7.07 (m, 1H) 6.95-7.02 (m, 1H) 4.78 (dd, 1H) 4.43-4.54 (m, 1H) 3.05-3.20 (m, 1H) 2.56-2.83 (m, 4H) 2.37-2.48 (m, 4H) 1.91 (dq, 1H) 1.54-1.76 (m, 2H) 1.43-1.54 (m, 5H) 1.23-1.43 (m, 4H).

UPLC-MS (ESI) 335.0 m/z (MH+).

Preparation of (3R)-1-(2-oxo-2-phenylethyl)-3-(2-(piperidin-1-yl)-2-(thiophen-2-yl)acetoxy)-1-azoniabicyclo[2.2.2]octane chloride (C 106)

2-Chloro-1-phenylethanone (63.0 mg, 0.41 mmol) was added to a solution of (R)-quinuclidin-3-yl 2-(piperidin-1-yl)-2-(thiophen-2-yl)acetate (124 mg, 0.37 mmol) in ethyl acetate (2.5 ml) and acetonitrile (1.2 ml). The pale yellow solution was stirred at room temperature for 24 hours. The solvent was evaporated and the residue was triturated with Et$_2$O (8 ml). The suspension was filtered on a buckner funnel washing with Et$_2$O (5 ml) and the solid was recovered from the filter to collect the title compound (88 mg, 48.5% yield) as a off-white solid.

$^1$H NMR (300 MHz, DMSO-d6) ppm 7.92-8.08 (m, 2H), 7.71-7.83 (m, 1H), 7.47-7.69 (m, 3H), 7.07-7.16 (m, 1H), 6.93-7.07 (m, 1H), 5.33 and 5.34 (s, 2H), 5.22-5.32 (m, 1H), 4.63 and 4.64 (br. s., 1H), 4.11-4.34 (m, 1H), 3.57-3.93 (m, 5H), 2.22-2.48 (m, 5H), 1.85-2.22 (m, 4 µl), 1.31-1.67 (m, 6H).

UPLC-MS (ESI) 453.09 m/z (MH+).

Example 30

Preparation of (3R)-1-(2-oxo-2-phenylethyl)-3-(2-(piperidin-1-yl)-2-(thiophen-3-yl)acetoxy)-1-azoniabicyclo[2.2.2]octane chloride (C109)

Scheme 31

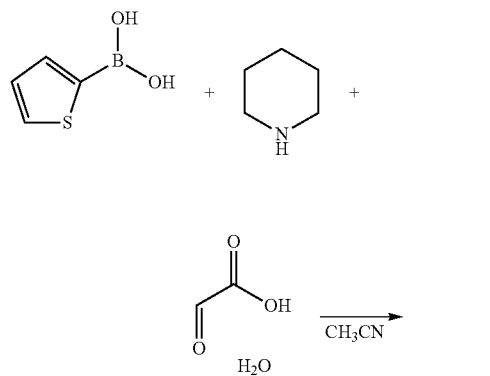

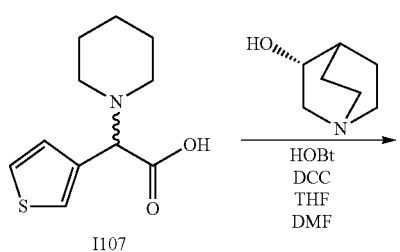

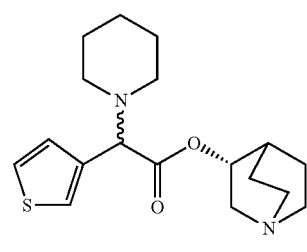

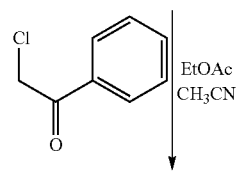

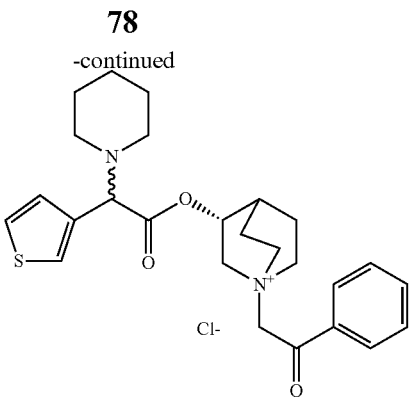

C109

Preparation of 2-(piperidin-1-yl)-2-(thiophen-3-yl) acetic acid (I107)

Thiophen-3-ylboronic acid (300 mg, 2.34 mmol) was added to a solution of 2-oxoacetic acid hydrate (216 mg, 2.34 mmol) and piperidine (0.23 ml, 2.34 mmol) in acetonitrile (11.7 ml). The mixture was heated to reflux for 5 hours. The reaction was cooled to room temperature and the suspension was filtered on a buckner funnel washing with acetonitrile (8 ml). The title compound (528 mg, quantitative yield) was collected from the filter as an off-white solid.

$^1$H NMR (300 MHz, DMSO-d6) ppm 7.42-7.62 (m, 2H), 7.01-7.23 (m, 1H), 4.39 (s, 1H), 2.79-2.97 (m, 2H), 2.60-2.79 (m, 2H), 1.52-1.84 (m, 4H), 1.31-1.52 (m, 2H).

UPLC-MS (ESI) 225.9 m/z (MH+).

Preparation of (R)-quinuclidin-3-yl 2-(piperidin-1-yl)-2-(thiophen-3-yl)acetate (C108)

A mixture of 2-(piperidin-1-yl)-2-(thiophen-3-yl)acetic acid 21c (250 mg, 1.11 mmol), DCC (458 mg, 2.22 mmol), HOBT (340 mg, 2.22 mmol) and (R)-quinuclidin-3-ol (282 mg, 2.22 mmol) in dry THF (11.1 ml) and dry DMF (5.5 ml) was stirred at room temperature under nitrogen for 48 hours. The solvent was evaporated and the crude was purified by flash chromatography (DCM/MeOH=97/3+0.3% NH$_4$OH). The product was triturated with THF (10 ml) to obtain the title compound (217 mg, 58.5% yield) as a colorless oil.

$^1$H NMR (300 MHz, DMSO-d6) δ ppm 7.48-7.55 (m, 1H) 7.39-7.46 (m, 1H) 7.10 (dd, 1H) 4.67-4.80 (m, 1H) 4.26 (s, 1H) 2.99-3.18 (m, 1H) 2.55-2.75 (m, 4H) 2.30-2.46 (m, 5H) 1.80-1.96 (m, 1H) 1.24-1.63 (m, 10H).

UPLC-MS (ESI) 335.0 m/z (MH+).

Preparation of (3R)-1-(2-oxo-2-phenylethyl)-3-(2-(piperidin-1-yl)-2-(thiophen-3-yl)acetoxy)-1-azoniabicyclo[2.2.2]octane chloride (C109)

2-Chloro-1-phenylethanone (107 mg, 0.69 mmol) was added to a solution of (R)-quinuclidin-3-yl 2-(piperidin-1-yl)-2-(thiophen-3-yl)acetate (210 mg, 0.63 mmol) in EtOAc (4.2 ml) and acetonitrile (2.1 ml) and. The mixture was stirred at room temperature for 48 hours. The solvent was evaporated and the crude was purified by flash chromatography (DCM/MeOH=9/1) to collect the title compound (117 mg, 38.1% yield) as an off-white spongy solid.

$^1$H NMR (300 MHz, DMSO-d6) ppm 7.90-8.13 (m, 2H), 7.71-7.86 (m, 1H), 7.44-7.71 (m, 4H), 7.08-7.22 (m, 1H), 5.30 and 5.31 (s, 2H), 5.16-5.29 (m, 1H), 4.40 and 4.42 (s, 1H), 4.12-4.28 (m, 1H), 3.53-3.89 (m, 5H), 2.33-2.47 (m, 4H), 2.23-2.33 (m, 1H), 1.78-2.15 (m, 4H), 1.28-1.64 (m, 6H);

UPLC-MS (ESI) 453.18 m/z (M+).

Legend

*NMR
s=singlet
d=doublet
t=triplet
q=quartet
dd=doublet of doublets
m=multiplet
br=broad
Biological Characterization.

Example 31

Radioligand Binding Assay for Cloned Human Muscarinic Receptors

CHO-K1 clone cells expressing the human M1-, M2-, M3-receptors (Euroscreen, Swissprot P11229, P08172, P20309, Genbank: J02960 respectively) were harvested in $Ca^{++}/Mg^{++}$ free phosphate-buffered saline and collected by centrifugation at 1500 rpm for 10 minutes, at 4° C. min. The pellets were resuspended in ice cold buffer A (15 mM Tris-HCl pH 7.4, 2 mM $MgCl_2$, 0.3 mM EDTA, 1 mM EGTA). Cloned cells expressing M1-, M2-, and M3-receptors were homogenized by a PBI politron (setting 5 for 15 s). The crude membrane fraction was collected by two consecutive centrifugation steps at 40000 g for 20 minutes at 4° C., separated by a washing step in buffer A. The pellets obtained from the three cell lines were finally resuspended in buffer C (75 mM Tris HCl pH 7.4, 12.5 mM $MgCl_2$, 0.3 mM EDTA, 1 mM EGTA, 250 mM sucrose) and aliquots were stored at −80° C.

The day of experiment, M1-, M2-, and M3-receptor frozen membranes were resuspended in buffer D (50 mM Tris-HCl pH 7.4, 2.5 mM $MgCl_2$, 1 mM EDTA). The non selective muscarinic radioligand [3H]-N-methyl scopolamine (Mol. Pharmacol. 45:899-907, which is incorporated herein by reference) was used to label the M1, M2, and M3 binding sites. Binding experiments were performed in duplicate (ten point concentrations curves) in 96 well plates at radioligand concentration of 0.1-0.3 nM. The non specific binding was determined in the presence of cold N-methyl scopolamine 10 µM. Samples (final volume 0.75 mL) were incubated at RT for 120 minutes for M1, 60 minutes for M2 and 90 minutes for M3 binding assay.

The reaction was terminated by rapid filtration through GF/B Unifilter plates and two washes (0.75 mL) with cold buffer using a Packard Filtermate Harvester. Radioactivity on the filters was measured by a microplate scintillation counter TopCount NXT (Canberra Packard).

In the present assays, Ki values for the tested compounds were determined from the observed IC50 values according to known methods. A lower Ki value indicates that the tested compound has a higher binding affinity for the receptor. The interaction with M3 muscarinic receptors can be estimated by the results of in vitro studies which evaluated the potency of the test compounds and the offset of the inhibitory activity produced after washout of the antagonists in isolated guinea pig trachea and by the in vivo duration of action against acetylcholine-induced bronchospasm in the guinea pig.

Example 32

In Vitro Interaction with Guinea Pigs M3 Receptors

The potency of the antagonist activity in isolated guinea pig trachea was investigated following a method previously described by Haddad E B et al. in Br. J. Pharmacol., 127, 413-420, 1999, which is incorporated herein by reference in its entirety, with few modifications. A cumulative concentration-response curve to test antagonists was constructed on preparations precontracted by carbachol, until a complete inhibition of smooth muscle tone was achieved. The concentration of antagonist producing a 50% reversal of carbachol-induced tonic contraction ($IC_{50}$) was taken as a measure of its potency in this bioassay.

In the experiments aimed at assessing the offset of the inhibitory effects produced by test compounds, the minimal concentration of the test compounds known to produce a maximal inhibitory effect was administered to carbachol-precontracted preparations. As soon as the tonic contraction was completely reversed, the organ bath solution was renewed and preparations were thoroughly washed with fresh Krebs solution. Carbachol (0.3 µM) was administered again (at 30 min interval between washout and next administration) during the next 4 hours.

After the administration of carbachol, the inhibitory effects of the compounds of the invention, administered at a concentration of 10 nM, were expressed as percentage of the recovery of the contracting response to carbachol. The percentage of recovery four hours after the washout was lower than 50%. The values ($IC_{50s}$) of inhibitory M3 activity tested on C3 to C109 are comprised between 0.39 and 130 nM.

Example 33

In Vivo Studies on Acetylcholine-Induced Bronchospasm in Guinea Pigs

The in vivo tests on acetylcholine-induced bronchospasm in guinea pig were performed according to H. Konzett H and Rössler F, Arch. Exp. Path. Pharmacol., 195, 71-74, 1940, which is incorporated herein by reference in its entirety. Aqueous solutions of the test compounds were instilled intratracheally in anaesthetised mechanically ventilated guinea pigs. Bronchial response to intravenous acetylcholine challenge was determined before and after drug administration and changes in pulmonary resistance at several time-points were expressed as percent of inhibition of bronchospasm. The bronchodilator activity of the tested compounds persisted unchanged up to 24 hours after the administration.

Example 34

Human Plasma Stability Studies

In order to demonstrate that the compounds are degraded, stability in human plasma at 1 and 5 hours was tested for the compound of the invention. Briefly 10 µl of a stock solution 250 µM of the compound in acetonitrile were added to 1 ml of human plasma and samples were incubated at 37° C. Plasma (504) was taken after 0, 1, and 5 hours of incubation and added to 140 µl of acetonitrile with addition of verapamil as internal standard (250 ng/ml). Samples were analysed by HPLC-MS/MS analysis.

Plasma stability is calculated as percentage remaining after 1 and 5 hours by dividing the peak area at 1 or 5 hours by the area of the peak at time 0. After 1 and 5 hours of incubation, plasma stability being tested for some representative compounds of the invention result to be comprised between 10 and 70% compound remaining, indicating that the compounds of the invention are unstable in human plasma with respect to similar prior art compounds showing, after 1 and 5 hours, a percent compound remaining in human plasma very closed to 100%

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A quinuclidine ester of 1-azaheterocyclylacetic acid represented by formula (I):

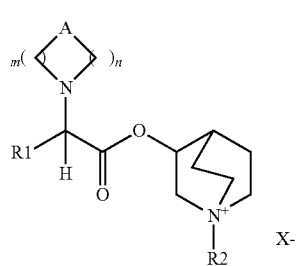

wherein:
A is a single bond, double bond, O, S, SO, $SO_2$, $NR_3$, $C(R_3)R_4$, CO, $C(O)N(R_3)$, $N(R_3)C(O)O$, $SO_2N(R_3)$, $N(R_3)C(O)$, $OC(O)N(R_3)$, $N(R_3)SO_2$, $C(R_3)=C(R_4)$ and $C(R_3)$—$(CH_2)$—$C(R_4)$;
m is an integer of 1 to 4;
n is 0 or an integer of 1 to 4;
R1 is $(C_1-C_{10})$-alkyl, aryl, $(C_3-C_8)$-cycloalkyl, heteroaryl, aryl$(C_1-C_6)$alkyl, or heteroaryl$(C_1-C_6)$alkyl, each of which may be optionally substituted by one or more substituents selected from the group consisting of a halogen atom, OH, oxo (=O), SH, $NO_2$, CN, $CON(R_3)_2$, COOH, $CO_2R_3$, $CF_3$, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, $(C_1-C_{10})$-alkoxyl, aryloxy and heteroaryl;
$X^-$ is a physiologically acceptable anion;
R2 is a group of formula (Y):

—$(CH_2)_p$—P—$(CH_2)_q$-W  (Y)

wherein
p is 0 or an integer of 1 to 4;
q is 0 or an integer of 1 to 4;
P is absent or is selected from the group consisting of O, S, SO, $SO_2$, CO, $NR_3$, CH=CH, $N(R_3)SO_2$, $N(R_3)COO$, $N(R_3)C(O)$, $SO_2N(R_3)$, $CO(O)N(R_3)$, and $C(O)N(R_3)$;
W is H, $(C_1-C_{10})$-alkyl, $(C_1-C_{10})$-alkoxyl, $(C_3-C_8)$-cycloalkyl, aryl, heteroaryl, or $(C_5-C_{10})$heterocycloalkyl, wherein each of said $(C_1-C_{10})$-alkyl, $(C_1-C_{10})$-alkoxyl, $(C_3-C_8)$-cycloalkyl, aryl, heteroaryl, and $(C_5-C_{10})$heterocycloalkyl groups may be optionally substituted by one or more substituents selected from the group consisting of a halogen atom, OH, oxo (=O), SH, $NO_2$, CN, $CON(R_3)_2$, COOH, $NH_2$, $NHCOR_3$, $CO_2R_3$, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, $(C_1-C_{10})$-alkoxyl, $(C_1-C_{10})$alkanoyl, and aryl;
R3 and R4 are each independently H, a halogen atom, $CONH_2$, $(C_1-C_{10})$alkyl, $(C_2-C_6)$alkynyl, $(C_2-C_6)$alkenyl, $(C_1-C_{10})$alkanoyl, $(C_3-C_8)$cycloalkyl, heteroaryl, or aryl, wherein each of said $CONH_2$, $(C_1-C_{10})$alkyl, $(C_2-C_6)$alkynyl, $(C_2-C_6)$alkenyl, $(C_1-C_{10})$alkanoyl, $(C_3-C_8)$cycloalkyl, heteroaryl, and aryl groups may be optionally substituted by one or more substituents selected from the group consisting of a halogen atom, OH, oxo (=O), SH, $NO_2$, CN, $CONH_2$, COOH, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, $(C_1-C_{10})$-alkoxyl, and $(C_3-C_7)$-cycloalkyl.

2. A compound according to claim 1 wherein:
A is O, S, $N(R_3)$, or $C(R_3)R_4$,
R1 is aryl, aryl$(C_1-C_6)$alkyl, or heteroaryl, each of which may be optionally substituted by one or more substituents selected from the group consisting of a halogen atom, $(C_1-C_{10})$alkyl, $(C_1-C_{10})$alkoxyl, aryloxy, and heteroaryl.

3. A compound according to claim 1, wherein:
A is $C(R_3)R_4$,
m and n are both 2,
R1 is aryl or heteroaryl, each of which may be optionally substituted by one or more substituents selected from the group consisting of a halogen atom, $(C_1-C_{10})$alkyl, $(C_1-C_{10})$alkoxyl, aryloxy, and heteroaryl;
R3 is a group of formula (Y):

—$(CH_2)_p$-P—$(CH_2)_q$-W  (Y)

wherein
p is 0, 1, or 3,
P is CO,
Q is 0,
W is s $(C_1-C_{10})$alkyl, aryl, or heteroaryl, each of which may be optionally substituted by one or more substituents selected from the group consisting of a halogen atom, $(C_1-C_{10})$alkyl, $(C_1-C_{10})$alkoxyl, OH, and $(C_1-C_{10})$alkanoyl.

4. A compound according to claim 1, wherein:
W is phenyl, benzothioxolyl, thiophenyl, or thiazolyl, each of which may be optionally substituted by one or more substituents selected from the group consisting of a halogen atom, OH, methyl, and acetyl.

5. A compound according to claim 1, wherein:
$X^-$ is chloride, bromide, iodide, trifluoroacetate, formate, sulfate, phosphate, methanesulfonate, nitrate, maleate, acetate, citrate, fumarate, tartrate, oxalate, succinate, benzoate, or p-toluenesulfonate.

6. A compound of formula (II):

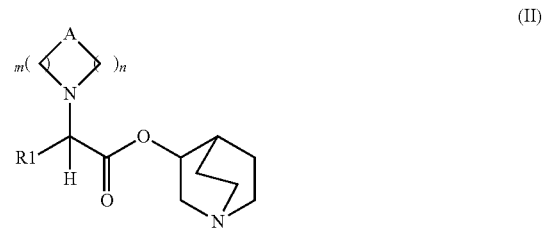

wherein:
  A is a single bond, double bond, O, S, SO, SO2, NR$_3$, C(R$_3$)R$_4$, CO, C(O)N(R$_3$), N(R$_3$)C(O)O, SO$_2$N(R$_3$), OC(O)N(R$_3$), C(R$_3$)=C(R$_4$), or C(R$_3$)—(CH$_2$)—C(R$_4$)
  m is an integer of 1 to 4;
  n is 0 or an integer of 1 to 4;
  R1 is (C$_1$-C$_{10}$)-alkyl, aryl, (C$_3$-C$_8$)-cycloalkyl, heteroaryl, aryl(C$_1$-C$_6$)alkyl, or heteroaryl(C$_1$-C$_6$)alkyl, each of which may be optionally substituted by one or more substituents selected from the group consisting of a halogen atom, OH, oxo (=O), SH, NO$_2$, CN, CON(R$_3$)$_2$, COOH, CO$_2$R$_3$, CF$_3$, (C$_1$-C$_{10}$)-alkoxycarbonyl, (C$_1$-C$_{10}$)-alkylsulfinyl, (C$_1$-C$_{10}$)-alkylsulfonyl, (C$_1$-C$_{10}$)-alkyl, (C$_1$-C$_{10}$)-alkoxyl, aryloxy, and heteroaryl;
  or a pharmaceutical acceptable salt thereof.

7. A process for preparing a compound according to claim 1, comprising:
  (a) coupling a compound of formula (IX) with a compound of formula (X):

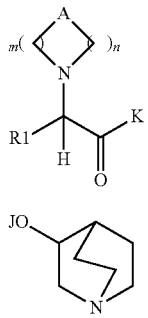

(IX)

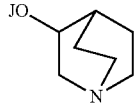

(X)

wherein K is an alkoxy group, an hydroxy group, or an halogen, with a compound of formula (X), in which J is H, Na, Li, or K, to obtain a compounds of formula (II); and
  (b) alkylating said compound of formula (II) with an alkylating agent of formula (XI):

X—R2   (XI)

wherein X is a leaving group selected from the group consisting of a halogen atom, tosylate, triflate, and mesylate, to obtain said compound of formula (I).

8. A pharmaceutical composition, comprising a compound according to claim 1 and one or more pharmaceutically acceptable carriers or excipients.

9. A pharmaceutical composition according to claim 8, which is in a form selected from the group of a powder for inhalation, propellant-driven pressurised metered dose inhaler, and propellant-free nebulised formulation.

10. A pharmaceutical composition, comprising a compound or salt thereof according to claim 6 and one or more pharmaceutically acceptable carriers or excipients.

11. A pharmaceutical composition according to claim 10, which is in a form selected from the group of a powder for inhalation, propellant-driven pressurised metered dose inhaler, and propellant-free nebulised formulation.

12. A combination, comprising a compound according to claim 1 and one or more pharmaceutical active ingredient currently used in the treatment of obstructive, inflammatory respiratory disorders.

13. A combination according to claim 12 wherein said one or more pharmaceutical active ingredient currently used in the treatment of obstructive, inflammatory respiratory disorders is selected from the group consisting of a beta2-agonist, a corticosteroid, an anticholinergic agent, and an antimuscarinic agent.

14. A combination, comprising a compound or salt thereof according to claim 6 and one or more pharmaceutical active ingredient currently used in the treatment of obstructive, inflammatory respiratory disorders.

15. A combination according to claim 14 wherein said one or more pharmaceutical active ingredient currently used in the treatment of obstructive, inflammatory respiratory disorders is selected from the group consisting of a beta2-agonist, a corticosteroid, an anticholinergic agent, and an antimuscarinic agent.

* * * * *

UNITED STATES PATENT AND TRADEMARK OFFICE
CERTIFICATE OF CORRECTION

PATENT NO. : 8,748,613 B2
APPLICATION NO. : 13/729388
DATED : June 10, 2014
INVENTOR(S) : Gabriele Amari et al.

It is certified that error appears in the above-identified patent and that said Letters Patent is hereby corrected as shown below:

In the Specification

In column 3, line 20:
"CO(O)N($R_3$)" should read as --OC(O)N($R_3$)--

In column 3, line 66:
"J is H, Na, Li or K" should read as --J is H (hydrogen), Na (sodium), Li (lithium) or K (potassium)--

In column 5, line 40:
"for instance thienyl, phenyl" should read as --for instance thienyl (thiophenyl), phenyl--

In column 6, lines 25-26:
"R3 is as defined above" should read as --R2, R3 and R4 are as defined above--

In column 6, line 32:
"and R3 is" should read as --and R2 is--

In the Claims

In Claim 1, column 81, line 64:
"CO(O)N($R_3$)" should read as --OC(O)N($R_3$)--

In Claim 3, column 82, line 34:
"R3 is a group" should read as --R2 is a group--

In Claim 3, column 82, line 39:
"Q is 0" should read as --q is 0--

Signed and Sealed this
Twenty-first Day of October, 2014

Michelle K. Lee
*Deputy Director of the United States Patent and Trademark Office*

CERTIFICATE OF CORRECTION (continued)
U.S. Pat. No. 8,748,613 B2

In Claim 3, column 82, line 40:
"W is s $(C_1-C_{10})$alkyl" should read as --W is $(C_1-C_{10})$alkyl--

In Claim 6, column 83, the following should be inserted between lines 14 and 15:
--R3 and R4 are each independently H, a halogen atom, $CONH_2$, $(C_1-C_{10})$alkyl, $(C_2-C_6)$alkynyl, $(C_2-C_6)$alkenyl, $(C_1-C_{10})$alkanoyl, $(C_3-C_8)$cycloalkyl, heteroaryl, or aryl, wherein each of said $CONH_2$, $(C_1-C_{10})$alkyl, $(C_2-C_6)$alkynyl, $(C_2-C_6)$alkenyl, $(C_1-C_{10})$alkanoyl, $(C_3-C_8)$cycloalkyl, heteroaryl, and aryl groups may be optionally substituted by one or more substituents selected from the group consisting of a halogen atom, OH, oxo (=O), SH, $NO_2$, CN, $CONH_2$, COOH, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, $(C_1-C_{10})$-alkoxyl, and $(C_3-C_7)$-cycloalkyl;--

In Claim 7, column 83, lines 37-38:
"J is H, Na, Li or K" should read as --J is H (hydrogen), Na (sodium), Li (lithium) or K (potassium)--